US011014975B2

(12) United States Patent
Sabatino et al.

(10) Patent No.: US 11,014,975 B2
(45) Date of Patent: May 25, 2021

(54) EXPRESSION CASSETTE FOR PACKAGING AND EXPRESSION OF VARIANT FACTOR VIII FOR THE TREATMENT OF HEMOSTASIS DISORDERS

(71) Applicant: THE CHILDREN'S HOSPITAL OF PHILADELPHIA, Philadelphia, PA (US)

(72) Inventors: Denise Sabatino, Havertown, PA (US); Katherine A. High, Merion Station, PA (US); Liron Elkouby, Wynnewood, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 15/503,120

(22) PCT Filed: Aug. 13, 2015

(86) PCT No.: PCT/US2015/045142
§ 371 (c)(1),
(2) Date: Feb. 10, 2017

(87) PCT Pub. No.: WO2016/025764
PCT Pub. Date: Feb. 18, 2016

(65) Prior Publication Data

US 2017/0233456 A1 Aug. 17, 2017

Related U.S. Application Data

(60) Provisional application No. 62/036,936, filed on Aug. 13, 2014.

(51) Int. Cl.
*C12N 15/86* (2006.01)
*C07K 14/755* (2006.01)
*A61K 48/00* (2006.01)

(52) U.S. Cl.
CPC .......... *C07K 14/755* (2013.01); *A61K 48/005* (2013.01); *A61K 48/0008* (2013.01); *A61K 48/0066* (2013.01); *C12N 15/86* (2013.01); *C12N 2750/14143* (2013.01); *C12N 2840/007* (2013.01)

(58) Field of Classification Search
CPC ................ C07K 14/755; A61K 48/005; A61K 48/0008; A61K 48/0066; C12N 15/86; C12N 2840/007; C12N 2750/14143; A61P 9/00; A61P 7/04; A61P 7/02; A61P 17/02
See application file for complete search history.

(56) References Cited

U.S. PATENT DOCUMENTS

| | | | | |
|---|---|---|---|---|
| 6,114,148 | A | 9/2000 | Seed et al. | |
| 6,221,349 | B1 * | 4/2001 | Couto | A61K 38/37 424/93.1 |
| 6,924,365 | B1 * | 8/2005 | Miller | C07K 14/755 435/320.1 |
| 2009/0197338 | A1 * | 8/2009 | Vandenberghe | A61K 48/0091 435/471 |
| 2010/0284971 | A1 * | 11/2010 | Samulski | C07K 14/755 424/93.2 |
| 2012/0028900 | A1 | 2/2012 | Kaufman et al. | |
| 2012/0308641 | A1 | 12/2012 | Arruda et al. | |
| 2015/0361158 | A1 * | 12/2015 | Tan | C12N 9/6424 424/134.1 |

FOREIGN PATENT DOCUMENTS

| | | | |
|---|---|---|---|
| AU | 2013/202564 | A1 | 5/2013 |
| WO | 2014/064277 | A1 | 5/2004 |
| WO | 2007/149852 | A2 | 12/2007 |
| WO | 2011/005968 | A1 | 1/2011 |

OTHER PUBLICATIONS

Siner et al. "Minimal modification in the factor VIII B-domain sequence ameliorates the murine hemophilia A phenotype." Blood. May 23, 2013;121(21):4396-403. (Year: 2013).*
Spencer et al. "663. High Expression Bioengineered Factor VIII Enables AAV-Based Gene Therapy of Hemophilia A" Hematologic and Immunologic Gene & Cell Therapy, vol. 21, supplement 1, S253, May 1, 2013'663' (Year: 2013).*
High et al. "Adeno-associated viral vectors for the treatment of hemophilia" Human Molecular Genetics, vol. 25, Issue R1, Apr. 15, 2016, pp. R36-R41, (Year: 2016).*
Scott et al. "Gene therapy for haemophilia: prospects and challenges to prevent or reverse inhibitor formation." Br J Haematol. Feb. 2012; 156(3): 295-302. (Year: 2012).*
Brown et al. "Bioengineered coagulation factor VIII enables long-term correction of murine hemophilia A following liver-directed adeno-associated viral vector delivery." Mol Ther Methods Clin Dev. Aug. 6, 2014;1:14036. (Year: 2014).*
Expression vector [retrieved on Mar. 20, 2018]. Sep. 7, 2012, https://web.archive.org/web/20120907162824/http://en. wikipedia.org:80/wiki/Expression_vector.
Gnatenko, D. V., et al., Human factor VIII can be packaged and functionally expressed in an adeno-associated virus background: applicability to haemophilia A gene therapy, Br. J. Haematol.,1999, 104(1):27-36.
Qian, X. et al., Optimization of AAV Vectors for Liver-Directed Gene Therapy of Hemophilia A, Mol. Ther., 2001, 3(5):S184-S192.
PCT International Application No. PCT/US15/45142, International Search Report and Written Opinion dated Feb. 9, 2016.

(Continued)

*Primary Examiner* — Titilayo Moloye
(74) *Attorney, Agent, or Firm* — Pillsbury Winthrop Shaw Pittman LLP

(57) ABSTRACT

Factor VIII variants and methods of use thereof are disclosed. In particular embodiments, Factor VIII variants are expressed more efficiently by cells over wild-type Factor VIII proteins, are secreted at increased levels by cells over wild-type Factor VIII proteins, exhibit enhanced activity over wild-type Factor VIII proteins and are packaged more efficiently into viral vectors.

50 Claims, 11 Drawing Sheets

Specification includes a Sequence Listing.

(56) References Cited

OTHER PUBLICATIONS

Costa, R.H., et al., Site-directed mutagenesis of hepatocyte nuclear factor (HNF) binding sites in the mouse transthyretin (TTR) promoter reveal synergistic interactions with its enhancer region, Nucleic Acids Research, 1991, 19 (15):4139-4145.

Pasquini, S., et al., The effect of CpG sequences on the B cell response to a viral glycoprotein encoded by a plasmid vector, 1999, Gene Therapy, 6:1448-1455.

Reyes-Sandoval, A., et al., CpG methylation of a plasmid vector results in extended transgene product expression by circumventing induction of immune responses, Molecular Therapy, 2004, 9(2):249-261.

Ward, N.J., et al., Codon optimization of human factor VIII cDNAs leads to high-level expression, Blood, 2011, 117 (3):798-807.

* cited by examiner

EXPRESSION CASSETTE FOR PACKAGING AND EXPRESSION OF VARIANT FACTOR VIII FOR THE TREATMENT OF HEMOSTASIS DISORDERS

RELATED APPLICATIONS

This application is the National Phase of International Application No. PCT/US2015/045142, filed Aug. 13, 2015 which designated the U.S. and that International Application was published under PCT Article 21(2) in English, and claims priority to application Ser. No. 62/036,936, filed Aug. 13, 2014, all of which applications are expressly incorporated herein by reference in their entirety, including all text, tables, sequence listings and drawings.

SEQUENCE LISTING

The instant application contains a Sequence Listing which has been submitted electronically in ASCII format and is hereby incorporated by reference in its entirety. Said ASCII copy, created on Feb. 9, 2017, is named "CHOP0451078_ST25.txt" and is 59,196 bytes in size.

FIELD OF THE INVENTION

This invention relates to the fields of recombinant coagulation factor production and the treatment of medical disorders associated with aberrant hemostasis. More particularly, the invention provides an improved expression cassette which more efficiently packages the Factor VIII variant sequence of the invention, the improved variant also exhibiting enhanced activity over wild-type Factor VIII proteins.

INTRODUCTION

Several publications and patent documents are cited throughout the specification in order to describe the state of the art to which this invention pertains. Each of these citations is incorporated herein by reference as though set forth in full.

Hemophilia is an X-linked bleeding disorder present in 1 in 5,000 males worldwide. Therapies aimed at increasing clotting factor levels just above 1% of normal are associated with substantial improvement of the severe disease phenotype. Recent clinical trials for AAV-mediated gene transfer for hemophilia B (HB) have demonstrated sustained long-term expression of therapeutic levels of factor IX (FIX) but established that the AAV vector dose may be limiting due to anti-AAV immune responses to the AAV capsid. While these data relate the hemophilia B, 80% of all hemophilia is due to FVIII deficiency, hemophilia A (HA).

Current treatment for this disease is protein replacement therapy that requires frequent infusion of the factor VIII protein. There is an immediate need to achieve sustained therapeutic levels of factor VIII expression so that patients no longer require such frequent protein treatments. Indeed, continuous factor VIII expression would prevent bleeding episodes and may ensure that immune tolerance to the protein is established.

In summary, gene therapy for HA presents 3 distinct challenges: (1) intrinsic properties of human FVIII (hFVIII) make it difficult to express compared to other proteins of similar size (2) the large size of the FVIII cDNA and sequence specific effects are correlated with rearrangements which hamper AAV production and (3) high rates of anti- FVIII antibody (inhibitors) formation in response to protein therapy that occurs in 25-30% of severe (<1% FVIII) HA patients.

The invention provides improved Factor VIII variants useful for treatment in patients in need thereof, such as a patient with HA.

SUMMARY

In accordance with the invention, codon-optimized Factor VIII (FVIII) encoding nucleic acid variants distinct from wild-type nucleic acid encoding wild-type FVIII are provided. Such codon-optimized FVIII encoding nucleic acid variants encode FVIII protein, optionally without a B domain, such as FVIII protein (e.g., human FVIII protein) without a B domain (see, e.g., FIG. 1). Such codon-optimized FVIII encoding nucleic acid variants exhibit increased expression, 4-5 fold for a particular codon-optimized sequence (CO/CO3), when transferred into a cell (see, e.g., FIG. 6B), leading to increased FVIII protein secretion and therefore activity (see, e.g., FIG. 7). Such codon-optimized FVIII encoding nucleic acid variants also are packaged more efficiently in different AAV vector serotypes, leading to increased production of AAV vectors across AAV serotypes (see, e.g., Tables 3-5).

Surprisingly, these features dramatically increase FVIII expression, as compared to expression of wild-type nucleic acid encoding wild-type FVIII, or expression of wild type FVIII without B domain, and also increase packaging efficiency into an AAV vector, leading to higher vector yields. Codon-optimized FVIII encoding sequences may exhibit a reduction in rearrangement events that impact the integrity of the FVIII transgene after AAV packaging that is observed with wild type FVIII and other codon-optimized hFVIII transgenes, e.g., CO/CO3 is superior to either of CO1 and CO2. In addition, non-codon optimized and codon-optimized FVIII variants that have a single amino acid change or small deletion (1-4 amino acids) at a PACE-furin cleavage site can exhibit increased secretion in vivo (non-codon optimized FIG. 3B, and codon-optimized FIG. 6B), and specific activity of the FVIII protein. Invention FVIII encoding nucleic acid variants, that encode FVIII with or without B-domain, and/or with or without mutated PACE-furin cleavage recognition site can increase expression of FVIII, increase production of AAV vector, as well as provide increased efficacy in the context of gene transfer by increased circulating levels of FVIII and achieving hemostasis with lower FVIII thereby reducing the effective dose required for beneficial therapeutic outcomes.

In one embodiment, a Factor VIII (FVIII) encoding nucleic acid variant exhibits greater expression when compared to wild type FVIII expression. In another embodiment, a Factor VIII (FVIII) encoding nucleic acid variant comprises a B domain deletion and exhibits greater expression when compared to wild type FVIII comprising a B domain deletion expression. In an additional embodiment, FVIII encoding nucleic acid variant is more efficiently packaged into a viral vector such as an adenovirus-associated virus (AAV) vector.

In a further embodiment, a FVIII encoded by said nucleic acid variant exhibits greater biological activity when compared to wild type FVIII or when compared to wild type FVIII comprising a B domain deletion (e.g., as determined by a clotting assay or reduced bleeding in a FVIII assay or FVIII deficiency model).

In still further embodiments, codon optimized FVIII encoding nucleic acid variants encode FVIII protein with a mutated PACE-furin cleavage recognition site, referred to as a variant FVIII or FVIII protein. Such codon-optimized FVIII nucleic acid variants that encode FVIII protein with mutated PACE-furin cleavage recognition site exhibit increased secretion and blood clotting activity (see, e.g., FIGS. 2, 6 and 7). In particular aspects, FVIII encoding nucleic acid variants have 1, 2, 3 or all 4 of the codons encoding the PACE/furin cleavage site of FVIII substituted or deleted. In such aspects, variant FVIII proteins encoded by such FVIII nucleic acid variants have 1, 2, 3 or all 4 of the PACE/furin cleavage site of FVIII substituted or deleted. In more particular aspects, 1, 2, 3 or all 4 of the codons encoding the PACE/furin cleavage site set forth as HHQR or RHQR from positions 1645-1648 is/are deleted in FVIII encoding nucleic acid variants.

In additional aspects, FVIII encoding nucleic acid variants have one or more leucine codons changed to CTG compared to TTA, TTG, CTT, CTC or CTA in wild type FVIII encoding nucleic acid. In further aspects, FVIII encoding nucleic acid variants have 2-5, 5-10, 10-20, 20-50, 50-100, 100-250, 250-500, 500-750 or 750-850 CTG leucine codons modified from TTA, TTG, CTT, CTC or CTA leucine codons in wild type FVIII encoding nucleic acid. In yet additional aspects, FVIII encoding nucleic acid variants have greater than 85% CTG leucine codons modified from TTA, TTG, CTT, CTC or CTA leucine codons in wild type FVIII encoding nucleic acid. In still further aspects, FVIII encoding nucleic acid variants have all CTG leucine codons modified from TTA, TTG, CTT, CTC or CTA leucine codons in wild type FVIII encoding nucleic acid. In particular aspects, FVIII encoding nucleic acid variants have between about 50-59%, or 50-56%, or 50-53% GC content. In other aspects, FVIII encoding nucleic acid variants have one or more AAG lysine codons compared to AAA lysine codons in wild type FVIII encoding nucleic acid.

In still additional embodiments, FVIII encoding nucleic acid variant are at least 75% identical to wild type human FVIII nucleic acid or wild type human FVIII nucleic acid comprising a B domain deletion. In more particular aspects, FVIII encoding nucleic acid variant are about 75-85% identical (e.g., about 75%, 76%, 77%, 78%, 79%, 80%, 81%, 82%, 83%, 84% or 85% identical) to wild type human FVIII nucleic acid or wild type human FVIII nucleic acid comprising a B domain deletion.

In particular aspects, FVIII encoding nucleic acid variants are set forth in any of SEQ ID NOs:1-7 and 9.

In various embodiments, FVIII encoding nucleic acid variants are mammalian, such as human. Such mammalian FVIII encoding nucleic acid variants including human forms may be based upon wild type FVIII or wild type FVIII comprising a B domain deletion.

In accordance with the invention, also provided are expression vectors that include FVIII encoding nucleic acid variants as set forth herein. In particular embodiments, an expression vector comprises an adenovirus-associated virus (AAV) vector, a retroviral vector, an adenoviral vector, a plasmid, or a lentiviral vector. In particular aspects, an AAV vector comprises an AAV1, AAV2, AAV3, AAV4, AAV5, AAV6, AAV7, AAV8, AAV9, AAV10, AAV11, Rh10, Rh74 or AAV-2i8 AAV serotype.

Expression vectors can include additional components or elements. In particular embodiments, an expression vector such as AAV vector further includes an intron, an expression control element, one or more AAV inverted terminal repeats (ITRs) (e.g., any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof) and/or a filler polynucleotide sequence. In particular aspects, an intron is within or flanks a FVIII encoding nucleic acid variant, and/or an expression control element is operably linked to the FVIII encoding nucleic acid variant, and/or an AAV ITR(s) flanks the 5' or 3' terminus of the FVIII encoding nucleic acid variant, and/or a filler polynucleotide sequence flanks the 5' or 3'terminus of the FVIII encoding nucleic acid variant.

In particular aspects, an expression control element comprises a constitutive or regulatable control element, or a tissue-specific expression control element or promoter. In more particular aspects, an expression control element comprises an element that confers expression in liver. In additional particular aspects, an expression control element comprises a TTR promoter or mutant TTR promoter, such as SEQ ID NO:8.

In accordance with the invention, additionally provided are host cells expressing the FVIII encoded by the nucleic acid variants as set forth herein. In particular embodiments, a host cell includes FVIII encoding nucleic acid variant or an expression vector comprising a FVIII encoding nucleic acid variant. In particular aspects, such host cells produce FVIII protein encoded by the nucleic acid variants and FVIII protein produced is recovered. Such FVIII protein produced by the cells, optionally isolated and/or purified, can be administered to a subject as set forth herein.

In accordance with the invention, further provided are virus vectors that include the FVIII encoding nucleic acid variants or the expression vectors comprising the FVIII encoding nucleic acid variants. In particular embodiments, a virus vector comprises an AAV vector. In particular aspects, an AAV vector comprises a VP1, VP2 and/or VP3 capsid sequence having 75% or more sequence identity (e.g., 80%, 85%, 90%, 95%, 96%, 97%, 98%, 99%, 99.1%, 99.2%, 99.3%, 99.4%, 99.5%, 99.6%, 99.7%, 99.8%, etc.) to AAV1, AAV2, AAV3, AAV4, AAV5, AAV6, AAV7, AAV8, AAV9, AAV10, AAV11, Rh10, Rh74 or AAV-2i8 VP1, VP2 and/or VP3 sequences. In more particular aspects, an AAV vector comprises a VP1, VP2 and/or VP3 capsid sequence selected from any of: AAV1, AAV2, AAV3, AAV4, AAV5, AAV6, AAV7, AAV8, AAV9, AAV10, AAV11, Rh10, Rh74 and AAV-2i8 AAV serotypes.

In accordance with the invention, yet additionally provided are compositions comprising FVIII encoding nucleic acid variants set forth herein. In particular embodiments, pharmaceutical compositions include an expression vector, or a virus or AAV vector, in a biologically compatible carrier or excipient. Such pharmaceutical compositions optionally include empty capsid AAV (e.g., lack vector genome comprising FVIII encoding nucleic acid variant). In additional particular embodiments, FVIII encoding nucleic acid variants, expression vectors, or virus or AAV vectors are encapsulated in a liposome or mixed with phospholipids or micelles.

In accordance with the invention, still further provided are methods for delivering or transferring FVIII encoding nucleic acid variants into a mammal or a mammalian cell. In one embodiment, a method includes administering or contacting a FVIII encoding nucleic acid variant, an expression vector comprising FVIII encoding nucleic acid variant, or a virus or AAV vector comprising a FVIII encoding nucleic acid variant to a mammal or mammalian cell, thereby delivering or transferring the nucleic acid sequence into the mammal or mammalian cell. Such methods introduce FVIII encoding nucleic acid variants into a mammalian cell in culture or in a subject (e.g., a patient).

Methods of the invention also include treating mammalian subjects (e.g., patients) such as humans in need of Factor VIII (the human produces an insufficient amount of Factor VIII protein, or a defective or aberrant Factor VIII protein). In one embodiment, a method of treating a mammal in need of Factor VIII, includes: providing a FVIII encoding nucleic acid variant, or an expression vector comprising FVIII encoding nucleic acid variant, or a virus or AAV vector comprising a FVIII encoding nucleic acid variant; and administering an amount of the FVIII encoding nucleic acid variant, or an expression vector comprising FVIII encoding nucleic acid variant, or a virus or AAV vector comprising a FVIII encoding nucleic acid variant to the mammalian subject such that Factor VIII encoded by the FVIII encoding nucleic acid variant, is expressed in the mammalian subject.

In another embodiment, a method for treatment of a hemostasis related disorder in a patient in need thereof (e.g., the patient produces an insufficient amount of Factor VIII protein, or a defective or aberrant Factor VIII protein) includes administration of a therapeutically effective amount of a FVIII encoding nucleic acid variant, or an expression vector comprising FVIII encoding nucleic acid variant, or a virus or AAV vector comprising a FVIII encoding nucleic acid variant in a biologically acceptable carrier to the patient.

In particular aspects of the invention methods, Factor VIII is expressed at levels having a beneficial or therapeutic effect on the mammal; and/or Factor VIII is expressed in a cell, tissue or organ of the mammal. Such aspects include introduction of FVIII encoding nucleic acid variant into a tissue or organ such as liver. Such aspects also include introduction of FVIII encoding nucleic acid variant into a secretory cell. Such aspects further include introduction of FVIII encoding nucleic acid variant into an endocrine cell or an endothelial cell. Such aspects additionally include introduction of FVIII encoding nucleic acid variant into an hepatocyte, a sinusoidal endothelial cell, a megakaryocyte, a platelet or hematopoetic stem cell.

Candidate subjects (e.g., a patient) and mammals (e.g., humans) for administration (e.g., delivery) of a FVIII encoding nucleic acid variant, or an expression vector comprising FVIII encoding nucleic acid variant, or a virus or AAV vector comprising a FVIII encoding nucleic acid variant include those having or those at risk of having a disorder such as: hemophilia A, von Willebrand diseases and bleeding associated with trauma, injury, thrombosis, thrombocytopenia, stroke, coagulopathy, disseminated intravascular coagulation (DIC) or over-anticoagulation treatment disorder.

Candidate subjects (e.g., a patient) and mammals (e.g., humans) for administration (e.g., delivery) of a FVIII encoding nucleic acid variant, or an expression vector comprising FVIII encoding nucleic acid variant, or a virus or AAV vector comprising a FVIII encoding nucleic acid variant include those or sero-negative for AAV antibodies, as well as those having or those at risk of developing AAV antibodies. Such subjects (e.g., a patient) and mammals (e.g., humans) may be sero-negative or sero-positive for an AAV1, AAV2, AAV3, AAV4, AAV5, AAV6, AAV7, AAV8, AAV9, AAV10, AAV11, AAV-Rh10 or AAV-Rh74 serotype.

Methods of the invention therefore further include administering empty capsid AAV to said mammal or said patient. In particular embodiments, empty capsid of AAV1, AAV2, AAV3, AAV4, AAV5, AAV6, AAV7, AAV8, AAV9, AAV10, AAV11, AAV-12, AAV-Rh10 and/or AAV-Rh74 serotype is further administered to the mammal or patient.

Methods of administration (e.g., delivery) in accordance with the invention include any mode of contact or delivery, ex vivo or in vivo. In particular embodiments administration (e.g., delivery) is: intravenously, intraarterially, intramuscularly, subcutaneously, intra-cavity, intubation, or via catheter.

The invention also provide methods for testing the improved FVIII variants in small and large animal models that are tolerant to human FVIII in order to assess dosing and monitor immunogenicity of the variants. The HB dog model is superior for predicting the effective dose required for human FIX gene therapy. Moreover, use of this model provides a setting that allows assessment of humans currently receiving protein replacement therapy with hFVIII-BDD without evidence of an anti-hFVIII antibody response who are likely to develop an immune response to such variants.

DETAILED DESCRIPTION

Figure 1:
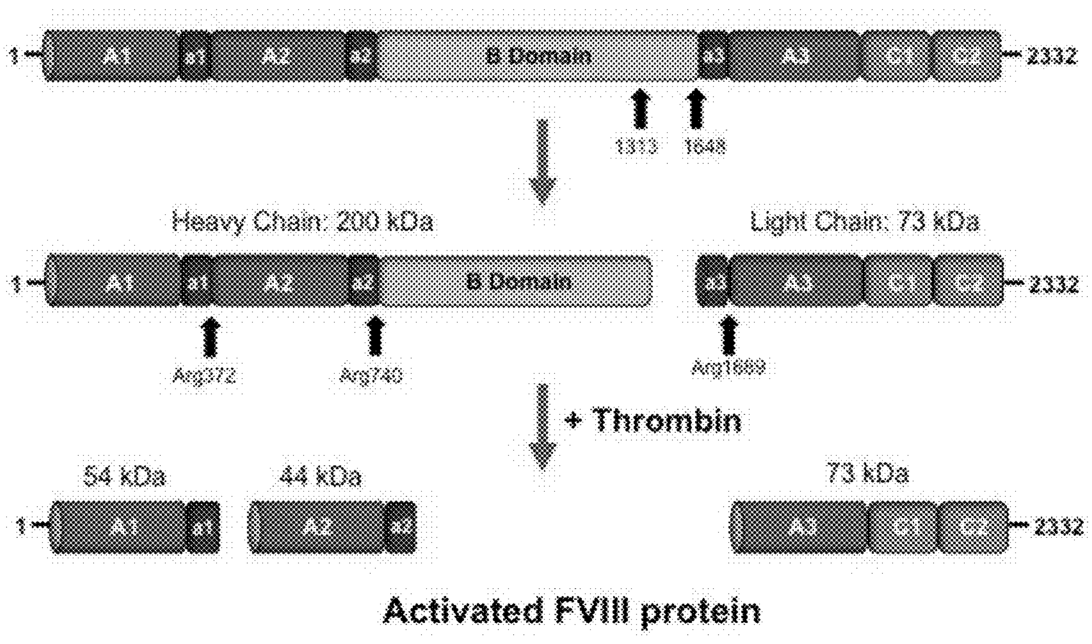
FIG. 1 shows proteolytic cleavages of factor VIII. FVIII has a domain structure consisting of three A domains (A1, A2, and A3), two C domains (C1 and C2), and a large B domain encoded by exon 14 of the gene that is dispensable for FVIII function. FVIII functions as a cofactor in the activation of factor X to factor Xa in a reaction catalyzed by factor IXa. The FVIII is secreted as a heterodimer composed of FVIII heavy and light chains that are stabilized in the circulation by von Willebrand factor (vWF). Upon thrombin cleavage, FVIII forms the activated heterotrimer.

Previous reports have shown that AAV liver gene therapy of canine FVIII (cFVIII) results in long-term expression of therapeutic levels of FVIII in naïve HA dogs (Sabatino et al. Mol Ther 19, 442-449, 2011). This strategy also eradicated inhibitors to cFVIII in HA dogs with pre-existing neutralizing cFVIII antibodies (Finn, J. D. et al., Blood 116, 5842-5848, 2010). These data demonstrate that AAV-FVIII can significantly improve the disease phenotype and eliminate FVIII inhibitors. Interestingly, cFVIII is inherently more stable than human FVIII (hFVIII), resulting in increased biological activity (Sabatino, D. E. et al. Blood 114, 4562-4565, 2009). Thus, the AAV dose of cFVIII does not predict the therapeutic dose of hFVIII. This is in contrast to factor IX that has similar biological activity in both species and predicted the therapeutic AAV dose in humans. Notably, the hemophilia dog model has been an excellent predictor of both efficacy and immune response to the transgene in liver and muscle trials for HB.

To understand the biochemical basis for enhanced function of cFVIII, we identified a PACE-furin cleavage recognition site in FVIII that is unique in cFVIII compared to all other species, including hFVIII. Introduction of a single amino acid change at this site in hFVIII confers increased stability and higher biological activity to hFVIII (Siner, J. I., et al. Blood 121, 4396-4403, 2013).

Disclosed herein are nucleic acid variants that encode human FVIII, distinct from wild-type nucleic acid that encode FVIII. Such nucleic acid variants that encode human FVIII are expressed at increased levels in cells and/or animals, which in turn can provide increased FVIII protein levels in vivo. Also disclosed herein are nucleic acid variants that encode human FVIII that can be packaged more efficiently by AAV across different serotypes. Further disclosed herein are nucleic acid variants that encode human FVIII protein variants having higher stability and/or biological activity in vitro and/or in vivo.

Still further disclosed herein are data showing efficacy and safety of AAV delivery of several variants of human FVIII in animal models of hemophilia A. In particular, for example, codon-optimized nucleic acid that encode human FVIII with and without deletions in the intracellular protease cleavage recognition site exhibit one or more of the following: 1) increased expression in cells and/or animals; 2) increased activity, as reflected by increased clotting, for example; 3) increased stability; and 4) achieve therapeutic effect at lower AAV doses than native hFVIII, with no apparent increase in immunogenicity over the currently used B-domain deleted FVIII constructs.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally modified or altered polynucleotides (e.g., variant nucleic acid). Polynucleotides can be single, double, or triplex, linear or circular, and can be of any length. In discussing polynucleotides, a sequence or structure of a particular polynucleotide may be described herein according to the convention of providing the sequence in the 5' to 3' direction.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular example of a modification or variant is a codon-optimized nucleic acid sequence that encodes FVIII.

A "nucleic acid" or "polynucleotide" variant refers to a modified sequence which has been genetically altered compared to wild-type. The sequence may be genetically modified without altering the encoded protein sequence. Alternatively, the sequence may be genetically modified to encode a variant protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of the protein (FVIII) encoded thereby, and some codons of the nucleic acid variant will be changed which in turn changes the amino acids of the protein (FVIII) encoded thereby.

Figure 2:
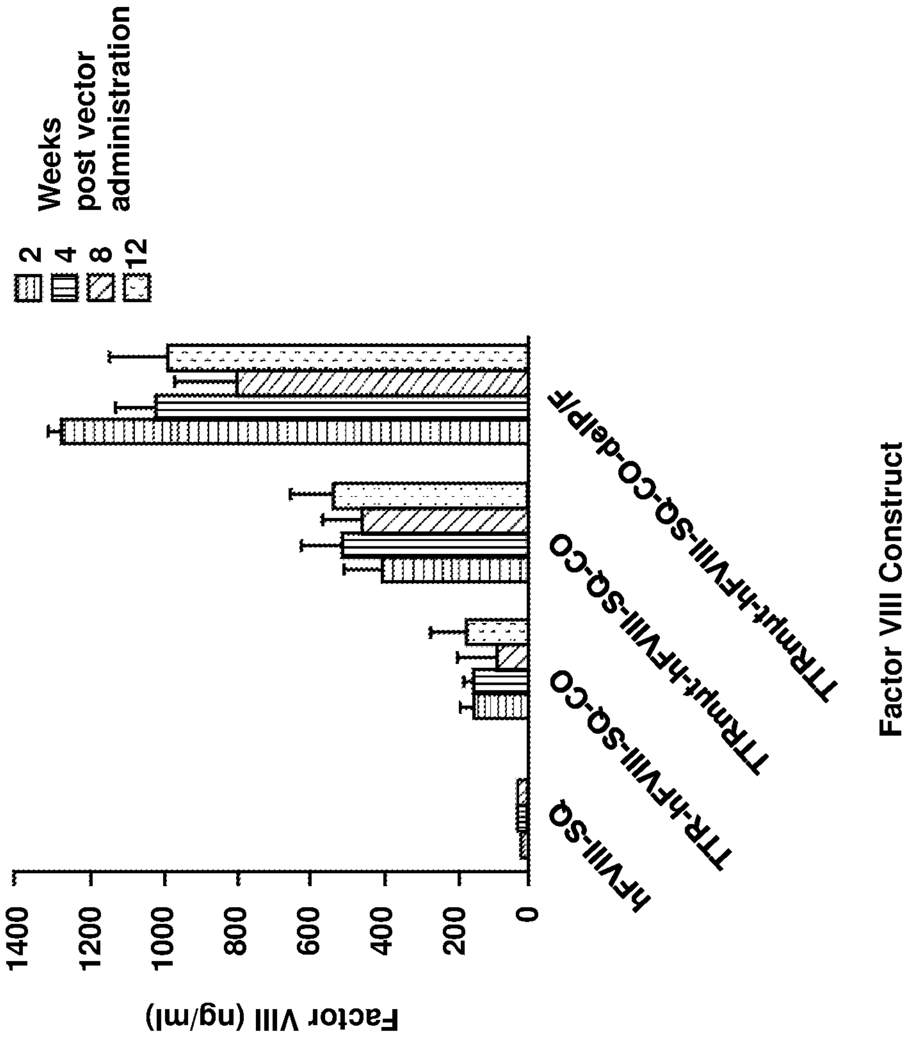
FIG. 2 shows Factor VIII Expression after AAV Delivery of codon-optimized factor VIII. The codon-optimized human factor VIII gene (CO) was delivered in an adeno-associated viral vector serotype 8 to hemophilia A/CD4 knockout mice. The mice were delivered $1\times10^{11}$ vector genomes (vg)/mouse of hFVIII-SQ (wild type factor VIII cDNA), TTR-hFVIII-SQ-CO, TTRmut-hFVIII-SQ-CO or TTRmut-hFVIII-SQ-CO-delP/F. ELISA was performed on plasma collected at 2, 4, 8 and 12 weeks post vector administration to determine the factor VIII protein levels in the circulation.

The term "variant Factor VIII (FVIII)" refers to a modified FVIII which has been genetically altered such that the encoded protein exhibits increased expression when compared to when compared to unmodified wild-type FVIII or FVIII-BDD. Such a variant can be referred to as a "Factor VIII (FVIII) encoding nucleic acid variant." An increase of at least 30-fold was attained with the $TTR_{mut}$-hFVIII-SQ-CO delP/F expression cassette compared to HCR/hAAT promoter driving wild-type hFVIII (FIG. 2). Particular examples of such FVIII modifications are codon-optimized FVIII encoding variants which exhibit increased expression and/or increased packaging efficiency into AAV vectors compared to non codon-optimized wild-type FVIII or FVIII-BDD, and do so without modifications to the nucleic acid that result in amino acid changes to the encoded FVIII protein. When comparing expression, if the variant FVIII protein retains the B-domain, it is appropriate to compare it to wild-type FVIII expression; and if the variant FVIII protein has a B-domain deletion, it be compared to expression of wild-type FVIII that also has a B-domain deletion.

A "variant Factor VIII (FVIII)" can also mean a modified FVIII protein such that the modified protein has an amino acid alteration compared to wild-type FVIII and exhibits an increase in activity and/or stability compared to wild-type FVIII. Examples of such particular FVIII protein modifications are genetic modifications that lead to PACE-furin cleavage recognition site mutations, deletions or substitutions in the FVIII protein, referred to herein as a variant FVIII protein. When comparing activity and/or stability, if the variant FVIII protein retains the B-domain, it is appropriate to compare it to wild-type FVIII; and if the variant FVIII protein has a B-domain deletion, it be compared to wild-type FVIII that also has a B-domain deletion.

The nucleotide sequences described herein are readily obtainable from GenBank. For human FVIII, see Accession No. NG-011403.1. For canine FVIII, see Accession No. NM-001003212-1. FVIII-BDD, hFVIII-BDD, cFVIII-BDD and the like refer to a FVIII variant which lacks the B domain (see, e.g., FIG. 1).

The "polypeptides," "proteins" and "peptides" encoded by the "nucleic acid" or "polynucleotide" sequences," include full-length native (FVIII) sequences, as with naturally occurring wild-type proteins, as well as functional subsequences, modified forms or sequence variants so long as the subsequence, modified form or variant retain some degree of functionality of the native full-length protein. For example, a FVIII protein can have a B-domain deletion as set forth herein and retain clotting function. In methods and uses of the invention, such polypeptides, proteins and peptides encoded by the nucleic acid sequences can be but are not required to be identical to the endogenous protein that is defective, or whose expression is insufficient, or deficient in the treated mammal.

Non-limiting examples of modifications include one or more nucleotide or amino acid substitutions (e.g., 1-3, 3-5, 5-10, 10-15, 15-20, 20-25, 25-30, 30-40, 40-50, 50-100, 100-150, 150-200, 200-250, 250-500, 500-750, 750-850 or more nucleotides or residues). An example of a nucleic acid modification is codon optimization, e.g., for a leucine codon that is not CTG to be modified to CTG, or a lysine codon that is not AAG to be modified to AAG. Another example of a nucleic acid codon optimization modification is increasing GC content. In particular aspects, a variant nucleic acid sequence encoding human FVIII protein has 1-5% more GC content than native sequence encoding human Factor FVIII (e.g., 1, 2, 3, 4 or 5% more GC content); or has 5-10% more GC content than native (wild-type) sequence encoding human Factor FVIII (e.g., 5, 6, 7, 8, 9 or 10% more GC content); or has 10-15% more GC content than native (wild-type) sequence encoding human Factor FVIII (e.g., 10, 11, 12, 13, 14 or 15% more GC content).

An example of an amino acid modification is a conservative amino acid substitution or a deletion (e.g., subsequences or fragments, or deletion of PACE/furin cleavage site) of a reference sequence, e.g. FVIII. In particular embodiments, a modified or variant sequence retains at least part of a function or activity of unmodified sequence.

All mammalian and non-mammalian forms of nucleic acid encoding proteins, including other mammalian forms of the FVIII nucleic acid and FVIII proteins disclosed herein are expressly included, either known or unknown. Thus, the invention includes genes and proteins from non-mammals, mammals other than humans, and humans, which genes and proteins function in a substantially similar manner to the FVIII (e.g., human) genes and proteins described herein.

The term "vector" refers to small carrier nucleic acid molecule, a plasmid, virus (e.g., AAV vector), or other vehicle that can be manipulated by insertion or incorporation of a nucleic acid. Such vectors can be used for genetic manipulation (i.e., "cloning vectors"), to introduce/transfer polynucleotides into cells, and to transcribe or translate the inserted polynucleotide in cells. An "expression vector" is a specialized vector that contains a gene or nucleic acid sequence with the necessary regulatory regions needed for expression in a host cell. A vector nucleic acid sequence generally contains at least an origin of replication for propagation in a cell and optionally additional elements, such as a heterologous polynucleotide sequence, expression control element (e.g., a promoter, enhancer), intron, ITR(s), selectable marker (e.g., antibiotic resistance), polyadenylation signal.

A viral vector is derived from or based upon one or more nucleic acid elements that comprise a viral genome. Particular viral vectors include lentivirus, pseudo-typed lentivirus and parvo-virus vectors, such as adeno-associated virus (AAV) vectors. Also provided are vectors comprising a nucleic acid sequence encoding a variant FVIII polypeptide.

The term "recombinant," as a modifier of vector, such as recombinant viral, e.g., lenti- or parvo-virus (e.g., AAV) vectors, as well as a modifier of sequences such as recombinant polynucleotides and polypeptides, means that the compositions have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. An example of a recombinant polynucleotide would be where a nucleic acid (e.g., gene) encoding a FVIII protein is cloned into a vector, with or without 5', 3' and/or intron regions that the gene is normally associated within the viral (e.g., AAV) genome. Although the term "recombinant" is not always used herein in reference to vectors, such as viral and AAV vectors, as well as sequences such as polynucleotides, recombinant forms including polynucleotides, are expressly included in spite of any such omission.

A recombinant viral "vector" or "AAV vector" is derived from the wild type genome of a virus, such as AAV by using molecular methods to remove the wild type genome from the virus (e.g., AAV), and replacing with a non-native nucleic acid, such as a FVIII encoding nucleic acid variant sequence. Typically, for AAV one or both inverted terminal repeat (ITR) sequences of AAV genome are retained in the AAV vector. A "recombinant" viral vector (e.g., AAV) is distinguished from a viral (e.g., AAV) genome, since all or a part of the viral genome has been replaced with a non-native sequence with respect to the viral (e.g., AAV) genomic nucleic acid such as FVIII encoding nucleic acid variant sequence. Incorporation of a non-native sequence therefore defines the viral vector (e.g., AAV) as a "recombinant" vector, which in the case of AAV can be referred to as a "rAAV vector."

A recombinant vector (e.g., lenti-, parvo-, AAV) sequence can be packaged-referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins.

A vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the nucleic acid that is packaged or encapsidated by virus (e.g., AAV).

A "transgene" is used herein to conveniently refer to a nucleic acid that is intended or has been introduced into a cell or organism. Transgenes include any nucleic acid, such as a gene that encodes a polypeptide or protein (e.g., Factor VIII).

In a cell having a transgene, the transgene has been introduced/transferred by way of vector, such as AAV, "transduction" or "transfection" of the cell. The terms "transduce" and "transfect" refer to introduction of a molecule such as a nucleic acid into a cell or host organism. The transgene may or may not be integrated into genomic nucleic acid of the recipient cell. If an introduced nucleic acid becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism extrachromosomally, or only transiently.

A "transduced cell" is a cell into which the transgene has been introduced. Accordingly, a "transduced" cell (e.g., in a mammal, such as a cell or tissue or organ cell), means a genetic change in a cell following incorporation of an exogenous molecule, for example, a nucleic acid (e.g., a transgene) into the cell. Thus, a "transduced" cell is a cell into which, or a progeny thereof in which an exogenous nucleic acid has been introduced. The cell(s) can be propagated and the introduced protein expressed, or nucleic acid transcribed. For gene therapy uses and methods, a transduced cell can be in a subject.

An "expression control element" refers to nucleic acid sequence(s) that influence expression of an operably linked nucleic acid. Control elements, including expression control elements as set forth herein such as promoters and enhancers, Vector sequences including AAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of certain vectors, such as AAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence e.g., Factor VIII (FVIII) encoding nucleic acid variant. A promoter typically increases an amount expressed from operably linked nucleic acid as compared to an amount expressed when no promoter exists.

An "enhancer" as used herein can refer to a sequence that is located adjacent to the heterologous polynucleotide. Enhancer elements are typically located upstream of a promoter element but also function and can be located downstream of or within a sequence (e.g., Factor VIII (FVIII) encoding nucleic acid variant). Hence, an enhancer element can be located 100 base pairs, 200 base pairs, or 300 or more base pairs upstream or downstream of Factor VIII (FVIII) encoding nucleic acid variant. Enhancer elements typically increase expressed of an operably linked nucleic acid above expression afforded by a promoter element.

An expression construct may comprise regulatory elements which serve to drive expression in a particular cell or tissue type. Expression control elements (e.g., promoters) include those active in a particular tissue or cell type, referred to herein as a "tissue-specific expression control elements/promoters." Tissue-specific expression control elements are typically active in specific cell or tissue (e.g., liver). Expression control elements are typically active in particular cells, tissues or organs because they are recognized by transcriptional activator proteins, or other regulators of transcription, that are unique to a specific cell, tissue or organ type. Such regulatory elements are known to those of skill in the art (see, e.g., Sambrook et al. (1989) and Ausubel et al. (1992)).

The incorporation of tissue specific regulatory elements in the expression constructs of the invention provides for at least partial tissue tropism for the expression of the variant FVIIIs or functional fragments thereof. Examples of promoters that are active in liver are the TTR promoter, human alpha 1-antitrypsin (hAAT) promoter; albumin, Miyatake, et al. *J. Virol.,* 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.,* 7:1503-14 (1996)], among others. An example of an enhancer active in liver is apolipoprotein E (apoE) HCR-1 and HCR-2 (Allan et al., *J. Biol. Chem.,* 272:29113-19 (1997)).

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, *Cell,* 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA,* 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997). 1; and the rapamycin-inducible system (Magari, et al., *J. Clin. Invest.* 100:2865-2872 (1997); Rivera, et al., *Nat. Medicine.* 2:1028-1032 (1996)). Other regulatable control elements which may be useful in this context are those which are regulated by a specific physiological state, e.g., temperature, acute phase, development.

Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

The term "operably linked" means that the regulatory sequences necessary for expression of a coding sequence are placed in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

An intron can also function as a filler or stuffer polynucleotide sequence in order to achieve a length for AAV vector packaging into a virus particle. Introns and intron fragments that function as a filler or stuffer polynucleotide sequence also can enhance expression.

The phrase "hemostasis related disorder" refers to bleeding disorders such as hemophilia A, hemophilia A patients with inhibitory antibodies, deficiencies in coagulation Factors, VII, VIII, IX and X, XI, V, XII, II, von Willebrand factor, combined FV/FVIII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

With reference to nucleic acids of the invention, the term "isolated" refers to a nucleic acid molecule that is separated from one or more sequences with which it is immediately contiguous (in the 5' and 3' directions) in the naturally occurring genome (genomic DNA) of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule. Alternatively, this term may refer to a protein which has been sufficiently separated from other proteins with which it would naturally be associated, so as to exist in "substantially pure" form.

The term "isolated" does not exclude combinations produced by the hand of man, for example, a recombinant vector (e.g., rAAV) sequence, or virus particle that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or about 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes, and is defined as a nucleic acid molecule comprised of two or more ribo- or deoxyribonucleotides, such as more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire length or a portion of the sequence. In particular aspects, the length of the sequence sharing the percent identity is 2, 3, 4, 5 or more contiguous nucleic acids or amino acids, e.g., 6, 7, 8, 9, 10, 11, 12, 13, 14, 15, 16, 17, 18, 19, 20, etc. contiguous nucleic acids or amino acids. In additional particular aspects, the length of the sequence sharing identity is 21 or more contiguous nucleic acids or amino acids, e.g., 21, 22, 23, 24, 25, 26, 27, 28, 29, 30, 31, 32, 33, 34, 35, 36, 37, 38, 39, 40, etc. contiguous nucleic acids or amino acids. In further particular aspects, the length of the sequence sharing identity is 41 or more contiguous nucleic acids or amino acids, e.g. 42, 43, 44, 45, 45, 47, 48, 49, 50, etc., contiguous nucleic acids or amino acids. In yet further particular aspects, the length of the sequence sharing identity is 50 or more contiguous nucleic acids or amino acids, e.g., 50-55, 55-60, 60-65, 65-70, 70-75, 75-80, 80-85, 85-90, 90-95, 95-100, 100-110, etc. contiguous nucleic acids or amino acids.

As set forth herein, Factor VIII (FVIII) encoding nucleic acid variants will be distinct from (e.g, non wild-type) but will exhibit sequence identity with wild-type FVIII encoding nucleic acid. In codon optimized FVIII encoding nucleic acid variants, denoted CO1, CO2 and CO/CO3, at the nucleotide sequence level, a codon optimized FVIII encoding nucleic acid variant will typically be at least about 70% identical, more typically about 75% identical, even more typically about 80%-85% identical to wild-type FVIII encoding nucleic acid. Thus, for example, a codon optimized FVIII encoding nucleic acid variant may have 75%-85% identity to wild-type FVIII encoding gene, or to each other, i.e., CO1 vs. CO2, CO1 vs. CO3, CO2 vs. CO3, etc. as set forth herein.

At the amino acid sequence level, a variant such as a variant FVIII protein will be at least about 70% identical, more typically about 80% identical, even more typically about 90% or more identity. In other embodiments, a variant such as a variant FVIII protein has at least 90%, 91%, 92%, 93%, 94%, 95%, 96%, 97%, 98%, 99% or more identity to a reference sequence, e.g. wild-type FVIII protein with or without B-domain.

To determine identity, if the variant FVIII (FVIII encoding nucleic acid variant or FVIII protein) retains the B-domain, it is appropriate to compare identity to wild-type FVIII. If the variant FVIII (FVIII encoding nucleic acid variant or FVIII protein) has a B-domain deletion, it is appropriate to compare identity to wild-type FVIII that also has a B-domain deletion.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) or "percent identity" between two sequences can be ascertained using a computer program and/or mathematical algorithm. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); *Pearson, Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Nucleic acid molecules, expression vectors (e.g., vector genomes), plasmids, including Factor VIII (FVIII) encoding nucleic acid variants of the invention may be prepared by using recombinant DNA technology methods. The availability of nucleotide sequence information enables preparation of isolated nucleic acid molecules of the invention by a variety of means. For example, Factor VIII (FVIII) encoding nucleic acid variants can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids of the invention may be maintained as DNA in any convenient cloning vector. In a one embodiment, clones are maintained in a plasmid cloning/expression vector, such as pBluescript (Stratagene, La Jolla, Calif.), which is propagated in a suitable *E. coli* host cell. Alternatively, nucleic acids may be maintained in vector suitable for expression in mammalian cells. In cases where post-translational modification affects coagulation function, nucleic acid molecule can be expressed in mammalian cells.

Factor VIII (FVIII) encoding nucleic acid variants of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid of the invention. Such oligonucleotides are useful as probes for detecting FVIII expression.

A B-domain deleted, codon optimized FVIII encoding nucleic acid variant of the invention, optionally encoding FVIII polypeptide variant with or without a PACE/Furin cleavage site mutation, deletion or substitution, or a functional fragment of either as described herein, may be prepared in a variety of ways, according to known methods. The protein may be purified from appropriate sources, e.g., transformed bacterial or animal cultured cells or tissues which express engineered FVIII by immunoaffinity purification.

The availability of invention variant nucleic acid molecules encoding FVIII, optionally encoding FVIII polypeptide variant with or without a PACE/Furin cleavage site mutation, deletion or substitution, or a functional fragment of either as described herein, enables production of FVIII using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to an embodiment, larger quantities of FVIII may be produced by expression in a suitable prokaryotic or eukaryotic expression system. For example, part or all of a Factor VIII (FVIII) encoding nucleic acid variant for example, may be inserted into a plasmid vector adapted for expression in a bacterial cell, such as *E. coli* or a mammalian cell line such as baby hamster kidney (BHK), CHO or Hela cells. Alternatively, in an embodiment, tagged fusion proteins comprising FVIII can be generated. Such FVIII-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells.

Vectors such as those described herein comprise the regulatory elements necessary for expression of the DNA in the host cell positioned in such a manner as to permit expression of the encoded protein in the host cell. Such regulatory elements required for expression include, but are not limited to, promoter sequences, enhancer sequences and transcription initiation sequences as set forth herein and known to the skilled artisan.

Factor VIII (FVIII) encoding nucleic acid variant optionally encoding variant FVIII proteins as set forth herein, produced by gene expression in a recombinant prokaryotic or eukaryotic system, may be purified according to methods known in the art. In an embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

FVIII proteins, prepared by the aforementioned methods, may be analyzed according to standard procedures. For example, such proteins may be assessed for altered coagulation properties according to known methods.

As disclosed herein, a convenient way of producing a polypeptide according to the invention is to express nucleic acid encoding it, by use of the nucleic acid in an expression system. A variety of expression systems of utility for the methods of the invention are well known to those of skill in the art.

Accordingly, the invention also provides methods of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems.

Methods and uses of the invention of the invention include delivering (transducing) nucleic acid (transgene) into host cells, including dividing and/or non-dividing cells. The nucleic acids, recombinant vector (e.g., rAAV), methods, uses and pharmaceutical formulations of the invention are additionally useful in a method of delivering, administering or providing a protein to a subject in need thereof, as a method of treatment. In this manner, the nucleic acid is transcribed and the protein may be produced in vivo in a subject. The subject may benefit from or be in need of the protein because the subject has a deficiency of the protein, or because production of the protein in the subject may impart some therapeutic effect, as a method of treatment or otherwise.

Vectors including lenti- or parvo-virus vector (e.g., AAV) sequences, recombinant virus particles, methods and uses may be used to deliver a Factor VIII (FVIII) encoding nucleic acid variant with a biological effect to treat or ameliorate one or more symptoms associated with a FVIII deficiency or abnormality. Recombinant lenti- or parvo-virus vector (e.g., AAV) sequences, plasmids, recombinant virus particles, methods and uses may be used to provide therapy for various disease states involving or due to a FVIII deficiency or abnormality.

Invention nucleic acids, vectors, recombinant vectors (e.g., rAAV), and recombinant virus particles, methods and uses permit the treatment of genetic diseases, e.g., a FVIII deficiency. For deficiency state diseases, gene transfer can be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

In particular embodiments, Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either, may be used, for example, as therapeutic and/or prophylactic agents (protein or nucleic acid) which modulate the blood coagulation cascade or as a transgene in gene. For example, Factor VIII (FVIII) encoding nucleic acid variants may have similar coagulation activity as wild-type FVIII, or altered coagulation activity compared to wild-type FVII, such as in the case of a variant FVIII protein (e.g., a codon optimized nucleic acid variant encoding variant FVIII protein with a PACE/Furin cleavage site mutation, deletion or substitution), or a functional fragment. Cell-based strategies allow continuous expression of Factor VIII (FVIII) encoding nucleic acid variant or FVIII protein variants in hemophilia A patients. As disclosed herein, certain modifications of FVIII molecules (nucleic acid and protein) result in increased expression at the nucleic acid level, increased packaging efficiency by virus (e.g., AAV) vector, and increased coagulation activity and greater stability at the protein level thereby effectively improving hemostasis.

Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either may be used for a variety of purposes in accordance with the invention. In one embodiment, a nucleic acid delivery vehicle (i.e., an expression vector) for modulating blood coagulation is provided wherein the expression vector comprises a Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either as described herein. Administration of FVIII-encoding expression vectors to a patient results in the expression of FVIII protein which serves to alter the coagulation cascade. In accordance with the invention, a Factor VIII (FVIII) encoding nucleic acid variant may encode a FVIII polypeptide as described herein (e.g., a variant FVIII protein with a PACE/Furin cleavage site mutation, deletion or substitution), or a functional fragment, whose expression increases hemostasis. In one embodiment, a Factor VIII (FVIII) encoding nucleic acid variant encodes a FVIII polypeptide variant, such as a FVIII protein with a PACE/Furin cleavage site mutation, deletion or substitution, or a functional fragment thereof.

In additional embodiments of the invention, compositions and methods are provided for administration of a viral vector comprising a Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either. In one embodiment, the expression vector comprising Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either, is a viral vector.

Expression vectors comprising Factor VIII (FVIII) encoding nucleic acid variant (e.g., codon optimized variant encoding FVIII), a variant FVIII protein encoding nucleic acid variant (e.g., codon optimized variant encoding variant FVIII with a PACE/Furin cleavage site mutation, deletion or substitution), or a functional fragment of either may be administered alone, or in combination with other molecules useful for modulating hemostasis. According to the invention, the expression vectors or combination of therapeutic agents may be administered to the patient alone or in a pharmaceutically acceptable or biologically compatible compositions.

Viral vectors such as lenti- and parvo-virus vectors, including AAV serotypes and variants thereof provide a means for delivery of nucleic acid into cells ex vivo, in vitro and in vivo, which encode proteins such that the cells express the encoded protein. AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example. Because AAV are not associated with pathogenic disease in humans, AAV vectors are able to deliver heterologous polynucleotide sequences (e.g., therapeutic proteins and agents) to human patients without causing substantial AAV pathogenesis or disease.

Viral vectors which may be used in the invention include, but are not limited to, adeno-associated virus (AAV) vectors of multiple serotypes (e.g., AAV-1 to AAV-12, and others) and hybrid/chimeric AAV vectors, lentivirus vectors and pseudo-typed lentivirus vectors [e.g., Ebola virus, vesicular stomatitis virus (VSV), and feline immunodeficiency virus (FIV)], herpes simplex virus vectors, adenoviral vectors (with or without tissue specific promoters/enhancers), vaccinia virus vectors, retroviral vectors, lentiviral vectors, non-viral vectors and others.

AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. Non-viral vectors, for example, based on plasmid DNA or minicircles, are also suitable gene transfer vectors for a large gene as that encoding FVIII.

It may be desirable to introduce a vector that can provide, for example, multiple copies of a desired gene and hence greater amounts of the product of that gene. Improved AAV and lentiviral vectors and methods for producing these vectors have been described in detail in a number of references, patents, and patent applications, including: Wright J. F. (Hum Gene Ther 20:698-706, 2009) a technology used for the production of clinical grade vector at Children's Hospital of Philadelphia. Lentiviral vector can also be produced at CHOP and the other vectors are available through the Lentivirus vector production core laboratory by NHLBI Gene Therapy Resource Program (GTRP)—Lentivirus Vector Production Core Laboratory.

Accordingly, in various embodiments of the invention a vector includes a lenti- or parvo-viral vector, such as an adeno-viral vector. In particular embodiments, a recombinant vector is a parvovirus vector. Parvoviruses are small viruses with a single-stranded DNA genome. "Adeno-associated viruses" (AAV) are in the parvovirus family.

Accordingly, the invention provides viral vectors that include Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either. For example, a recombinant AAV vector can include a nucleic acid encoding a desired protein (e.g., Factor VIII), such as a codon optimized Factor VIII (FVIII) encoding nucleic acid variant (e.g., codon optimized variant encoding FVIII), where the encoded FVIII protein optionally has B-domain deletion, variant FVIII protein encoding nucleic acid variants (e.g., codon optimized nucleic acid variants encoding variant FVIII protein with a PACE/Furin cleavage site mutation, deletion or substitution), or a functional fragment of either. Vector delivery or administration to a subject (e.g., mammal) therefore provides FVIII (via e.g., codon optimized nucleic acid variant encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either, to a subject such as a mammal (e.g., human).

Direct delivery of vectors or ex-vivo transduction of human cells followed by infusion into the body will result in FVIII expression thereby exerting a beneficial therapeutic effect on hemostasis. In the context of invention Factor VIII described herein, such administration enhances pro-coagulation activity.

AAV vectors and lentiviral vectors do not typically include viral genes associated with pathogenesis. Such vectors typically have one or more of the wild type AAV genes deleted in whole or in part, for example, rep and/or cap genes, but retain at least one functional flanking ITR sequence, as necessary for the rescue, replication, and packaging of the recombinant vector into an AAV vector particle. For example, only the essential parts of vector e.g., the ITR and LTR elements, respectively are included. An AAV vector genome would therefore include sequences required in cis for replication and packaging (e.g., functional ITR sequences)

Recombinant AAV vector, as well as methods and uses thereof, include any viral strain or serotype. As a non-limiting example, a recombinant AAV vector can be based upon any AAV genome, such as AAV-1, -2, -3, -4, -5, -6, -7, -8, -9, -10, -11, -12, -rh74, -rh10 or AAV-2i8, for example. Such vectors can be based on the same strain or serotype (or subgroup or variant), or be different from each other. As a non-limiting example, a recombinant AAV vector based upon one serotype genome can be identical to one or more of the capsid proteins that package the vector. In addition, a recombinant AAV vector genome can be based upon an AAV (e.g., AAV2) serotype genome distinct from one or more of the AAV capsid proteins that package the vector. For example, the AAV vector genome can be based upon AAV2, whereas at least one of the three capsid proteins could be a AAV1, AAV3, AAV4, AAV5, AAV6, AAV7, AAV8, AAV9, AAV10, AAV11, AAV12, Rh10, Rh74 or AAV-2i8 or variant thereof, for example.

In particular embodiments, adeno-associated virus (AAV) vectors include AAV1, AAV2, AAV3, AAV4, AAV5, AAV6, AAV7, AAV8, AAV9, AAV10, AAV11, AAV12, Rh10, Rh74 and AAV-2i8, as well as variants (e.g., capsid variants, such as amino acid insertions, additions and substitutions) thereof as set forth in WO 2013/158879 (International Application PCT/US2013/037170) and WO 2015/013313 (International Application PCT/US2014/047670). AAV variants include AAV1, AAV2, AAV3, AAV4, AAV5, AAV6, AAV7, AAV8, AAV9, AAV10, AAV11, AAV12, Rh10, Rh74 and AAV-2i8 variants. Accordingly, AAV vectors and AAV variants (e.g., capsid variants) that include (encapsidate or package) Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either, are provided.

AAV and AAV variants (e.g., capsid variants) serotypes (e.g., VP1, VP2, and/or VP3 sequences) may or may not be distinct from other AAV serotypes, including, for example, AAV1-AAV12, Rh74 or Rh10 (e.g., distinct from VP1, VP2, and/or VP3 sequences of any of AAV1-AAV12, Rh74 or Rh10 serotypes).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

AAV vectors therefore include gene/protein sequences identical to gene/protein sequences characteristic for a particular serotype. As used herein, an "AAV vector related to AAV1" refers to one or more AAV proteins (e.g., VP1, VP2, and/or VP3 sequences) that has substantial sequence identity to one or more polynucleotides or polypeptide sequences that comprise AAV1. Analogously, an "AAV vector related to AAV8" refers to one or more AAV proteins (e.g., VP1, VP2, and/or VP3 sequences) that has substantial sequence identity to one or more polynucleotides or polypeptide sequences that comprise AAV8. An "AAV vector related to AAV-Rh74" refers to one or more AAV proteins (e.g., VP1, VP2, and/or VP3 sequences) that has substantial sequence identity to one or more polynucleotides or polypeptide sequences that comprise AAV-Rh74. Such AAV vectors related to another serotype, e.g., AAV1, AAV2, AAV3, AAV4, AAV5, AAV6, AAV7, AAV8, AAV9, AAV10, AAV11, AAV12, Rh10, Rh74 or AAV-2i8, can therefore have one or more distinct sequences from AAV1, AAV2, AAV3, AAV4, AAV5, AAV6, AAV7, AAV8, AAV9, AAV10, AAV11, AAV12, Rh10, Rh74 and AAV-2i8, but cart exhibit substantial sequence identity to one or more genes and/or proteins, and/or have one or more functional characteristics of AAV1, AAV2, AAV3, AAV4, AAV5, AAV6, AAV7, AAV8, AAV9, AAV10, AAV11, AAV12, Rh10, Rh74 or AAV-2i8 (e.g., such as cell/tissue tropism). Exemplary non-limiting AAV variants include capsid variants of any of VP1, VP2, and/or VP3.

In various exemplary embodiments, an AAV vector related to a reference serotype has a polynucleotide, polypeptide or subsequence thereof that includes or consists of a sequence at least 80% or more (e.g., 85%, 90%, 95%, 96%, 97%, 98%, 99%, 99.1%, 99.2%, 99.3%, 99.4%, 99.5%, etc.) identical to one or more AAV1, AAV2, AAV3, AAV4, AAV5, AAV6, AAV7, AAV8, AAV9, AAV10, AAV11, AAV12, Rh10, Rh74 or AAV-2i8 (e.g., such as VP1, VP2, and/or VP3 sequences).

Compositions, methods and uses of the invention include AAV sequences (polypeptides and nucleotides), and subsequences thereof that exhibit less than 100% sequence identity to a reference AAV serotype such as AAV1, AAV2, AAV3, AAV4, AAV5, AAV6, AAV7, AAV8, AAV9, AAV10, AAV11, AAV12, Rh10, or AAV-2i8, but are distinct from and not identical to known AAV genes or proteins, such as AAV1, AAV2, AAV3, AAV4, AAV5, AAV6, AAV7, AAV8, AAV9, AAV10, AAV11, AAV12, Rh10, Rh74 or AAV-2i8, genes or proteins, etc. In one embodiment, an AAV polypeptide or subsequence thereof includes or consists of a sequence at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to any reference AAV sequence or subsequence thereof, such as AAV1, AAV2, AAV3, AAV4, AAV5, AAV6, AAV7, AAV8, AAV9, AAV10, AAV11, AAV12, Rh10, Rh74 or AAV-2i8 (e.g., VP1, VP2 and/or VP3). In particular aspects, an AAV variant has 1, 2, 3, 4, 5, 5-10, 10-15, 15-20 or more amino acid substitutions.

Recombinant AAV vectors, including AAV1, AAV2, AAV3, AAV4, AAV5, AAV6, AAV7, AAV8, AAV9, AAV10, AAV11, AAV12, Rh10, Rh74 or AAV-2i8 and variant, related, hybrid and chimeric sequences, can be constructed using recombinant techniques that are known to the skilled artisan, to include one or more nucleic acid sequences (transgenes) flanked with one or more functional AAV ITR sequences.

In one embodiment of the invention, FVIII polypeptide variants, such as a human FVIII variant with a PACE-furin cleavage recognition site mutation, deletion or substitution, may be administered to a patient via infusion in a biologically compatible carrier, for example, via intravenous injection. The FVIII polypeptide variants, such as a human FVIII variant with a PACE-furin cleavage recognition site mutation, deletion or substitution of the invention may optionally be encapsulated into liposomes or mixed with other phospholipids or micelles to increase stability of the molecule. FVIII protein with a PACE/Furin cleavage site mutation, deletion or substitution, or a functional fragment, may be administered alone or in combination with other agents known to modulate hemostasis (e.g., Factor V, Factor Va or derivatives thereof).

An appropriate composition in which to deliver FVIII polypeptide variants, such as a human FVIII variant with a PACE-furin cleavage recognition site mutation, deletion or substitution may be determined by a medical practitioner upon consideration of a variety of physiological variables, including, but not limited to, the patient's condition and hemodynamic state. A variety of compositions well suited for different applications and routes of administration are well known in the art and are described hereinbelow.

A preparation containing purified FVIII protein, such as FVIII variant with a PACE/Furin cleavage site mutation, deletion or substitution, or a functional fragment, contains a physiologically acceptable matrix and may be formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing FVIII variant can be stored in the form of a finished solution or in lyophilized or deep-frozen form.

A preparation can be stored in lyophilized form and is dissolved into a visually clear solution using an appropriate reconstitution solution. Alternatively, the preparation according to the invention can also be made available as a liquid preparation or as a liquid that is deep-frozen. The preparation according to the invention may optionally be especially stable, i.e., it can be allowed to stand in dissolved form for a prolonged time prior to administration or delivery.

The preparation according to the invention can be made available as a pharmaceutical preparation with FVIII activity in the form of a one-component preparation or in combination with other factors in the form of a multi-component preparation. Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, such as is described in EP 0 714 987.

The pharmaceutical protein preparation may be used at dosages of between 30-100 IU/kg (One I.U is 100 ng/ml) at as single daily injection or up to 3 times/day for several days. Patients may be treated immediately upon presentation at the clinic with a bleed. Alternatively, patients may receive a bolus infusion every eight to twelve hours, or if sufficient improvement is observed, a once daily infusion of the variant FVIII described herein.

The invention also provides compositions, such as compositions including Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), and functional fragments of either, having one or more of the following attributes: 1) exhibits increased expression by cells or in animals; 2) exhibits increased secretion by cells; 3) exhibits increased activity, as reflected by increased clotting, for example; 4) exhibits increased stability; and 5) exhibits increased packaging by AAV vector.

Accordingly, invention nucleic acids, vectors, recombinant vectors (e.g., rAAV), and recombinant virus particles and other compositions, agents, drugs, biologics (proteins) can be incorporated into pharmaceutical compositions. Such pharmaceutical compositions are useful for, among other things, administration and delivery to a subject in vivo or ex vivo.

In particular embodiments, pharmaceutical compositions also contain a pharmaceutically acceptable carrier or excipient. Such excipients include arty pharmaceutical agent that does not itself induce an immune response harmful to the individual receiving the composition, and which may be administered without undue toxicity.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nucleic acid, vector, viral particle or protein to a subject.

Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, a preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran.

Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. For administration of FVIII-containing vectors or polypeptides, such labeling would include amount, frequency, and method of administration.

Pharmaceutical compositions and delivery systems appropriate for the compositions, methods and uses of the invention are known in the art (see, e.g., *Remington: The Science and Practice of Pharmacy* (2003) $20^{th}$ ed., Mack Publishing Co., Easton, Pa.; *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

The invention also provides methods for introducing a Factor VIII (FVIII) encoding nucleic acid variants (e.g., codon optimized variant encoding FVIII), variant FVIII protein encoding nucleic acid variants (e.g., codon optimized nucleic acid variant encoding variant FVIII protein with a PACE/Furin cleavage site mutation, deletion or substitution), and functional fragments of either into a cell or an animal. In a particular embodiment, the invention provides methods for modulating hemostasis. In one embodiment, a method includes contact or administration of an individual (patient or subject such as a mammal) with a nucleic acid delivery vehicle (e.g., an AAV vector) comprising a Factor VIII (FVIII) encoding nucleic acid variant (e.g., codon optimized variant encoding FVIII), or variant FVIII protein encoding nucleic acid variants (e.g., codon optimized nucleic acid variant encoding variant FVIII protein with a PACE/Furin cleavage site mutation, deletion or substitution), or a functional fragment of either, under conditions wherein the FVIII polypeptide is expressed in the individual. In another embodiment, a method includes providing cells of an individual (patient or subject such as a mammal) with a nucleic acid delivery vehicle (e.g., an AAV vector) comprising a Factor VIII (FVIII) encoding nucleic acid variant (e.g., codon optimized variant encoding FVIII), or variant FVIII protein encoding nucleic acid variants (e.g., codon optimized nucleic acid variant encoding variant FVIII protein with a PACE/Furin cleavage site mutation, deletion or substitution), or a functional fragment of either, under conditions wherein the FVIII polypeptide is expressed in the individual.

From the foregoing, it can be seen that Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either, may be used in the treatment of disorders associated with deficient, insufficient or aberrant blood coagulation.

Compositions of Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or functional fragments, of either, including vectors, recombinant vectors (e.g., rAAV), and recombinant virus particles can be administered, and methods and uses of the invention can be provided, in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a rAAV/vector genome dose range to treat a patient having a particular disease or disorder based on the aforementioned factors, as well as other factors. Generally, doses will range from at least $1\times10^8$, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect. AAV dose in the range of $1\times10^{10}$-$1\times10^{11}$ in mice, and $1\times10^{12}$-$1\times10^{13}$ in dogs have been effective.

Using hemophilia B as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed. With respect to treating such a hemophilic subject, a typical dose is at least $1\times10^{10}$ vector genomes (vg) per kilogram (vg/kg) of the weight of the subject, or between about $1\times10^{10}$ to $1\times10^{11}$ vg/kg of the weight of the subject, or between about $1\times10^{11}$ to $1\times10^{12}$ vg/kg of the weight of the subject, or between about $1\times10^{12}$ to $1\times10^{13}$ vg/kg of the weight of the subject, to achieve a desired therapeutic effect.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein (e.g., FVIII) for treatment of a clotting disorder (e.g., hemophilia A).

Accordingly, methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease. For HemA, an effective amount would be an amount that reduces frequency or severity of acute bleeding episodes in a subject, for example, or an amount that reduces clotting time as measured by a clotting assay, for example.

Accordingly, pharmaceutical compositions of the invention include compositions wherein the active ingredients are contained in an effective amount to achieve the intended therapeutic purpose. Determining a therapeutically effective dose is well within the capability of a skilled medical practitioner using the techniques and guidance provided in the invention.

Therapeutic doses will depend on, among other factors, the age and general condition of the subject, the severity of the aberrant blood coagulation phenotype, and the strength of the control sequences regulating the expression levels of Factor VIII (FVIII) encoding nucleic acid variants (e.g., codon optimized variants encoding FVIII), variant FVIII protein encoding nucleic acid variants (e.g., codon optimized nucleic acid variants encoding variant FVIII protein with a PACE/Furin cleavage site mutation, deletion or substitution), or a functional fragment of either. Thus, a therapeutically effective amount in humans will fall in a relatively broad range that may be determined by a medical practitioner based on the response of an individual patient to vector-based FVIII treatment.

Compositions such as pharmaceutical compositions may be delivered to a subject, so as to allow production of a biologically active protein (e.g., Factor VIII (FVIII) encoded by nucleic acid variants such as codon optimized variants encoding FVIII, or variant FVIII protein encoded by nucleic acid variants such as codon optimized nucleic acid variants encoding variant FVIII protein with a PACE/Furin cleavage site mutation, deletion or substitution, or a functional fragment of either) or by inducing continuous expression of the FVIII transgene in vivo by gene- and or cell-based therapies or by ex-vivo modification of the patient's or donor's cells. In a particular embodiment, pharmaceutical compositions comprising sufficient genetic material to enable a recipient to produce a therapeutically effective amount of a FVIII polypeptide can influence hemostasis in the subject. Alternatively, as disclosed herein, an effective amount of a variant Factor VIII polypeptide, such as FVIII with one or more mutations, deletions or substitutions in the intracellular protease cleavage recognition site (PACE/Furin), may be directly infused into a patient in need thereof.

The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

Variant Factor VIII polypeptides, alone or in combination with other agents may be administered or contacted or directly infused into a patient in an appropriate biological carrier as described herein. Expression vectors of the invention comprising FVIII encoding variant nucleic acid sequences, such as codon optimized variants encoding FVIII, or variant FVIII protein encoded by nucleic acid variants such as codon optimized nucleic acid variants encoding variant FVIII protein with a PACE/Furin cleavage site mutation, deletion or substitution, or a functional fragment of either, may be administered to a patient by a variety of means to achieve and optionally maintain for a period of time a prophylactically and/or therapeutically effective level of FVIII polypeptide. One of skill in the art could readily determine specific protocols for using the FVIII encoding expression vectors of the invention for the therapeutic treatment of a particular patient.

Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety. In particular, for example, AAV vectors are employed to deliver Factor VIII (FVIII) encoded by nucleic acid variants such as codon optimized variants encoding FVIII, or variant FVIII protein encoded by nucleic acid variants such as codon optimized nucleic acid variants encoding variant FVIII protein with a PACE/Furin cleavage site mutation, deletion or substitution, or a functional fragment of either, to a patient in need thereof.

Factor VIII (FVIII) encoded by nucleic acid variants such as codon optimized variants encoding FVIII, or variant FVIII protein encoded by nucleic acid variants such as codon optimized nucleic acid variants encoding variant FVIII protein with a PACE/Furin cleavage site mutation, deletion or substitution, or a functional fragment of either delivered by way of AAVvectors of the invention may be administered to a patient by any means known.

Methods and uses of the invention include delivery and administration systemically, regionally or locally, or by any route, for example, by injection or infusion. Delivery of the pharmaceutical compositions in vivo may generally be accomplished via injection using a conventional syringe, although other delivery methods such as convection-enhanced delivery are envisioned (See e.g., U.S. Pat. No. 5,720,720). For example, compositions may be delivered subcutaneously, epidermally, intradermally, intrathecally, intraorbitally, intramucosally, intraperitoneally, intravenously, intra-pleurally, intraarterially, orally, intrahepatically, via the portal vein, or intramuscularly. Other modes of administration include oral and pulmonary administration, suppositories, and transdermal applications. A clinician specializing in the treatment of patients with blood coagulation disorders may determine the optimal route for administration of the adenoviral-associated vectors comprising FVIII nucleic acid sequences based on a number of criteria, including, but not limited to: the condition of the patient and the purpose of the treatment (e.g., enhanced or reduced blood coagulation).

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease such as HemA.

The compound, agent, drug, treatment or other therapeutic regimen or protocol can be administered as a combination composition, or administered separately, such as concurrently or in series or sequentially (prior to or following) delivery or administration of a nucleic acid, vector, recombinant vector (e.g., rAAV), or recombinant virus particle. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector, recombinant vector (e.g., rAAV), or recombinant virus particle of the invention, to a subject.

The invention is useful in animals including human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases such as HemA and others known to those of skill in the art.

Subjects appropriate for treatment in accordance with the invention include those having or at risk of producing an insufficient amount or having a deficiency in a functional gene product (e.g., FVIII protein), or produce an aberrant, partially functional or non-functional gene product (e.g., FVIII protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects having aberrant, insufficient or absent blood clotting factor production, such as hemophiliacs (e.g., hemophilia A).

Subjects appropriate for treatment in accordance with the invention also include those having or at risk of producing antibodies against AAV. AAV vectors can be administered or delivered to such subjects using several techniques. For example, empty capsid AAV (i.e., AAV lacking a FVIII nucleic acid) can be delivered to bind to the AAV antibodies in the subject thereby allowing the AAV vector bearing the FVIII nucleic acid to transform cells of the subject. Amounts of empty capsid AAV to administer can be calibrated based upon the amount of AAV antibodies produced in a particular subject. Empty capsid can be of any AAV serotype, for example, AAV1, AAV2, AAV3, AAV4, AAV5, AAV6, AAV7, AAV8, AAV9, AAV10, AAV11, AAV12, Rh10, Rh74 or AAV-2i8.

Alternatively or in addition to, AAV vector can be delivered by direct intramuscular injection (e.g., one or more slow-twitch fibers of a muscle). In another alternative, a catheter introduced into the femoral artery can be used to delivery AAV vectors to liver via the hepatic artery. Non-surgical means can also be employed, such as endoscopic retrograde cholangiopancreatography (ERCP), to deliver AAV vectors directly to the liver, thereby bypassing the bloodstream and AAV antibodies. Other ductal systems, such as the ducts of the submandibular gland, can also be used as portals for delivering AAV vectors into a subject that develops or has preexisting anti-AAV antibodies.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (e.g., FVIII protein), or that produce an aberrant, partially functional or non-functional gene product (e.g., FVIII protein).

Administration or in vivo delivery to a subject in accordance with the methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, recombinant virus particles, and pharmaceutical compositions thereof can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, virus (e.g., AAV) vector, or virus particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features (e.g., nucleic acid variant, vector, plasmid, recombinant vector (e.g., rAAV) sequence, or recombinant virus particle) are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such viruses/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

Hemophilia A (HA) is an X-linked bleeding disease characterized by deficiency in factor VIII (FVIII), a key component of the coagulation cascade (Kazazian, H. H., et al. Hemophilia A: Deficiency of coagulation factor VIII. in The Metabolic and Molecular Bases of Inherited Disease (eds. Scriver, C. R., Beaudet, A. L., Sly, W. S. & Valle, D.) 4367-4392 (McCraw-Hill, New York, 2001). The FVIII gene contains 26 exons that span 186 kb and is synthesized as a large precursor molecule (2332 amino acids) (FIG. 1) (Kaufman, R. J., et al., The biology and genetics of factor VIII deficiency in hemophilia A. in *Hemostasis and Thrombosis: Basic principles and clinical practice* (eds. Colman, R. W., Hirsch, J., Mander, V. J., Clowes, A. W. & George, J. N.) (Lippincott-Raven, Philadelphia, 1998).

Affected individuals commonly suffer joint, muscle, as well as intracranial and intraperitoneal hemorrhages that can be lethal. The normal plasma FVIII level is 100-200 ng/ml, but small amounts of circulating FVIII (~1-2 ng/ml) are sufficient to have a substantial effect on the clinical course of patients with severe disease. The current treatment for HA patients is protein replacement therapy using recombinant or plasma-derived FVIII. However, these products are only available to ~20% of the HA population worldwide. The major complication of this therapy is the development of neutralizing antibodies (inhibitors) to FVIII that occurs in 25-30% of patients with severe HA. Since inhibitors render the FVIII protein therapy ineffective, bypass agents (FVIIa) are used to achieve hemostasis, however, these products are very expensive alternatives.

Disclosed herein are gene constructs for use in gene therapy methods to treat hemophilia. In addition, these factor VIII (FVIII) gene constructs may be useful in vitro in the setting of protein expression systems. Each gene construct can optionally include one or more of a expression control (e.g., promoter) element, factor VIII gene and other regulatory features required for expression of the gene, such as introns, ITRs, stop codons, poly A signals, etc.

Example 2

Codon-Optimization of the Factor VIII DNA Sequence

It has previously been described that codon-optimization of the DNA sequence can improve factor VIII expression in the setting of gene therapy (Ward et al. 2011, Blood 117(3): 798-807). Codon-optimization of a DNA sequence is based on the fact that each DNA codon is a series of three nucleotides that encodes for a specific amino acid residue in the protein chain during the protein synthesis. There are 64 different codons but only 20 amino acids thus there are many codons that can code for the same amino acid. There is codon usage bias observed among different species that reflects a selection process for optimizing the translation process. Importantly, while the DNA sequence is modified in codon optimization, the protein sequence is identical to the wild type sequence.

Codon optimization was performed for the B-domain deleted factor VIII (hFVIII-SQ) cDNA sequence. Four different codon optimized versions of the factor VIII cDNA were assessed in expression assays and surprisingly, several of the DNA sequences expressed higher levels of factor VIII.

One of the sequences not only expressed higher levels of factor VIII but also had a unique feature (SEQ ID NO:1). This sequence could be packaged into an adeno-associated viral (AAV) vector better than the other codon optimized sequences or the wild type sequence. That is, the factor VIII gene, along with its regulatory elements, are flanked by inverted terminal repeats (ITRs) that provide the signal required to package the sequence into the AAV viral capsid. Data suggests that the size of the DNA sequence between the ITRs must be similar to the size of the normal virus genome (4.7 Kb) for optimal packaging efficiency. In the case of factor VIII, we have gene sequences that are 5.0 Kb in length but still appear to be able to be packaged, however, it may not be efficiently packaged as a complete gene.

Figure 4A:
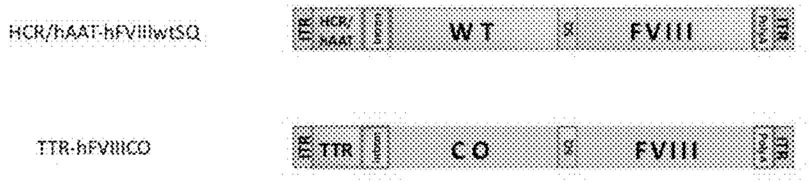
FIG. 4A shows human wild-type and codon optimized FVIII transgene constructs. TTR promoter drives expression of codon-optimized FVIII. SQ, the B-domain deleted form that has a S743 and Q1638 at the junction; ITR, inverted terminal repeat sequences required for packaging of the transgene into the AAV vectors.
Figure 6A:
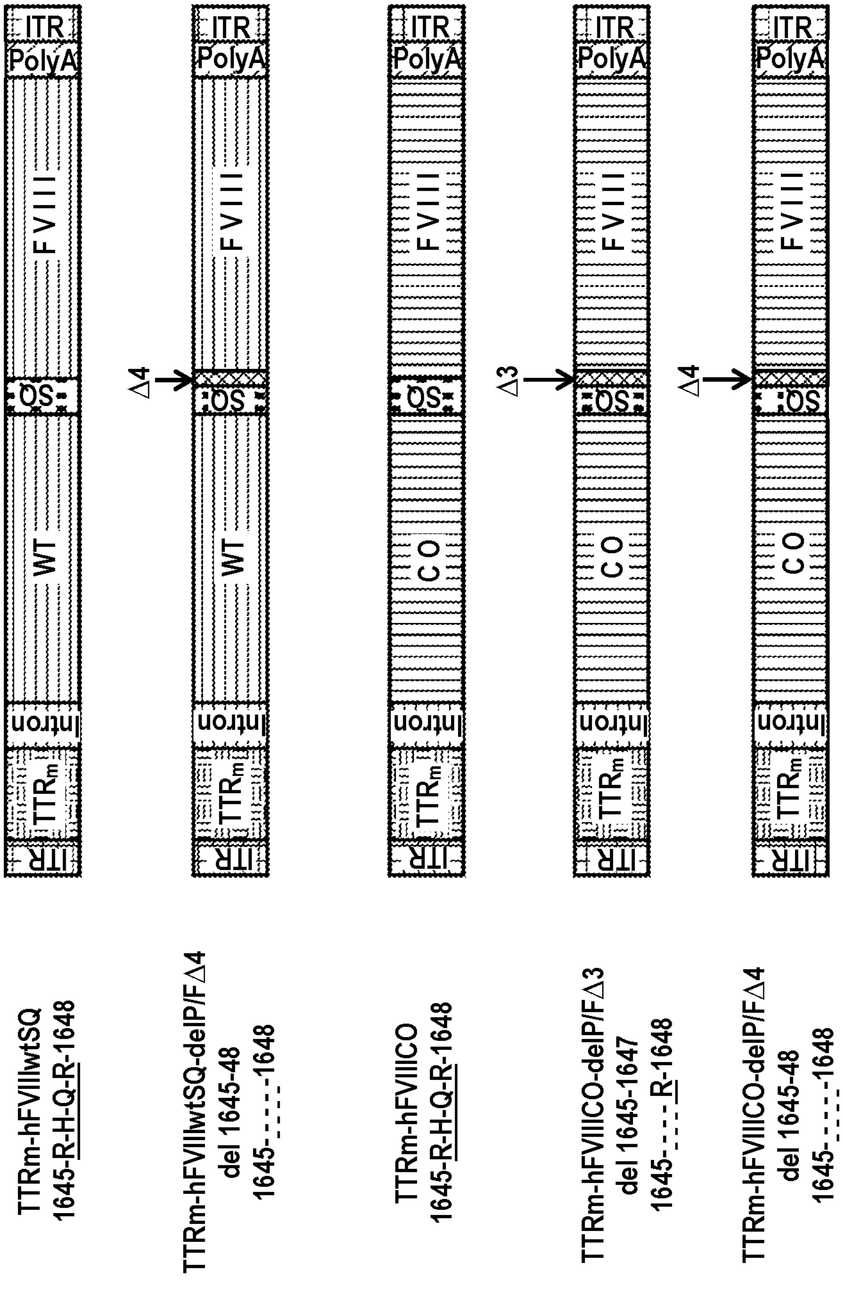
FIG. 6A shows human FVIII transgene constructs. The transgene constructs utilize a modified transthyretin promoter (TTRm), synthetic intron (Intron), and polyadenylation signal (Poly A). The factor VIII transgenes are the wild type B-domain deleted human factor VIII cDNA (WT FVIII) or the codon-optimized B-domain deleted human factor VIII cDNA (CO FVIII). The PACE-furin deletion variants Δ3 or Δ4 were introduced into the hFVIII transgenes. Δ3, deletion of three residues (amino acid 1645-1647) of the PACE-furin cleavage recognition site. Δ4, deletion of four residues (amino acid 1645-1648) of the PACE-furin cleavage recognition site. SQ, the B-domain deleted form that has a S743 and Q1638 at the junction; ITR, inverted terminal repeat sequences required for packaging of the transgene into the AAV vectors.

Another factor that may contribute to the ability to package a particular gene is the DNA sequence itself. Some DNA sequences may be more prone to rearrangements, or may have folding structures based on charge, that affect the ability to package into the viral capsid. That is, it appears that not only the size but also the DNA sequence affects the packaging ability of a transgene construct. In our studies we identified novel factor VIII DNA sequences that do not occur in nature that express higher levels of factor VIII (see, e.g., FIGS. 2, 4A and 6A) but also are packaged more efficiently into the AAV vector. This improved packaging feature generates higher vector yields (Tables 3-5) across serotypes and will allow production of homogenous AAV vector that meets stringent quality control criteria for use in human gene therapy.

To further improve expression levels, codon-optimized human FVIII cDNA constructs were generated with a transthyretin (TTR) or mutant TTR promoter (see description below) and a variant of factor VIII that deletes the PACE-furin cleavage recognition site from amino acid position 1645-1648 (TTRmut-hFVIII-SQ-CO-delP/F) (see description of FVIII variants below). These FVIII transgene constructs were packaged into adeno-associated viral (AAV) vectors and delivered to hemophilia A/CD4 knockout mice. The levels of the FVIII expression were higher than the expression from the wild type hFVIII-SQ as follows: TTR-hFVIII-SQ-CO was 5-fold higher, TTRmut-hFVIII-SQ-CO was 16-fold higher and TTRmut-hFVIII-SQ-CO-delP/F was 33-fold higher.

Example 3

Variants of Factor VIII

Modifications were introduced into the protein sequence of factor VIII. The modifications introduced into the codon optimized DNA sequence changes a PACE-furin cleavage recognition site. Modification of this site improves the stability and biological activity of the protein. The amino acid modifications introduced into a codon-optimized factor VIII of PACE-furin cleavage recognition site are shown in Table 1.

Deletion variants of the PACE-furin (P/F) cleavage recognition site at amino acid position 1645-1648 were introduced into the wild type B-domain deleted human factor VIII (hFVIII) gene. Stable baby hamster kidney (BHK) cells lines were generated that expressed each variant and recombinant protein was purified for analysis.

cFVIII, canine factor VIII; hFVIII-RH, a variant that has a single amino acid substitution at amino acid position 1645 from an arginine (R) to a histidine (H) which generates a P/F site that is identical to the cFVIII sequence; Δ1645, deletion of residue R1645, Δ2, deletion of residues R1645 and H1646; Δ3, deletion of residues R1645, H1646 and Q1647; Δ4, deletion of residues R1645, H1646, Q1647 and R1648; and Δ1648, deletion of residue R1648.

TABLE 1

Human Factor VIII variants of the PACE-Furin recognition site

| | Amino acids at PACE furin recognition site | | | | | | |
|---|---|---|---|---|---|---|---|
| hFVIII Variant | 1642 | 1643 | 1644 | 1645 | 1646 | 1647 | 1648 |
| hFVIII | V | L | K | R | H | Q | R |
| hFVIII-RH | V | L | K | H | H | Q | R |
| Δ4: hFVIII-del1645-1648 | V | L | K | | | | |
| Δ1645: hFVIII-del1645 | V | L | K | | H | Q | R |
| Δ2: hFVIII-del1645-1646 | V | L | K | | | Q | R |
| Δ3: hFVIII-del1645-1647 | V | L | K | | | | R |
| Δ1648: hFVIII-del1648 | V | L | K | R | H | Q | — |

Recombinant variant proteins were purified and have been compared in different assays both in vitro and in vivo to characterize procoagulant function. In vitro the P/F variants have higher biological activity than wild type hFVIII with the Δ3 having the highest biological activity followed by the Δ4 and Δ2 variants.

In vivo, all of these variant hFVIII proteins were infused into hemophilia A mice in a tail clip challenge assay to measure blood loss after an injury. The Δ3 and Δ4 variants showed improved ability to reduce blood loss in this challenge model.

Figure 3A:
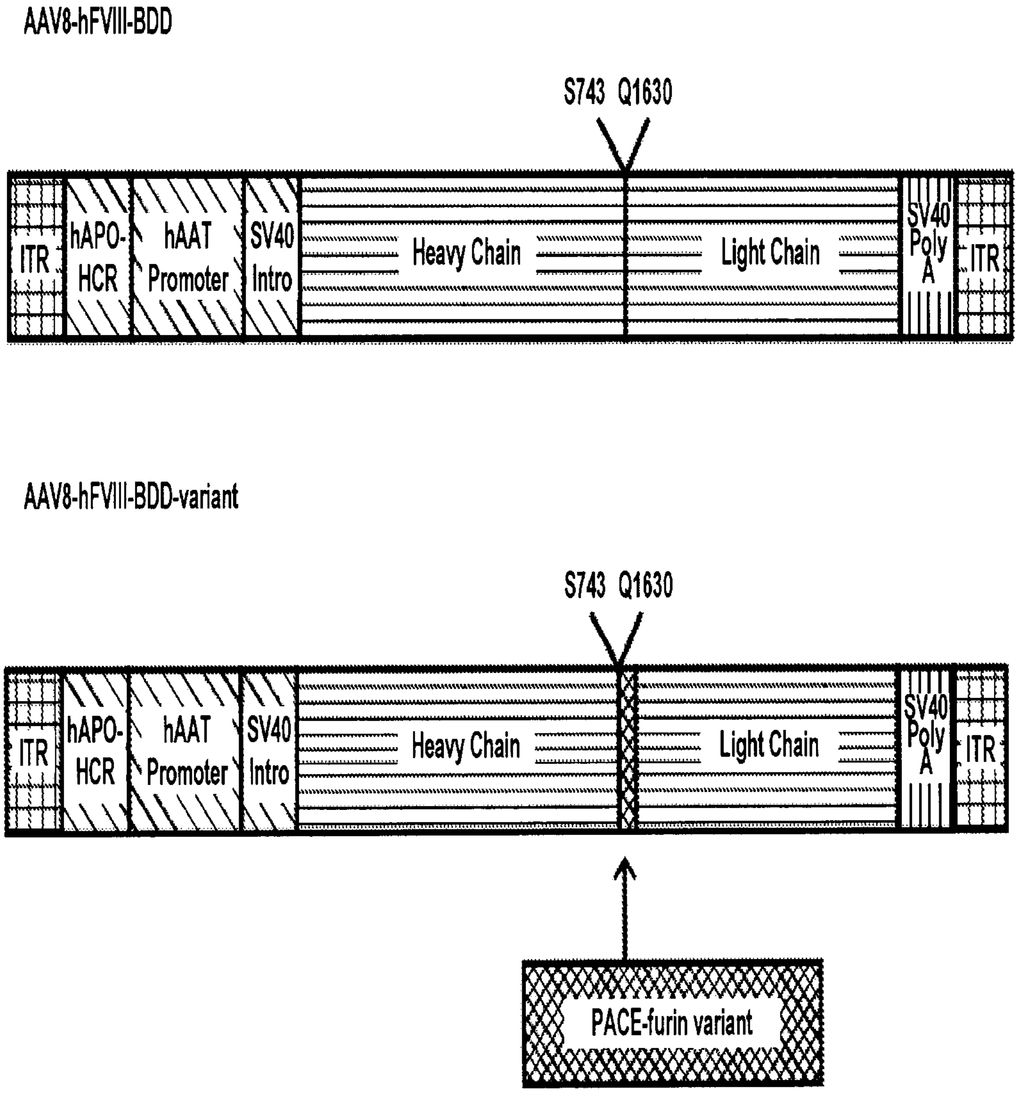
FIG. 3A shows non-codon optimized AAV-hFVIII constructs. The AAV-hFVIII vectors have the wild type B-domain deleted (BDD) human factor VIII cDNA. The enhancer/promoter element is a minimal hepatic control region-human α-1 antitrypsin enhancer/promoter (HCR-hAAT) that has a shortened version of the hepatic control region of the human apolprotein ExxC-1 gene locus (Nathwani, et al. 2006, Sabatino et al. 2011). A 65-bp SV40 intron and a 134-bp SV40 polyadenylation are also included. The only difference between these constructs is that one utilizes the wild type hFVIII-BDD (top construct) and the other utilizes the wild type hFVIII-BDD with a PACE-furin deletion variant (bottom construct). All five P/F deletion variants (Table 1) were introduced into this expression cassette.
Figure 3B:
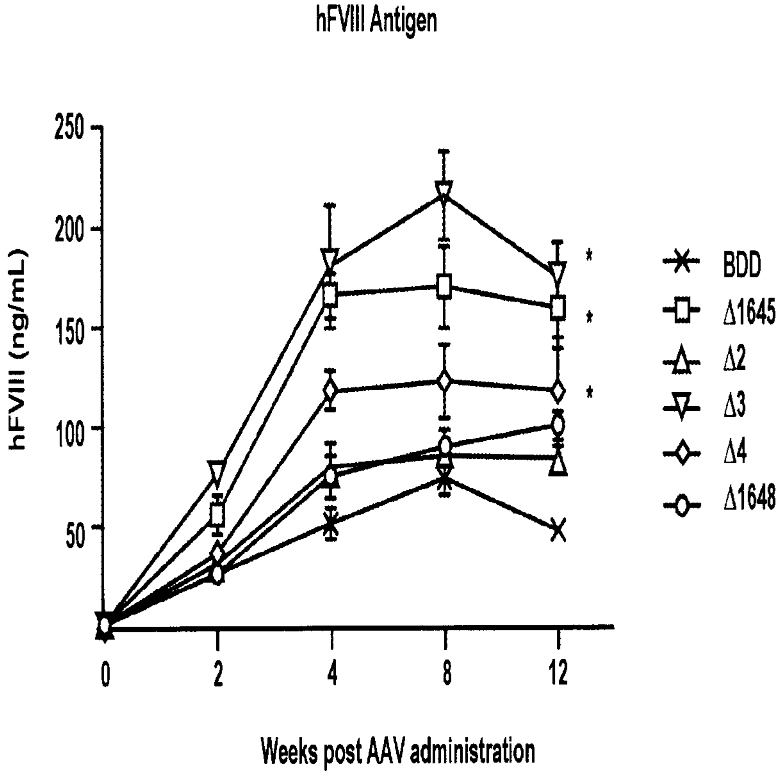
FIG. 3B shows FVIII expression after AAV8 delivery of hFVIII PACE-furin deletion variants. AAV ($5\times10^{11}$ vg/mouse) was delivered to hemophilia A/CD4 knockout (immunodeficient) mice. The hFVIII expression (antigen and activity) was followed in the plasma through 12 weeks after AAV administration. *=$p<0.05$

All five of the P/F deletion variants were introduced into an adeno-associated viral (AAV) vector expression cassette containing the wild type factor VIII gene (FIG. 3A). AAV-hFVIII was delivered to hemophilia A/CD4KO mice ($5\times10^{11}$ vg/mouse) and expression of FVIII was determined by antigen and activity (FIG. 3B). The expression levels of Δ3 were 4-fold higher than wild type FVIII-BDD while M and Δ1645 were two and three-fold higher, respectively. The Δ2 and Δ1648 were similar to wild type FVIII. These results support the introduction of the Δ3 and Δ4 PACE-furin deletion variants into the improved codon-optimized FVIII constructs.

TABLE 2A shows hFVIII Sequence Identities between WT hFVIII and 3 Codon Optimized Variants, denoted CO1, CO2 and CO3 hFVIII 4374 nucleotides

| Sequence 1 | Sequence 2 | % Identity | # NT Identities | # NT Differences |
|---|---|---|---|---|
| WT | CO3 | 77.34% | 3386 | 992 |
| WT | CO1 | 77.14% | 3374 | 1000 |
| WT | CO2 | 75.74% | 3315 | 1062 |
| CO3 | CO1 | 82.20% | 3597 | 779 |
| CO3 | CO2 | 81.91% | 3590 | 793 |

TABLE 2B shows nucleotide frequencies for each codon optimized hFVIII variant denoted CO1, CO2 and CO3

| | WT hFVIII | CO3 | CO2 | CO1 |
|---|---|---|---|---|
| | Nucleotide Frequency | | | |
| | Frequency, % | Frequency, % | Frequency, % | Frequency, % |
| A | A: 1,266 28.9% | A: 1,145 26.2% | A: 1,072 24.5% | A: 1,063 24.3% |
| C | C: 970 22.2% | C: 1,108 25.3% | C: 1,197 27.4% | C: 1,371 31.3% |
| G | G: 964 22.0% | G: 1,133 25.9% | G: 1,149 26.3% | G: 1,191 27.2% |
| T | T: 1,174 26.8% | T: 988 22.6% | T: 956 21.9% | T: 749 17.1% |
| GC | GC: 1,934 44.2% | GC: 2,241 51.2% | GC: 2,346 53.6% | GC: 2,562 58.6% |

Example 4

TTR Promoter

The improved promoter element that utilized in these studies is the transthyretin (TTR) promoter with four nucleotide changes that improves factor VIII expression. The characterization of this promoter was originally described in Costa and Grayson 1991, Nucleic Acids Research 19(15): 4139-4145. These in vitro studies suggested that a modification of four nucleotides increases the affinity of the hepatocyte nuclear factor (HNF) transcription factor for its binding site in the DNA sequence. Thus, in a novel synthetic promoter, we introduced the four nucleotide changes beginning at nucleotide 67 of the TTR promoter sequence that is not known to occur in nature. It was modified from TAmGTGTAG to TATTGACTTAG (SEQ ID NO:8).

Example 5

Comparison of Wild Type and Codon-Optimized (CO) Transgenes

AAV transgene constructs were generated to demonstrate the contribution of each FVIII sequence or sequence variant to the improved FVIII expression. These constructs contain the same regulatory elements as the construct described in FIG. 2; however, their FVIII sequence is different. Based on the studies described above, the best performing PACE-furin deletion variants (Δ3 and Δ4) were introduced into these hFVIII transgenes. Also, all of these FVIII transgenes are a B-domain deleted (BDD) form. All of AAV vectors in this study were produced at the Research Vector Core at CCMT and were titered side by side by quantitative PCR and silver staining.

Figure 6B:
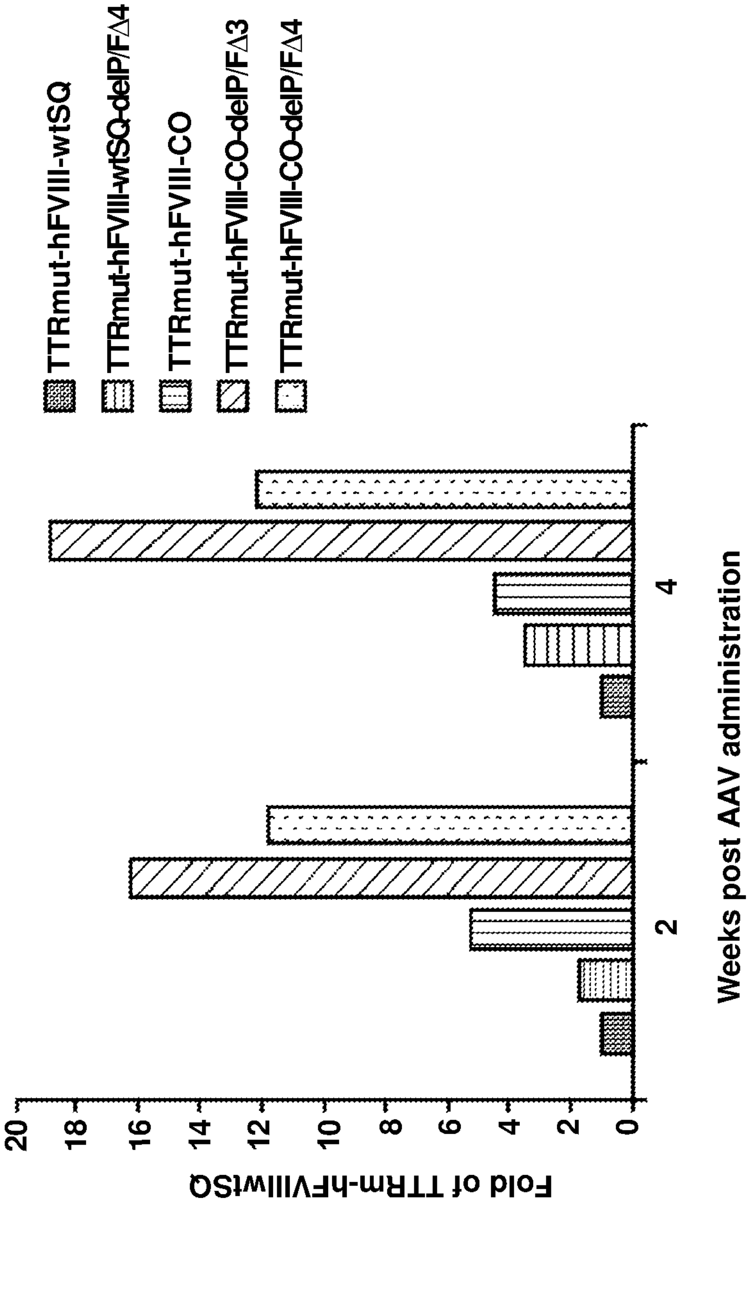
FIG. 6B shows Factor VIII expression after AAV delivery of wild type and codon-optimized FVIII constructs. The hFVIII antigen levels were determined by a human FVIII specific ELISA (Affinity Biologicals). FVIII activity determined by Coatest assay correlated with the FVIII antigen levels. These data are presented as fold difference compared to the TTRmut-hFVIII-wtSQ at the 2 and 4 week time points.

In this study, the five human FVIII transgenes were: (1) wild type human FVIII-BDD (hFVIIIwtSQ); (2) wild type human FVIII-BDD with the deletion of four residues in the PACE-furin recognition sequence (hFVIIIwtSQΔ4); (3) codon-optimized (CO) hFVIII-BDD (hFVIIICO); (4) codon-optimized with deletion of three residues of the PACE-furin recognition site (hFVIIICOΔ3); and (5) codon-optimized hFVIII with deletion of four residues of the PACE-furin recognition site (hFVIIICOΔ4)(FIG. 6).

Figure 4B:
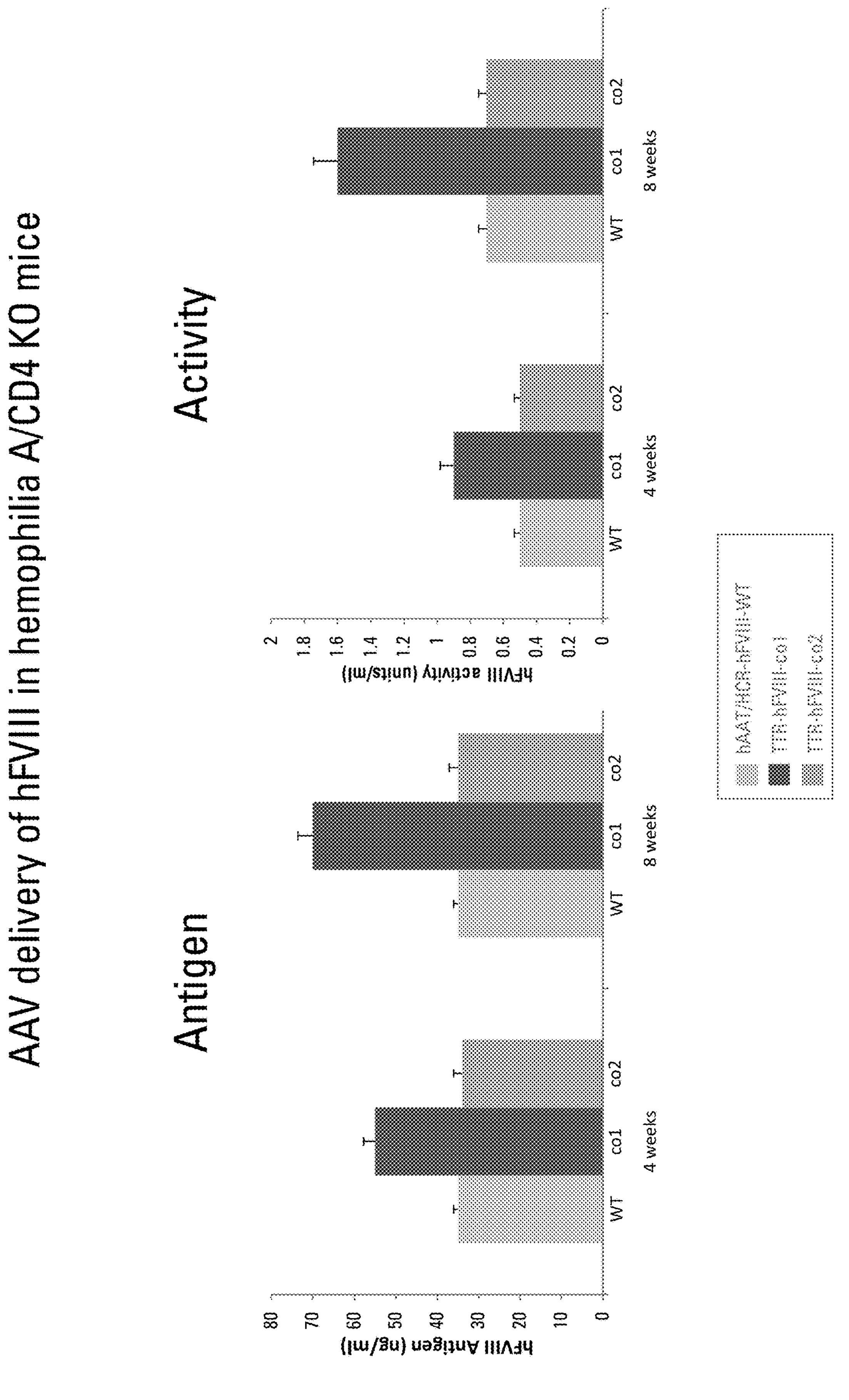
FIG. 4B shows that codon optimization of hFVIII leads to higher expression levels. A comparison of CO1 FVIII, CO2 FVIII, and wild-type FVIII AAV delivered FVIII expression and activity levels at 4 and 8 weeks post AAV vector administration.
Figure 4C:
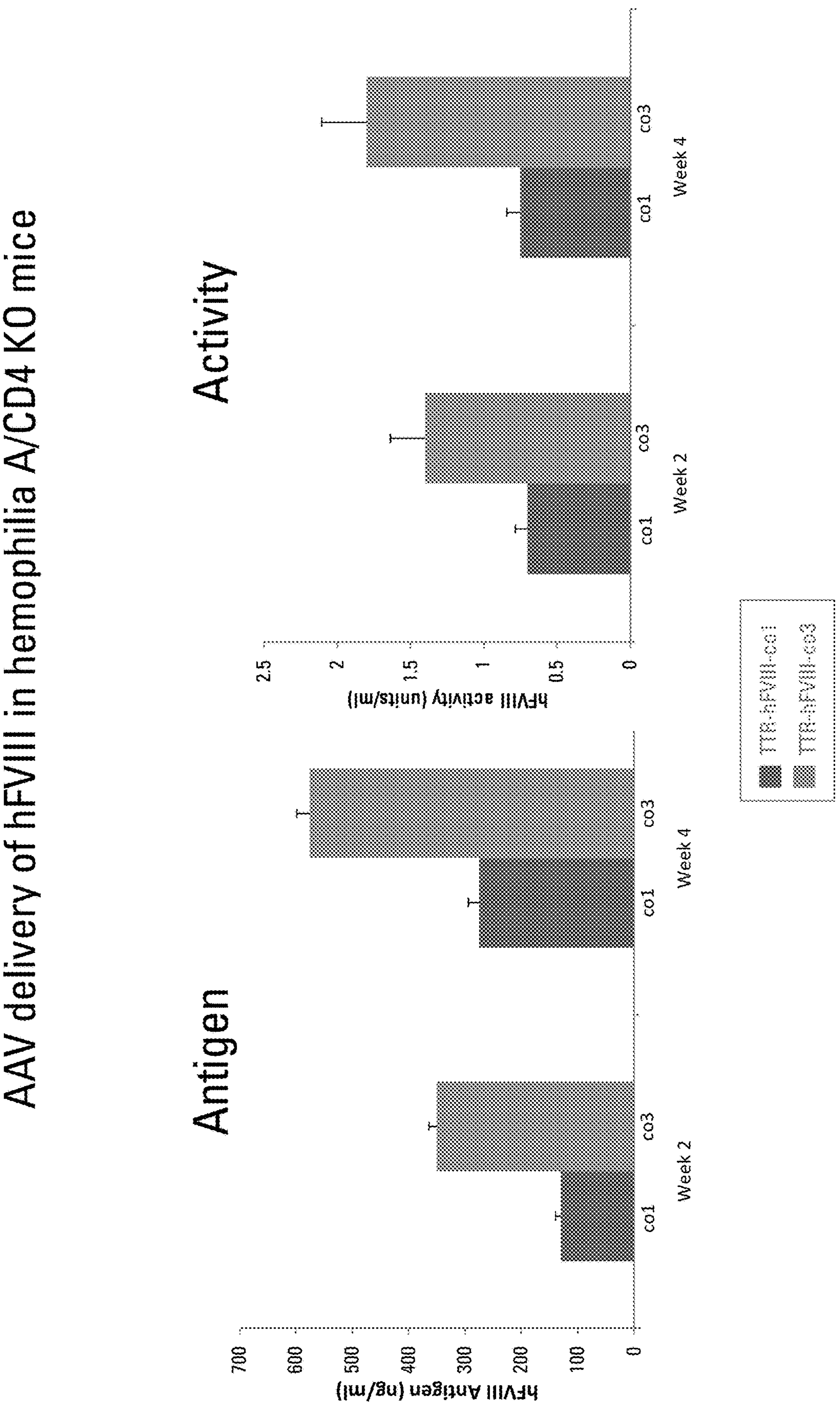
FIG. 4C shows that codon optimization of hFVIII leads to higher expression levels. A comparison of CO1 FVIII, CO3/C0 FVIII, and wild-type FVIII AAV delivered FVIII expression and activity levels at 4 and 8 weeks post AAV vector administration.
Figure 5A:
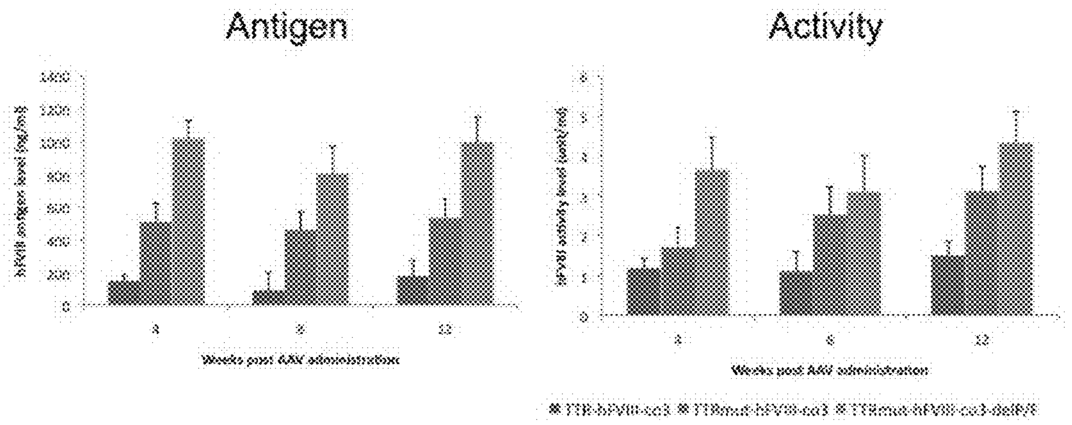
FIG. 5A shows FVIII expression after AAV delivery of CO3. Comparison of the TTR promoter and the TTR mutant (TTRm) promoter with FVIII-CO3. The TTR mutant promoter with the PACE-furin deletion Δ4 (delP/F) introduced into CO3.
Figure 5B:
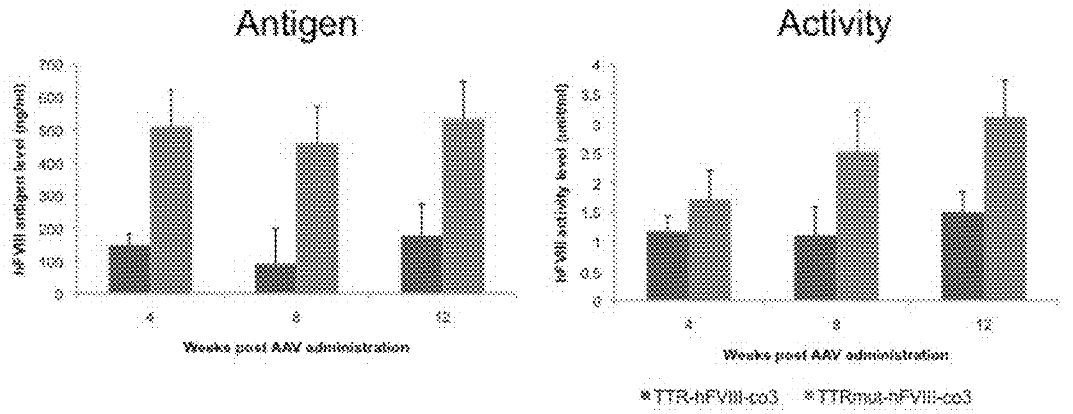
FIG. 5B shows data indicating that the TTR mutant promoter results in increased FVIII-CO3 expression after AAV delivery.

This data is an improvement of the data in FIG. 2, in which the wild type FVIII construct used a different promoter (HCR-hAAT) and was not in the same expression cassette as the codon optimized (CO) constructs making it difficult to demonstrate the individual contribution of each FVIII transgene. In addition, the wild type FVIII with the PACE/furin variant that deletes four amino acid residues at this site (hFVIIIwtSQΔ4) is included to demonstrate the contribution of the PACE-furin deletion in the context of the wild type hFVIII (FIG. 4).

As described, AAV-hFVIII was delivered to hemophilia A/CD4KO mice ($1\times10^{11}$vg/mouse). However, a different AAV serotype that was developed based upon an AAV variant, denoted Rh74vv. Previous data was generated with AAV serotype 8 (AAV8).

The hFVIII expression was measured by antigen levels (ELISA) as well as activity (Coatest assay). For Rh74vv, levels of hFVIII expression at 4 weeks post vector administration were 9.4+1.5 ng/ml (6.3% of normal FVIII levels) for (hFVIIIwtSQ), 32.4+13.0 ng/ml (21.6%) for (hFVIIIwtSQΔ4), 42.2+7.1 ng/ml (28.1%) (hFVIIICO), 177.8+8.5 ng/ml (118.5%) (hFVIIICOΔ3) and 114.3+60.2 ng/ml (76.2%) (hFVIIICOΔ4) (FIG. 6).

Figure 7:
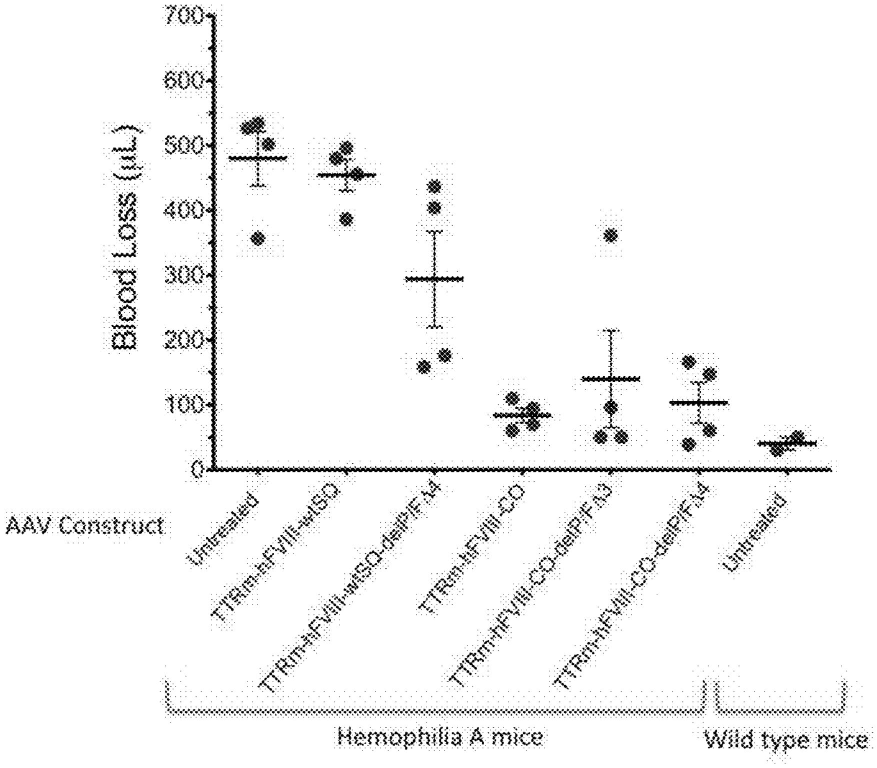
FIG. 7 shows in vivo hemostatic challenge of mice after AAV delivery of wild type and codon-optimized hFVIII constructs. At 6 weeks post vector administration ($1\times10^{11}$ vg/mouse), the mice treated with AAV-hFVIII constructs were challenged using a tail clip assay (Ivanciu L et al. Nature Biotech 2011, 29(11):1028-1033). Mice were anesthesized with isoflurane and the tail was pre-warmed to 37° C. followed by tail transection at a diameter of 3 mm. Blood was collected for 10 minutes in 14 ml of saline at 37° C. Total blood loss (μl) was determined by measuring total hemoglobin by absorbance at 575 nm following red cell lysis. Blood loss of the hemophilia A mice that were treated with AAV-hFVIII constructs was compared to the blood loss from untreated hemophilia A mice and wild type mice.

At 6 weeks post vector administration, mice after AAV delivery of wild type and codon-optimized hFVIII constructs were assayed by in vivo hemostatic challenge. The results (FIG. 7) show that clotting activity in the hemophilia A mice, as reflected by reduced blood loss, is greater for the CO optimized FVIII with or without the P/F deletions, and is comparable to wild type mice.

Since the levels of FVIII protein expression obtained with the AAV variant (Rh74vv) are lower than the FVIII levels with AAV8, the data is presented using fold difference compared to the wild type FVIII construct. Importantly, the overall conclusions are the same. Levels of expression with the introduction of the M P/F variant is about 2-4 fold higher compared to the wild type sequence alone. The CO transgene results in expression that is 5-fold higher than the wild type hFVIII (hFVIII-wtSQ). The introduction of the P/F deletion variants into the codon-optimized hFVIII (hFVIII-CO) results in expression that is 3-4 fold higher (Δ3) or 2-3 fold higher (M) than the CO transgene alone. Thus, the hFVIIICOΔ3 construct is 16-19-fold better than hFVIIIwtSQ, which is substantially higher than either the P/F deletion variants or codon optimization alone.

Significantly, the contribution of the P/F deletion variants is consistent with both the wild type and the codon-optimized hFVIII sequences (FIG. 4). Furthermore, this contribution was also observed using another expression cassette (FIG. 3). That is, the Δ3 P/F variant results in 3-4 fold higher expression levels and Δ4 results in 2-3 fold higher expression levels regardless of whether they are in the wild type DNA sequence or the codon-optimized DNA sequence. Although not wishing to be bound by any particular theory, the combined synergistic effect is believed due to the different mechanisms that are responsible for the codon-optimization (improved translation of the RNA sequence) and the PACE-furin variants (improved secretion and higher biological activity of the protein).

As disclosed (FIG. 2), the TTRm promoter increases expression 2-fold compared to the TTR promoter alone. While not included in this study, a reasonable estimate based on the other studies is that the optimized construct—TTRm-hFVIIICOΔ3 is ~30-40-fold better than TTR-hFVIIIwtSQ.

Example 6

Vector Yields of Codon-Optimized and Non-Codon Optimized Constructs

Adeno-associated viral (AAV) vector yields for human factor VIII preparations are shown in Tables 3-5. The adeno-associated viral (AAV) vector genomes per roller bottle for wild type human FVIII-SQ (hFVIII) (3 preparations, denoted Prep1-Prep3) and the codon-optimized human FVIII (hFVIII-CO, also referred to as CO3) (5 separate preparations of CO3, denoted Prep1-Prep5) are shown. All vector preparations of FVIII-CO3 were made using the same production protocol and purification scheme. The average yield of AAV8-hFVIII-SQ-CO was $4.60\times10^{12}$ vg/rollerbottle (13 vector preparations) compared to the average yield of the AAV8-hFVIII-SQ of $2.77\times10^{12}$ vg/rollerbottle (3 vector preparations). The yields are 2-fold higher with the CO FVIII sequence compared to the wild type FVIII sequence.

TABLE 3

AAV-8 vector yields for human factor VIII preparations

| hFVII Transgene | AAV Vector | Vector Genomes/ Roller Bottle |
|---|---|---|
| hFIX | AAV8-hFIX-19 | $1.00 \times 10^{13}$ |
| Wild type | AAV8-hFVIII-Prep 1 | $2.20 \times 10^{12}$ |
| | AAV8-hFVI III-Prep 2 | $3.66 \times 10^{12}$ |
| | AAV8-hFVIII-Prep 3 | $2.46 \times 10^{12}$ |
| Codon | AAV8-hFVIII-CO-Prep 1 | $4.54 \times 10^{12}$ |
| Optimized | AAV8-hFVIII-CO-Prep 2 | $3.62 \times 10^{12}$ |
| | AAV8-hFVIII-CO-Prep 3 | $4.71 \times 10^{12}$ |
| | AAV8-hFVIII-CO-Prep 4 | $5.00 \times 10^{12}$ |
| | AAV8-hFVIII-CO-Prep 5 | $4.30 \times 10^{12}$ |

The mean yield of all vector preparations of FVIII with the standard deviation are shown in Tables 4 and 5. Again, while AAV preparations produced by a different vector core were observed to have a lower yield, a comparison of both the wild type vectors and the CO vectors in a different serotype (Rh74vv) shows that the yields are consistently 2-fold higher. This demonstrates that yield of FVIII vector preparations is independent of the vector core and the AAV serotype.

TABLE 4

AAV-8 vector yields for human factor VIII preparations with standard deviation

| hFVIII Transgene | AAV Vector | Number of Preparations | Mean Vector Genomes/ Roller Bottle |
|---|---|---|---|
| hFIX | AAV8-hFIX-19 | | $1.00 \times 10^{13}$ |
| Wild type | AAV8-hFVIII | 3 | $2.67 \times 10^{12} \pm 9.29 \times 10^{11}$ |
| Codon Optimized | AAV8-hFVIII-CO | 13 | $4.60 \times 10^{12} \pm 6.85 \times 10^{11}$ |

TABLE 5

Rh74vv AAV vector yields for human factor VIII preparations with standard deviation

| hFVIII Transgene | AAV Vector | Number of Preparations | Mean Vector Genomes/ Roller Bottle |
|---|---|---|---|
| Wild type | Rh74vv hFVIII | 7 | $9.58 \times 10^{11} \pm 5.07 \times 10^{11}$ |
| Codon Optimized | Rh74vv hFVIII-CO | 5 | $2.39 \times 10^{12} \pm 6.85 \times 10^{11}$ |

Codon-optimized factor VIII cDNA, aka CO/CO3

(SEQ ID NO: 1)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

-continued

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGAGGCA

CCAGCGCGAGATCACCCGCACTACCCTGCAGAGTGATCAGGAAGAGATCGACTACGACGATACAATTT

CTGTGGAAATGAAGAAAGAGGACTTCGATATCTATGACGAAGATGAGAACCAGAGTCCTCGATCATTC

CAGAAGAAAACCCGGCATTACTTTATTGCTGCAGTGGAGCGCCTGTGGGATTATGGCATGTCCTCTAG

TCCTCACGTGCTGCGAAATCGGGCCCAGTCAGGGAGCGTCCCACAGTTCAAGAAAGTGGTCTTCCAGG

AGTTTACAGACGGATCCTTTACTCAGCCACTGTACCGGGGCGAACTGAACGAGCACCTGGGGCTGCTG

GGACCCTATATCAGAGCTGAAGTGGAGGATAACATTATGGTCACCTTCAGAAATCAGGCATCTAGGCC

TTACAGTTTTTATTCAAGCCTGATCTCTTACGAAGAGGACCAGAGGCAGGGAGCAGAACCACGAAAAA

ACTTCGTGAAGCCTAATGAGACCAAAACATACTTTTGGAAGGTGCAGCACCATATGGCCCCAACAAAA

GACGAATTCGATTGCAAGGCATGGGCCTATTTTTCTGACGTGGATCTGGAGAAGGACGTCCACAGTGG

CCTGATCGGGCCACTGCTGGTGTGTCATACTAACACCCTGAATCCCGCACACGGCAGGCAGGTCACTG

TCCAGGAATTCGCCCTGTTCTTTACCATCTTTGATGAGACAAAAAGCTGGTACTTCACCGAAAACATG

-continued

GAGCGAAATTGCCGGGCTCCATGTAATATTCAGATGGAAGACCCCACATTCAAGGAGAACTACCGCTT

TCATGCCATCAATGGGTATATTATGGATACTCTGCCCGGACTGGTCATGGCTCAGGACCAGAGAATCA

GGTGGTACCTGCTGAGCATGGGGTCCAACGAGAATATCCACTCAATTCATTTCAGCGGACACGTGTTT

ACTGTCCGGAAGAAAGAAGAGTATAAAATGGCCCTGTACAACCTGTATCCCGGCGTGTTCGAAACCGT

CGAGATGCTGCCTAGCAAGGCAGGGATCTGGAGAGTGGAATGCCTGATTGGGGAGCACCTGCATGCCG

GAATGTCTACCCTGTTTCTGGTGTACAGTAATAAGTGTCAGACACCCCTGGGGATGGCTTCCGGACAT

ATCCGGGATTTCCAGATTACCGCATCTGGACAGTACGGCCAGTGGGCCCCTAAGCTGGCTAGACTGCA

CTATTCCGGGTCTATCAACGCTTGGTCCACAAAAGAGCCTTTCTCTTGGATTAAGGTGGACCTGCTGG

CACCAATGATCATTCATGGCATCAAAACTCAGGGGGCCAGGCAGAAGTTCTCCTCTCTGTACATCTCA

CAGTTTATCATCATGTACAGCCTGGATGGCAAGAAATGGCAGACATACCGCGGCAATAGCACAGGGAC

TCTGATGGTGTTCTTTGGCAACGTGGACAGTTCAGGGATCAAGCACAACATTTTCAATCCCCCTATCA

TTGCTAGATACATCAGGCTGCACCCAACCCATTATTCTATTCGAAGTACACTGCGGATGGAACTGATG

GGGTGCGATCTGAACAGTTGTTCAATGCCCCTGGGAATGGAGTCCAAGGCAATCTCTGACGCCCAGAT

TACCGCTAGCTCCTACTTCACTAATATGTTTGCTACCTGGAGCCCCTCCAAAGCACGACTGCATCTGC

AGGGACGAAGCAACGCATGGCGACCACAGGTGAACAATCCCAAGGAGTGGCTGCAGGTCGATTTTCAG

AAAACTATGAAGGTGACCGGAGTCACAACTCAGGGCGTGAAAAGTCTGCTGACCTCAATGTACGTCAA

GGAGTTCCTGATCTCTAGTTCACAGGACGGCCACCAGTGGACACTGTTCTTTCAGAACGGAAAGGTGA

AAGTCTTCCAGGGCAATCAGGATTCCTTTACACCTGTGGTCAACTCTCTGGACCCACCCCTGCTGACT

CGCTACCTGCGAATCCACCCACAGTCCTGGGTGCATCAGATTGCACTGAGAATGGAAGTCCTGGGCTG

CGAGGCCCAGGACCTGTATTGA

Codon-optimized factor VIII cDNA, aka CO/CO3, with R1645H variant
(SEQ ID NO: 2)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

-continued

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGCACCA

CCAGCGCGAGATCACCCGCACTACCCTGCAGAGTGATCAGGAAGAGATCGACTACGACGATACAATTT

CTGTGGAAATGAAGAAAGAGGACTTCGATATCTATGACGAAGATGAGAACCAGAGTCCTCGATCATTC

CAGAAGAAAACCCGGCATTACTTTATTGCTGCAGTGGAGCGCCTGTGGGATTATGGCATGTCCTCTAG

TCCTCACGTGCTGCGAAATCGGGCCCAGTCAGGGAGCGTCCCACAGTTCAAGAAAGTGGTCTTCCAGG

AGTTTACAGACGGATCCTTTACTCAGCCACTGTACCGGGGCGAACTGAACGAGCACCTGGGGCTGCTG

GGACCCTATATCAGAGCTGAAGTGGAGGATAACATTATGGTCACCTTCAGAAATCAGGCATCTAGGCC

TTACAGTTTTTATTCAAGCCTGATCTCTTACGAAGAGGACCAGAGGCAGGGAGCAGAACCACGAAAAA

ACTTCGTGAAGCCTAATGAGACCAAAACATACTTTTGGAAGGTGCAGCACCATATGGCCCCAACAAAA

GACGAATTCGATTGCAAGGCATGGGCCTATTTTTCTGACGTGGATCTGGAGAAGGACGTCCACAGTGG

CCTGATCGGGCCACTGCTGGTGTGTCATACTAACACCCTGAATCCCGCACACGGCAGGCAGGTCACTG

TCCAGGAATTCGCCCTGTTCTTTACCATCTTTGATGAGACAAAAAGCTGGTACTTCACCGAAAACATG

GAGCGAAATTGCCGGGCTCCATGTAATATTCAGATGGAAGACCCCACATTCAAGGAGAACTACCGCTT

TCATGCCATCAATGGGTATATTATGGATACTCTGCCCGGACTGGTCATGGCTCAGGACCAGAGAATCA

GGTGGTACCTGCTGAGCATGGGGTCCAACGAGAATATCCACTCAATTCATTTCAGCGGACACGTGTTT

ACTGTCCGGAAGAAAGAAGAGTATAAAATGGCCCTGTACAACCTGTATCCCGGCGTGTTCGAAACCGT

CGAGATGCTGCCTAGCAAGGCAGGGATCTGGAGAGTGGAATGCCTGATTGGGGAGCACCTGCATGCCG

GAATGTCTACCCTGTTTCTGGTGTACAGTAATAAGTGTCAGACACCCCTGGGGATGGCTTCCGGACAT

ATCCGGGATTTCCAGATTACCGCATCTGGACAGTACGGCCAGTGGGCCCCTAAGCTGGCTAGACTGCA

CTATTCCGGGTCTATCAACGCTTGGTCCACAAAAGAGCCTTTCTCTTGGATTAAGGTGGACCTGCTGG

CACCAATGATCATTCATGGCATCAAAACTCAGGGGGCCAGGCAGAAGTTCTCCTCTCTGTACATCTCA

CAGTTTATCATCATGTACAGCCTGGATGGCAAGAAATGGCAGACATACCGCGGCAATAGCACAGGGAC

TCTGATGGTGTTCTTTGGCAACGTGGACAGTTCAGGGATCAAGCACAACATTTTCAATCCCCCTATCA

TTGCTAGATACATCAGGCTGCACCCAACCCATTATTCTATTCGAAGTACACTGCGGATGGAACTGATG

GGGTGCGATCTGAACAGTTGTTCAATGCCCCTGGGAATGGAGTCCAAGGCAATCTCTGACGCCCAGAT

TACCGCTAGCTCCTACTTCACTAATATGTTTGCTACCTGGAGCCCCTCCAAAGCACGACTGCATCTGC

AGGGACGAAGCAACGCATGGCGACCACAGGTGAACAATCCCAAGGAGTGGCTGCAGGTCGATTTTCAG

-continued

AAAACTATGAAGGTGACCGGAGTCACAACTCAGGGCGTGAAAAGTCTGCTGACCTCAATGTACGTCAA

GGAGTTCCTGATCTCTAGTTCACAGGACGGCCACCAGTGGACACTGTTCTTTCAGAACGGAAAGGTGA

AAGTCTTCCAGGGCAATCAGGATTCCTTTACACCTGTGGTCAACTCTCTGGACCCACCCCTGCTGACT

CGCTACCTGCGAATCCACCCACAGTCCTGGGTGCATCAGATTGCACTGAGAATGGAAGTCCTGGGCTG

CGAGGCCCAGGACCTGTATTGA

Codon-ootimized factor VIII cDNA, aka CO/CO3, with deletion of amino acid 1645-1648 variant, Δ4

(SEQ ID NO: 3)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGGAGAT

-continued

CACCCGCACTACCCTGCAGAGTGATCAGGAAGAGATCGACTACGACGATACAATTTCTGTGGAAATGA

AGAAAGAGGACTTCGATATCTATGACGAAGATGAGAACCAGAGTCCTCGATCATTCCAGAAGAAAACC

CGGCATTACTTTATTGCTGCAGTGGAGCGCCTGTGGGATTATGGCATGTCCTCTAGTCCTCACGTGCT

GCGAAATCGGGCCCAGTCAGGGAGCGTCCCACAGTTCAAGAAAGTGGTCTTCCAGGAGTTTACAGACG

GATCCTTTACTCAGCCACTGTACCGGGGCGAACTGAACGAGCACCTGGGGCTGCTGGGACCCTATATC

AGAGCTGAAGTGGAGGATAACATTATGGTCACCTTCAGAAATCAGGCATCTAGGCCTTACAGTTTTTA

TTCAAGCCTGATCTCTTACGAAGAGGACCAGAGGCAGGGAGCAGAACCACGAAAAAACTTCGTGAAGC

CTAATGAGACCAAAACATACTTTTGGAAGGTGCAGCACCATATGGCCCCAACAAAAGACGAATTCGAT

TGCAAGGCATGGGCCTATTTTTCTGACGTGGATCTGGAGAAGGACGTCCACAGTGGCCTGATCGGGCC

ACTGCTGGTGTGTCATACTAACACCCTGAATCCCGCACACGGCAGGCAGGTCACTGTCCAGGAATTCG

CCCTGTTCTTTACCATCTTTGATGAGACAAAAAGCTGGTACTTCACCGAAAACATGGAGCGAAATTGC

CGGGCTCCATGTAATATTCAGATGGAAGACCCCACATTCAAGGAGAACTACCGCTTTCATGCCATCAA

TGGGTATATTATGGATACTCTGCCCGGACTGGTCATGGCTCAGGACCAGAGAATCAGGTGGTACCTGC

TGAGCATGGGGTCCAACGAGAATATCCACTCAATTCATTTCAGCGGACACGTGTTTACTGTCCGGAAG

AAAGAAGAGTATAAAATGGCCCTGTACAACCTGTATCCCGGCGTGTTCGAAACCGTCGAGATGCTGCC

TAGCAAGGCAGGGATCTGGAGAGTGGAATGCCTGATTGGGGAGCACCTGCATGCCGGAATGTCTACCC

TGTTTCTGGTGTACAGTAATAAGTGTCAGACACCCCTGGGGATGGCTTCCGGACATATCCGGGATTTC

CAGATTACCGCATCTGGACAGTACGGCCAGTGGGCCCCTAAGCTGGCTAGACTGCACTATTCCGGGTC

TATCAACGCTTGGTCCACAAAAGAGCCTTTCTCTTGGATTAAGGTGGACCTGCTGGCACCAATGATCA

TTCATGGCATCAAAACTCAGGGGGCCAGGCAGAAGTTCTCCTCTCTGTACATCTCACAGTTTATCATC

ATGTACAGCCTGGATGGCAAGAAATGGCAGACATACCGCGGCAATAGCACAGGGACTCTGATGGTGTT

CTTTGGCAACGTGGACAGTTCAGGGATCAAGCACAACATTTTCAATCCCCCTATCATTGCTAGATACA

TCAGGCTGCACCCAACCCATTATTCTATTCGAAGTACACTGCGGATGGAACTGATGGGGTGCGATCTG

AACAGTTGTTCAATGCCCCTGGGAATGGAGTCCAAGGCAATCTCTGACGCCCAGATTACCGCTAGCTC

CTACTTCACTAATATGTTTGCTACCTGGAGCCCCTCCAAAGCACGACTGCATCTGCAGGGACGAAGCA

ACGCATGGCGACCACAGGTGAACAATCCCAAGGAGTGGCTGCAGGTCGATTTTCAGAAAACTATGAAG

GTGACCGGAGTCACAACTCAGGGCGTGAAAAGTCTGCTGACCTCAATGTACGTCAAGGAGTTCCTGAT

CTCTAGTTCACAGGACGGCCACCAGTGGACACTGTTCTTTCAGAACGGAAAGGTGAAAGTCTTCCAGG

GCAATCAGGATTCCTTTACACCTGTGGTCAACTCTCTGGACCCACCCCTGCTGACTCGCTACCTGCGA

ATCCACCCACAGTCCTGGGTGCATCAGATTGCACTGAGAATGGAAGTCCTGGGCTGCGAGGCCCAGGA

CCTGTATTGA

Codon-ootimized factor VIII cDNA, aka CO/CO3, with deletion of amino acid 1645 variant, Δ1645

(SEQ ID NO: 4)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

-continued

ACCTGGTCAAGGATCTGAACAGCGGACTGATCGGAGCACTGCTGGTGTGTAGGGAAGGGAGCCTGGCT
AAGGAGAAAACCCAGACACTGCATAAGTTCATTCTGCTGTTCGCCGTGTTTGACGAAGGAAAATCATG
GCACAGCGAGACAAAGAATAGTCTGATGCAGGACCGGGATGCCGCTTCAGCCAGAGCTTGGCCCAAAA
TGCACACTGTGAACGGCTACGTCAATCGCTCACTGCCTGGACTGATCGGCTGCCACCGAAAGAGCGTG
TATTGGCATGTCATCGGAATGGGCACCACACCTGAAGTGCACTCCATTTTCCTGGAGGGGCATACCTT
TCTGGTCCGCAACCACCGACAGGCCTCCCTGGAGATCTCTCCAATTACCTTCCTGACAGCTCAGACTC
TGCTGATGGATCTGGGACAGTTCCTGCTGTTTTGCCACATCAGCTCCCACCAGCATGATGGCATGGAG
GCCTACGTGAAAGTGGACAGCTGTCCCGAGGAACCTCAGCTGAGGATGAAGAACAATGAGGAAGCTGA
AGACTATGACGATGACCTGACCGACTCCGAGATGGATGTGGTCCGATTCGATGACGATAACAGCCCCT
CCTTTATCCAGATTAGATCTGTGGCCAAGAAACACCCTAAGACATGGGTCCATTACATCGCAGCCGAG
GAAGAGGACTGGGATTATGCACCACTGGTGCTGGCACCAGACGATCGATCCTACAAATCTCAGTATCT
GAACAATGGACCACAGCGGATTGGCAGAAAGTACAAGAAAGTGAGGTTCATGGCTTATACCGATGAAA
CCTTCAAGACTCGCGAAGCAATCCAGCACGAGAGCGGGATTCTGGGACCACTGCTGTACGGAGAAGTG
GGGGACACCCTGCTGATCATTTTTAAGAACCAGGCCAGCAGGCCTTACAATATCTATCCACATGGAAT
TACAGATGTGCGCCCTCTGTACAGCCGGAGACTGCCAAAGGGCGTCAAACACCTGAAGGACTTCCCAA
TCCTGCCCGGGGAAATTTTTAAGTATAAATGGACTGTCACCGTCGAGGATGGCCCCACTAAGAGCGAC
CCTAGGTGCCTGACCCGCTACTATTCTAGTTTCGTGAATATGGAAAGGGATCTGGCCAGCGGACTGAT
CGGCCCACTGCTGATTTGTTACAAAGAGAGCGTGGATCAGAGAGGCAACCAGATCATGTCCGACAAGA
GGAATGTGATTCTGTTCAGTGTCTTTGACGAAAACCGGTCATGGTATCTGACCGAGAACATCCAGAGA
TTCCTGCCTAATCCAGCCGGAGTGCAGCTGGAAGATCCTGAGTTTCAGGCTTCTAACATCATGCATAG
TATTAATGGCTACGTGTTCGACAGTCTGCAGCTGTCAGTGTGTCTGCACGAGGTCGCTTACTGGTATA
TCCTGAGCATTGGAGCACAGACAGATTTCCTGAGCGTGTTCTTTTCCGGCTACACTTTTAAGCATAAA
ATGGTGTATGAGGACACACTGACTCTGTTCCCCTTCAGCGGCGAAACCGTGTTTATGTCCATGGAGAA
TCCCGGGCTGTGGATCCTGGGATGCCACAACAGCGATTTCAGGAATCGCGGGATGACTGCCCTGCTGA
AAGTGTCAAGCTGTGACAAGAACACCGGAGACTACTATGAAGATTCATACGAGGACATCAGCGCATAT
CTGCTGTCCAAAAACAATGCCATTGAACCCAGGTCTTTTAGTCAGAATCCTCCAGTGCTGAAGCACCA
GCGCGAGATCACCCGCACTACCCTGCAGAGTGATCAGGAAGAGATCGACTACGACGATACAATTTCTG
TGGAAATGAAGAAAGAGGACTTCGATATCTATGACGAAGATGAGAACCAGAGTCCTCGATCATTCCAG
AAGAAAACCCGGCATTACTTTATTGCTGCAGTGGAGCGCCTGTGGGATTATGGCATGTCCTCTAGTCC
TCACGTGCTGCGAAATCGGGCCCAGTCAGGGAGCGTCCCACAGTTCAAGAAAGTGGTCTTCCAGGAGT
TTACAGACGGATCCTTTACTCAGCCACTGTACCGGGGCGAACTGAACGAGCACCTGGGGCTGCTGGGA
CCCTATATCAGAGCTGAAGTGGAGGATAACATTATGGTCACCTTCAGAAATCAGGCATCTAGGCCTTA
CAGTTTTTATTCAAGCCTGATCTCTTACGAAGAGGACCAGAGGCAGGGAGCAGAACCACGAAAAAACT
TCGTGAAGCCTAATGAGACCAAAACATACTTTTGGAAGGTGCAGCACCATATGGCCCCAACAAAAGAC
GAATTCGATTGCAAGGCATGGGCCTATTTTTCTGACGTGGATCTGGAGAAGGACGTCCACAGTGGCCT
GATCGGGCCACTGCTGGTGTGTCATACTAACACCCTGAATCCCGCACACGGCAGGCAGGTCACTGTCC
AGGAATTCGCCCTGTTCTTTACCATCTTTGATGAGACAAAAAGCTGGTACTTCACCGAAAACATGGAG
CGAAATTGCCGGGCTCCATGTAATATTCAGATGGAAGACCCCACATTCAAGGAGAACTACCGCTTTCA
TGCCATCAATGGGTATATTATGGATACTCTGCCCGGACTGGTCATGGCTCAGGACCAGAGAATCAGGT
GGTACCTGCTGAGCATGGGGTCCAACGAGAATATCCACTCAATTCATTTCAGCGGACACGTGTTTACT

-continued

GTCCGGAAGAAAGAAGAGTATAAAATGGCCCTGTACAACCTGTATCCCGGCGTGTTCGAAACCGTCGA

GATGCTGCCTAGCAAGGCAGGGATCTGGAGAGTGGAATGCCTGATTGGGGAGCACCTGCATGCCGGAA

TGTCTACCCTGTTTCTGGTGTACAGTAATAAGTGTCAGACACCCCTGGGGATGGCTTCCGGACATATC

CGGGATTTCCAGATTACCGCATCTGGACAGTACGGCCAGTGGGCCCCTAAGCTGGCTAGACTGCACTA

TTCCGGGTCTATCAACGCTTGGTCCACAAAAGAGCCTTTCTCTTGGATTAAGGTGGACCTGCTGGCAC

CAATGATCATTCATGGCATCAAAACTCAGGGGGCCAGGCAGAAGTTCTCCTCTCTGTACATCTCACAG

TTTATCATCATGTACAGCCTGGATGGCAAGAAATGGCAGACATACCGCGGCAATAGCACAGGGACTCT

GATGGTGTTCTTTGGCAACGTGGACAGTTCAGGGATCAAGCACAACATTTTCAATCCCCCTATCATTG

CTAGATACATCAGGCTGCACCCAACCCATTATTCTATTCGAAGTACACTGCGGATGGAACTGATGGGG

TGCGATCTGAACAGTTGTTCAATGCCCCTGGGAATGGAGTCCAAGGCAATCTCTGACGCCCAGATTAC

CGCTAGCTCCTACTTCACTAATATGTTTGCTACCTGGAGCCCCTCCAAAGCACGACTGCATCTGCAGG

GACGAAGCAACGCATGGCGACCACAGGTGAACAATCCCAAGGAGTGGCTGCAGGTCGATTTTCAGAAA

ACTATGAAGGTGACCGGAGTCACAACTCAGGGCGTGAAAAGTCTGCTGACCTCAATGTACGTCAAGGA

GTTCCTGATCTCTAGTTCACAGGACGGCCACCAGTGGACACTGTTCTTTCAGAACGGAAAGGTGAAAG

TCTTCCAGGGCAATCAGGATTCCTTTACACCTGTGGTCAACTCTCTGGACCCACCCCTGCTGACTCGC

TACCTGCGAATCCACCCACAGTCCTGGGTGCATCAGATTGCACTGAGAATGGAAGTCCTGGGCTGCGA

GGCCCAGGACCTGTATTGA

Codon-ootimized factor VIII cDNA, aka CO/CO3, with deletion of amino acids 1645 and 1646 variant, Δ2

(SEQ ID NO: 5)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

-continued

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGCAGCG

CGAGATCACCCGCACTACCCTGCAGAGTGATCAGGAAGAGATCGACTACGACGATACAATTTCTGTGG

AAATGAAGAAAGAGGACTTCGATATCTATGACGAAGATGAGAACCAGAGTCCTCGATCATTCCAGAAG

AAAACCCGGCATTACTTTATTGCTGCAGTGGAGCGCCTGTGGGATTATGGCATGTCCTCTAGTCCTCA

CGTGCTGCGAAATCGGGCCCAGTCAGGGAGCGTCCCACAGTTCAAGAAAGTGGTCTTCCAGGAGTTTA

CAGACGGATCCTTTACTCAGCCACTGTACCGGGGCGAACTGAACGAGCACCTGGGGCTGCTGGGACCC

TATATCAGAGCTGAAGTGGAGGATAACATTATGGTCACCTTCAGAAATCAGGCATCTAGGCCTTACAG

TTTTTATTCAAGCCTGATCTCTTACGAAGAGGACCAGAGGCAGGGAGCAGAACCACGAAAAAACTTCG

TGAAGCCTAATGAGACCAAAACATACTTTTGGAAGGTGCAGCACCATATGGCCCCAACAAAAGACGAA

TTCGATTGCAAGGCATGGGCCTATTTTTCTGACGTGGATCTGGAGAAGGACGTCCACAGTGGCCTGAT

CGGGCCACTGCTGGTGTGTCATACTAACACCCTGAATCCCGCACACGGCAGGCAGGTCACTGTCCAGG

AATTCGCCCTGTTCTTTACCATCTTTGATGAGACAAAAAGCTGGTACTTCACCGAAAACATGGAGCGA

AATTGCCGGGCTCCATGTAATATTCAGATGGAAGACCCCACATTCAAGGAGAACTACCGCTTTCATGC

CATCAATGGGTATATTATGGATACTCTGCCCGGACTGGTCATGGCTCAGGACCAGAGAATCAGGTGGT

ACCTGCTGAGCATGGGGTCCAACGAGAATATCCACTCAATTCATTTCAGCGGACACGTGTTTACTGTC

CGGAAGAAAGAAGAGTATAAAATGGCCCTGTACAACCTGTATCCCGGCGTGTTCGAAACCGTCGAGAT

GCTGCCTAGCAAGGCAGGGATCTGGAGAGTGGAATGCCTGATTGGGGAGCACCTGCATGCCGGAATGT

CTACCCTGTTTCTGGTGTACAGTAATAAGTGTCAGACACCCCTGGGGATGGCTTCCGGACATATCCGG

GATTTCCAGATTACCGCATCTGGACAGTACGGCCAGTGGGCCCCTAAGCTGGCTAGACTGCACTATTC

CGGGTCTATCAACGCTTGGTCCACAAAAGAGCCTTTCTCTTGGATTAAGGTGGACCTGCTGGCACCAA

TGATCATTCATGGCATCAAAACTCAGGGGGCCAGGCAGAAGTTCTCCTCTCTGTACATCTCACAGTTT

ATCATCATGTACAGCCTGGATGGCAAGAAATGGCAGACATACCGCGGCAATAGCACAGGGACTCTGAT

GGTGTTCTTTGGCAACGTGGACAGTTCAGGGATCAAGCACAACATTTTCAATCCCCCTATCATTGCTA

GATACATCAGGCTGCACCCAACCCATTATTCTATTCGAAGTACACTGCGGATGGAACTGATGGGGTGC

GATCTGAACAGTTGTTCAATGCCCCTGGGAATGGAGTCCAAGGCAATCTCTGACGCCCAGATTACCGC

TAGCTCCTACTTCACTAATATGTTTGCTACCTGGAGCCCCTCCAAAGCACGACTGCATCTGCAGGGAC

GAAGCAACGCATGGCGACCACAGGTGAACAATCCCAAGGAGTGGCTGCAGGTCGATTTTCAGAAAACT

ATGAAGGTGACCGGAGTCACAACTCAGGGCGTGAAAAGTCTGCTGACCTCAATGTACGTCAAGGAGTT

CCTGATCTCTAGTTCACAGGACGGCCACCAGTGGACACTGTTCTTTCAGAACGGAAAGGTGAAAGTCT

TCCAGGGCAATCAGGATTCCTTTACACCTGTGGTCAACTCTCTGGACCCACCCCTGCTGACTCGCTAC

-continued

CTGCGAATCCACCCACAGTCCTGGGTGCATCAGATTGCACTGAGAATGGAAGTCCTGGGCTGCGAGGC

CCAGGACCTGTATTGA

Codon-optimized factor VIII cDNA, aka CO/CO3, with deletion of amino acids 1645-1647 variant, Δ3

(SEQ ID NO: 6)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGCGCGA

GATCACCCGCACTACCCTGCAGAGTGATCAGGAAGAGATCGACTACGACGATACAATTTCTGTGGAAA

TGAAGAAAGAGGACTTCGATATCTATGACGAAGATGAGAACCAGAGTCCTCGATCATTCCAGAAGAAA

ACCCGGCATTACTTTATTGCTGCAGTGGAGCGCCTGTGGGATTATGGCATGTCCTCTAGTCCTCACGT

-continued

GCTGCGAAATCGGGCCCAGTCAGGGAGCGTCCCACAGTTCAAGAAAGTGGTCTTCCAGGAGTTTACAG

ACGGATCCTTTACTCAGCCACTGTACCGGGGCGAACTGAACGAGCACCTGGGGCTGCTGGGACCCTAT

ATCAGAGCTGAAGTGGAGGATAACATTATGGTCACCTTCAGAAATCAGGCATCTAGGCCTTACAGTTT

TTATTCAAGCCTGATCTCTTACGAAGAGGACCAGAGGCAGGGAGCAGAACCACGAAAAAACTTCGTGA

AGCCTAATGAGACCAAAACATACTTTTGGAAGGTGCAGCACCATATGGCCCCAACAAAAGACGAATTC

GATTGCAAGGCATGGGCCTATTTTTCTGACGTGGATCTGGAGAAGGACGTCCACAGTGGCCTGATCGG

GCCACTGCTGGTGTGTCATACTAACACCCTGAATCCCGCACACGGCAGGCAGGTCACTGTCCAGGAAT

TCGCCCTGTTCTTTACCATCTTTGATGAGACAAAAAGCTGGTACTTCACCGAAAACATGGAGCGAAAT

TGCCGGGCTCCATGTAATATTCAGATGGAAGACCCCACATTCAAGGAGAACTACCGCTTTCATGCCAT

CAATGGGTATATTATGGATACTCTGCCCGGACTGGTCATGGCTCAGGACCAGAGAATCAGGTGGTACC

TGCTGAGCATGGGGTCCAACGAGAATATCCACTCAATTCATTTCAGCGGACACGTGTTTACTGTCCGG

AAGAAAGAAGAGTATAAAATGGCCCTGTACAACCTGTATCCCGGCGTGTTCGAAACCGTCGAGATGCT

GCCTAGCAAGGCAGGGATCTGGAGAGTGGAATGCCTGATTGGGGAGCACCTGCATGCCGGAATGTCTA

CCCTGTTTCTGGTGTACAGTAATAAGTGTCAGACACCCCTGGGGATGGCTTCCGGACATATCCGGGAT

TTCCAGATTACCGCATCTGGACAGTACGGCCAGTGGGCCCCTAAGCTGGCTAGACTGCACTATTCCGG

GTCTATCAACGCTTGGTCCACAAAAGAGCCTTTCTCTTGGATTAAGGTGGACCTGCTGGCACCAATGA

TCATTCATGGCATCAAAACTCAGGGGGCCAGGCAGAAGTTCTCCTCTCTGTACATCTCACAGTTTATC

ATCATGTACAGCCTGGATGGCAAGAAATGGCAGACATACCGCGGCAATAGCACAGGGACTCTGATGGT

GTTCTTTGGCAACGTGGACAGTTCAGGGATCAAGCACAACATTTTCAATCCCCCTATCATTGCTAGAT

ACATCAGGCTGCACCCAACCCATTATTCTATTCGAAGTACACTGCGGATGGAACTGATGGGGTGCGAT

CTGAACAGTTGTTCAATGCCCCTGGGAATGGAGTCCAAGGCAATCTCTGACGCCCAGATTACCGCTAG

CTCCTACTTCACTAATATGTTTGCTACCTGGAGCCCCTCCAAAGCACGACTGCATCTGCAGGGACGAA

GCAACGCATGGCGACCACAGGTGAACAATCCCAAGGAGTGGCTGCAGGTCGATTTTCAGAAAACTATG

AAGGTGACCGGAGTCACAACTCAGGGCGTGAAAAGTCTGCTGACCTCAATGTACGTCAAGGAGTTCCT

GATCTCTAGTTCACAGGACGGCCACCAGTGGACACTGTTCTTTCAGAACGGAAAGGTGAAAGTCTTCC

AGGGCAATCAGGATTCCTTTACACCTGTGGTCAACTCTCTGGACCCACCCCTGCTGACTCGCTACCTG

CGAATCCACCCACAGTCCTGGGTGCATCAGATTGCACTGAGAATGGAAGTCCTGGGCTGCGAGGCCCA

GGACCTGTATTGA

Codon-ootimized FVIII cDNA, aka CO/CO3, with deletion of amino acid 1648 variant, Δ1648

(SEQ ID NO: 7)

ATGCAGATTGAGCTGTCAACTTGCTTTTTCCTGTGCCTGCTGAGATTTTGTTTTTCCGCTACTAGAAG

ATACTACCTGGGGGCTGTGGAACTGTCTTGGGATTACATGCAGAGTGACCTGGGAGAGCTGCCAGTGG

ACGCACGATTTCCACCTAGAGTCCCTAAATCATTCCCCTTCAACACCAGCGTGGTCTATAAGAAAACA

CTGTTCGTGGAGTTTACTGATCACCTGTTCAACATCGCTAAGCCTCGGCCACCCTGGATGGGACTGCT

GGGACCAACAATCCAGGCAGAGGTGTACGACACCGTGGTCATTACACTGAAAAACATGGCCTCACACC

CCGTGAGCCTGCATGCTGTGGGCGTCAGCTACTGGAAGGCTTCCGAAGGGGCAGAGTATGACGATCAG

ACTTCCCAGAGAGAAAAAGAGGACGATAAGGTGTTTCCTGGCGGGTCTCATACCTATGTGTGGCAGGT

CCTGAAAGAGAATGGCCCCATGGCTTCCGACCCTCTGTGCCTGACCTACTCTTATCTGAGTCACGTGG

ACCTGGTCAAGGATCTGAACAGCGGACTGATCGGAGCACTGCTGGTGTGTAGGGAAGGGAGCCTGGCT

AAGGAGAAAACCCAGACACTGCATAAGTTCATTCTGCTGTTCGCCGTGTTTGACGAAGGAAAATCATG

GCACAGCGAGACAAAGAATAGTCTGATGCAGGACCGGGATGCCGCTTCAGCCAGAGCTTGGCCCAAAA

-continued

TGCACACTGTGAACGGCTACGTCAATCGCTCACTGCCTGGACTGATCGGCTGCCACCGAAAGAGCGTG

TATTGGCATGTCATCGGAATGGGCACCACACCTGAAGTGCACTCCATTTTCCTGGAGGGGCATACCTT

TCTGGTCCGCAACCACCGACAGGCCTCCCTGGAGATCTCTCCAATTACCTTCCTGACAGCTCAGACTC

TGCTGATGGATCTGGGACAGTTCCTGCTGTTTTGCCACATCAGCTCCCACCAGCATGATGGCATGGAG

GCCTACGTGAAAGTGGACAGCTGTCCCGAGGAACCTCAGCTGAGGATGAAGAACAATGAGGAAGCTGA

AGACTATGACGATGACCTGACCGACTCCGAGATGGATGTGGTCCGATTCGATGACGATAACAGCCCCT

CCTTTATCCAGATTAGATCTGTGGCCAAGAAACACCCTAAGACATGGGTCCATTACATCGCAGCCGAG

GAAGAGGACTGGGATTATGCACCACTGGTGCTGGCACCAGACGATCGATCCTACAAATCTCAGTATCT

GAACAATGGACCACAGCGGATTGGCAGAAAGTACAAGAAAGTGAGGTTCATGGCTTATACCGATGAAA

CCTTCAAGACTCGCGAAGCAATCCAGCACGAGAGCGGGATTCTGGGACCACTGCTGTACGGAGAAGTG

GGGGACACCCTGCTGATCATTTTTAAGAACCAGGCCAGCAGGCCTTACAATATCTATCCACATGGAAT

TACAGATGTGCGCCCTCTGTACAGCCGGAGACTGCCAAAGGGCGTCAAACACCTGAAGGACTTCCCAA

TCCTGCCCGGGGAAATTTTTAAGTATAAATGGACTGTCACCGTCGAGGATGGCCCCACTAAGAGCGAC

CCTAGGTGCCTGACCCGCTACTATTCTAGTTTCGTGAATATGGAAAGGGATCTGGCCAGCGGACTGAT

CGGCCCACTGCTGATTTGTTACAAAGAGAGCGTGGATCAGAGAGGCAACCAGATCATGTCCGACAAGA

GGAATGTGATTCTGTTCAGTGTCTTTGACGAAAACCGGTCATGGTATCTGACCGAGAACATCCAGAGA

TTCCTGCCTAATCCAGCCGGAGTGCAGCTGGAAGATCCTGAGTTTCAGGCTTCTAACATCATGCATAG

TATTAATGGCTACGTGTTCGACAGTCTGCAGCTGTCAGTGTGTCTGCACGAGGTCGCTTACTGGTATA

TCCTGAGCATTGGAGCACAGACAGATTTCCTGAGCGTGTTCTTTTCCGGCTACACTTTTAAGCATAAA

ATGGTGTATGAGGACACACTGACTCTGTTCCCCTTCAGCGGCGAAACCGTGTTTATGTCCATGGAGAA

TCCCGGGCTGTGGATCCTGGGATGCCACAACAGCGATTTCAGGAATCGCGGGATGACTGCCCTGCTGA

AAGTGTCAAGCTGTGACAAGAACACCGGAGACTACTATGAAGATTCATACGAGGACATCAGCGCATAT

CTGCTGTCCAAAAACAATGCCATTGAACCCAGGTCTTTTAGTCAGAATCCTCCAGTGCTGAAGAGGCA

CCAGGAGATCACCCGCACTACCCTGCAGAGTGATCAGGAAGAGATCGACTACGACGATACAATTTCTG

TGGAAATGAAGAAAGAGGACTTCGATATCTATGACGAAGATGAGAACCAGAGTCCTCGATCATTCCAG

AAGAAAACCCGGCATTACTTTATTGCTGCAGTGGAGCGCCTGTGGGATTATGGCATGTCCTCTAGTCC

TCACGTGCTGCGAAATCGGGCCCAGTCAGGGAGCGTCCCACAGTTCAAGAAAGTGGTCTTCCAGGAGT

TTACAGACGGATCCTTTACTCAGCCACTGTACCGGGGCGAACTGAACGAGCACCTGGGGCTGCTGGGA

CCCTATATCAGAGCTGAAGTGGAGGATAACATTATGGTCACCTTCAGAAATCAGGCATCTAGGCCTTA

CAGTTTTTATTCAAGCCTGATCTCTTACGAAGAGGACCAGAGGCAGGGAGCAGAACCACGAAAAAACT

TCGTGAAGCCTAATGAGACCAAAACATACTTTTGGAAGGTGCAGCACCATATGGCCCCAACAAAAGAC

GAATTCGATTGCAAGGCATGGGCCTATTTTTCTGACGTGGATCTGGAGAAGGACGTCCACAGTGGCCT

GATCGGGCCACTGCTGGTGTGTCATACTAACACCCTGAATCCCGCACACGGCAGGCAGGTCACTGTCC

AGGAATTCGCCCTGTTCTTTACCATCTTTGATGAGACAAAAAGCTGGTACTTCACCGAAAACATGGAG

CGAAATTGCCGGGCTCCATGTAATATTCAGATGGAAGACCCCACATTCAAGGAGAACTACCGCTTTCA

TGCCATCAATGGGTATATTATGGATACTCTGCCCGGACTGGTCATGGCTCAGGACCAGAGAATCAGGT

GGTACCTGCTGAGCATGGGGTCCAACGAGAATATCCACTCAATTCATTTCAGCGGACACGTGTTTACT

GTCCGGAAGAAAGAAGAGTATAAAATGGCCCTGTACAACCTGTATCCCGGCGTGTTCGAAACCGTCGA

GATGCTGCCTAGCAAGGCAGGGATCTGGAGAGTGGAATGCCTGATTGGGGAGCACCTGCATGCCGGAA

TGTCTACCCTGTTTCTGGTGTACAGTAATAAGTGTCAGACACCCCTGGGGATGGCTTCCGGACATATC

-continued

CGGGATTTCCAGATTACCGCATCTGGACAGTACGGCCAGTGGGCCCCTAAGCTGGCTAGACTGCACTA

TTCCGGGTCTATCAACGCTTGGTCCACAAAAGAGCCTTTCTCTTGGATTAAGGTGGACCTGCTGGCAC

CAATGATCATTCATGGCATCAAAACTCAGGGGGCCAGGCAGAAGTTCTCCTCTCTGTACATCTCACAG

TTTATCATCATGTACAGCCTGGATGGCAAGAAATGGCAGACATACCGCGGCAATAGCACAGGGACTCT

GATGGTGTTCTTTGGCAACGTGGACAGTTCAGGGATCAAGCACAACATTTTCAATCCCCCTATCATTG

CTAGATACATCAGGCTGCACCCAACCCATTATTCTATTCGAAGTACACTGCGGATGGAACTGATGGGG

TGCGATCTGAACAGTTGTTCAATGCCCCTGGGAATGGAGTCCAAGGCAATCTCTGACGCCCAGATTAC

CGCTAGCTCCTACTTCACTAATATGTTTGCTACCTGGAGCCCCTCCAAAGCACGACTGCATCTGCAGG

GACGAAGCAACGCATGGCGACCACAGGTGAACAATCCCAAGGAGTGGCTGCAGGTCGATTTTCAGAAA

ACTATGAAGGTGACCGGAGTCACAACTCAGGGCGTGAAAAGTCTGCTGACCTCAATGTACGTCAAGGA

GTTCCTGATCTCTAGTTCACAGGACGGCCACCAGTGGACACTGTTCTTTCAGAACGGAAAGGTGAAAG

TCTTCCAGGGCAATCAGGATTCCTTTACACCTGTGGTCAACTCTCTGGACCCACCCCTGCTGACTCGC

TACCTGCGAATCCACCCACAGTCCTGGGTGCATCAGATTGCACTGAGAATGGAAGTCCTGGGCTGCGA

GGCCCAGGACCTGTATTGA

TTR promoter with 4 nucleotide mutation (TTRm), (SEQ ID NO: 8)

GTCTGTCTGCACATTTCGTAGAGCGAGTGTTCCGATACTCTAATCTCCCTAGGCAAGGTTCATATTGA

CTTAGGTTACTTATTCTCCTTTTGTTGACTAAGTCAATAATCAGAATCAGCAGGTTTGGAGTCAGCTT

GGCAGGGATCAGCAGCCTGGGTTGGAAGGAGGGGGTATAAAAGCCCCTTCACCAGGAGAAGCCGTCAC

ACAGATCCACAAGCTCCT

The DNA sequence of the entire full-length factor VIII construct including the TTR promoter with the four nucleotide mutation, synthetic intron, codon-optimized factor VIIIcDNA and polyadenylation (Poly A) signal sequence are provided (SEQ ID NO:9). Also highlighted in SEQ ID NO: 9 are the codons coding for the 4 amino acid PACE/furin cleavage site, wherein 1, 2, 3 or all 4 amino acids are optionally deleted.

Full length construct including TTR promoter with 4 nucleotide mutation (TTRm), synthetic intron, codon-optimized factor VIII cDNA (PACE/furin underlined), poly A (SEQ ID NO: 9)

GTCTGTCTGCACATTTCGTAGAGCGAGTGTTCCGATACTCTAATCTCCCTAGGCAAGGTTCATATTga ctTAGGTTACTTATTCTCCTTTTGTTGACTAAGTCAATAATCAGAATCAGCAGGTTTGGAGTCAGCTT

GGCAGGGATCAGCAGCCTGGGTTGGAAGGAGGGGGTATAAAAGCCCCTTCACCAGGAGAAGCCGTCAC

ACAGATCCACAAGCTCCTGCTAGCAGGTAAGTGCCGTGTGTGGTTCCCGCGGGCCTGGCCTCTTTACG

GGTTATGGCCCTTGCGTGCCTTGAATTACTGACACTGACATCCACTTTTTCTTTTTCTCCACAGGTTT

AAACGCCACCATGCAGATTGAGCTGTCAACTTGCTTTTTCCTGTGCCTGCTGAGATTTTGTTTTTCCG

CTACTAGAAGATACTACCTGGGGGCTGTGGAACTGTCTTGGGATTACATGCAGAGTGACCTGGGAGAG

CTGCCAGTGGACGCACGATTTCCACCTAGAGTCCCTAAATCATTCCCCTTCAACACCAGCGTGGTCTA

TAAGAAAACACTGTTCGTGGAGTTTACTGATCACCTGTTCAACATCGCTAAGCCTCGGCCACCCTGGA

TGGGACTGCTGGGACCAACAATCCAGGCAGAGGTGTACGACACCGTGGTCATTACACTGAAAAACATG

GCCTCACACCCCGTGAGCCTGCATGCTGTGGGCGTCAGCTACTGGAAGGCTTCCGAAGGGGCAGAGTA

TGACGATCAGACTTCCCAGAGAGAAAAAGAGGACGATAAGGTGTTTCCTGGCGGGTCTCATACCTATG

TGTGGCAGGTCCTGAAAGAGAATGGCCCCATGGCTTCCGACCCTCTGTGCCTGACCTACTCTTATCTG

AGTCACGTGGACCTGGTCAAGGATCTGAACAGCGGACTGATCGGAGCACTGCTGGTGTGTAGGGAAGG

GAGCCTGGCTAAGGAGAAAACCCAGACACTGCATAAGTTCATTCTGCTGTTCGCCGTGTTTGACGAAG

GAAAATCATGGCACAGCGAGACAAAGAATAGTCTGATGCAGGACCGGGATGCCGCTTCAGCCAGAGCT

-continued

TGGCCCAAAATGCACACTGTGAACGGCTACGTCAATCGCTCACTGCCTGGACTGATCGGCTGCCACCG

AAAGAGCGTGTATTGGCATGTCATCGGAATGGGCACCACACCTGAAGTGCACTCCATTTTCCTGGAGG

GGCATACCTTTCTGGTCCGCAACCACCGACAGGCCTCCCTGGAGATCTCTCCAATTACCTTCCTGACA

GCTCAGACTCTGCTGATGGATCTGGGACAGTTCCTGCTGTTTTGCCACATCAGCTCCCACCAGCATGA

TGGCATGGAGGCCTACGTGAAAGTGGACAGCTGTCCCGAGGAACCTCAGCTGAGGATGAAGAACAATG

AGGAAGCTGAAGACTATGACGATGACCTGACCGACTCCGAGATGGATGTGGTCCGATTCGATGACGAT

AACAGCCCCTCCTTTATCCAGATTAGATCTGTGGCCAAGAAACACCCTAAGACATGGGTCCATTACAT

CGCAGCCGAGGAAGAGGACTGGGATTATGCACCACTGGTGCTGGCACCAGACGATCGATCCTACAAAT

CTCAGTATCTGAACAATGGACCACAGCGGATTGGCAGAAAGTACAAGAAAGTGAGGTTCATGGCTTAT

ACCGATGAAACCTTCAAGACTCGCGAAGCAATCCAGCACGAGAGCGGGATTCTGGGACCACTGCTGTA

CGGAGAAGTGGGGGACACCCTGCTGATCATTTTTAAGAACCAGGCCAGCAGGCCTTACAATATCTATC

CACATGGAATTACAGATGTGCGCCCTCTGTACAGCCGGAGACTGCCAAAGGGCGTCAAACACCTGAAG

GACTTCCCAATCCTGCCCGGGGAAATTTTTAAGTATAAATGGACTGTCACCGTCGAGGATGGCCCCAC

TAAGAGCGACCCTAGGTGCCTGACCCGCTACTATTCTAGTTTCGTGAATATGGAAAGGGATCTGGCCA

GCGGACTGATCGGCCCACTGCTGATTTGTTACAAAGAGAGCGTGGATCAGAGAGGCAACCAGATCATG

TCCGACAAGAGGAATGTGATTCTGTTCAGTGTCTTTGACGAAAACCGGTCATGGTATCTGACCGAGAA

CATCCAGAGATTCCTGCCTAATCCAGCCGGAGTGCAGCTGGAAGATCCTGAGTTTCAGGCTTCTAACA

TCATGCATAGTATTAATGGCTACGTGTTCGACAGTCTGCAGCTGTCAGTGTGTCTGCACGAGGTCGCT

TACTGGTATATCCTGAGCATTGGAGCACAGACAGATTTCCTGAGCGTGTTCTTTTCCGGCTACACTTT

TAAGCATAAAATGGTGTATGAGGACACACTGACTCTGTTCCCCTTCAGCGGCGAAACCGTGTTTATGT

CCATGGAGAATCCCGGGCTGTGGATCCTGGGATGCCACAACAGCGATTTCAGGAATCGCGGGATGACT

GCCCTGCTGAAAGTGTCAAGCTGTGACAAGAACACCGGAGACTACTATGAAGATTCATACGAGGACAT

CAGCGCATATCTGCTGTCCAAAAACAATGCCATTGAACCCAGGTCTTTTAGTCAGAATCCTCCAGTGC

TGAAGAGGCACCAGCGCGAGATCACCCGCACTACCCTGCAGAGTGATCAGGAAGAGATCGACTACGAC

GATACAATTTCTGTGGAAATGAAGAAAGAGGACTTCGATATCTATGACGAAGATGAGAACCAGAGTCC

TCGATCATTCCAGAAGAAAACCCGGCATTACTTTATTGCTGCAGTGGAGCGCCTGTGGGATTATGGCA

TGTCCTCTAGTCCTCACGTGCTGCGAAATCGGGCCCAGTCAGGGAGCGTCCCACAGTTCAAGAAAGTG

GTCTTCCAGGAGTTTACAGACGGATCCTTTACTCAGCCACTGTACCGGGGCGAACTGAACGAGCACCT

GGGGCTGCTGGGACCCTATATCAGAGCTGAAGTGGAGGATAACATTATGGTCACCTTCAGAAATCAGG

CATCTAGGCCTTACAGTTTTTATTCAAGCCTGATCTCTTACGAAGAGGACCAGAGGCAGGGAGCAGAA

CCACGAAAAAACTTCGTGAAGCCTAATGAGACCAAAACATACTTTTGGAAGGTGCAGCACCATATGGC

CCCAACAAAAGACGAATTCGATTGCAAGGCATGGGCCTATTTTTCTGACGTGGATCTGGAGAAGGACG

TCCACAGTGGCCTGATCGGGCCACTGCTGGTGTGTCATACTAACACCCTGAATCCCGCACACGGCAGG

CAGGTCACTGTCCAGGAATTCGCCCTGTTCTTTACCATCTTTGATGAGACAAAAAGCTGGTACTTCAC

CGAAAACATGGAGCGAAATTGCCGGGCTCCATGTAATATTCAGATGGAAGACCCCACATTCAAGGAGA

ACTACCGCTTTCATGCCATCAATGGGTATATTATGGATACTCTGCCCGGACTGGTCATGGCTCAGGAC

CAGAGAATCAGGTGGTACCTGCTGAGCATGGGGTCCAACGAGAATATCCACTCAATTCATTTCAGCGG

ACACGTGTTTACTGTCCGGAAGAAAGAAGAGTATAAAATGGCCCTGTACAACCTGTATCCCGGCGTGT

TCGAAACCGTCGAGATGCTGCCTAGCAAGGCAGGGATCTGGAGAGTGGAATGCCTGATTGGGGAGCAC

CTGCATGCCGGAATGTCTACCCTGTTTCTGGTGTACAGTAATAAGTGTCAGACACCCCTGGGGATGGC

-continued

TTCCGGACATATCCGGGATTTCCAGATTACCGCATCTGGACAGTACGGCCAGTGGGCCCCTAAGCTGG

CTAGACTGCACTATTCCGGGTCTATCAACGCTTGGTCCACAAAAGAGCCTTTCTCTTGGATTAAGGTG

GACCTGCTGGCACCAATGATCATTCATGGCATCAAAACTCAGGGGGCCAGGCAGAAGTTCTCCTCTCT

GTACATCTCACAGTTTATCATCATGTACAGCCTGGATGGCAAGAAATGGCAGACATACCGCGGCAATA

GCACAGGGACTCTGATGGTGTTCTTTGGCAACGTGGACAGTTCAGGGATCAAGCACAACATTTTCAAT

CCCCCTATCATTGCTAGATACATCAGGCTGCACCCAACCCATTATTCTATTCGAAGTACACTGCGGAT

GGAACTGATGGGGTGCGATCTGAACAGTTGTTCAATGCCCCTGGGAATGGAGTCCAAGGCAATCTCTG

ACGCCCAGATTACCGCTAGCTCCTACTTCACTAATATGTTTGCTACCTGGAGCCCCTCCAAAGCACGA

CTGCATCTGCAGGGACGAAGCAACGCATGGCGACCACAGGTGAACAATCCCAAGGAGTGGCTGCAGGT

CGATTTTCAGAAAACTATGAAGGTGACCGGAGTCACAACTCAGGGCGTGAAAAGTCTGCTGACCTCAA

TGTACGTCAAGGAGTTCCTGATCTCTAGTTCACAGGACGGCCACCAGTGGACACTGTTCTTTCAGAAC

GGAAAGGTGAAAGTCTTCCAGGGCAATCAGGATTCCTTTACACCTGTGGTCAACTCTCTGGACCCACC

CCTGCTGACTCGCTACCTGCGAATCCACCCACAGTCCTGGGTGCATCAGATTGCACTGAGAATGGAAG

TCCTGGGCTGCGAGGCCCAGGACCTGTATTGAGCGGCCGCAATAAAAGATCAGAGCTCTAGAGATCTG

TGTGTTGGTTTTTTGTGT

Codon-optimized factor VIII cDNA, aka CO1

(SEQ ID NO: 10)

ATGCAGATCGAGCTGTCTACCTGCTTCTTCCTGTGCCTGCTGCGGTTCTGCTTCAGCGCCACCAGACG

GTACTATCTGGGCGCCGTGGAACTGAGCTGGGACTACATGCAGAGCGACCTGGGCGAGCTGCCCGTGG

ATGCCAGATTCCCTCCAAGAGTGCCCAAGAGCTTCCCCTTCAACACCTCCGTGGTGTACAAGAAAACC

CTGTTCGTGGAATTCACCGACCACCTGTTCAATATCGCCAAGCCCAGACCCCCCTGGATGGGCCTGCT

GGGACCTACAATTCAGGCCGAGGTGTACGACACCGTCGTGATCACCCTGAAGAACATGGCCAGCCACC

CCGTGTCTCTGCATGCCGTGGGAGTGTCCTACTGGAAGGCCTCTGAGGGCGCCGAGTACGACGATCAG

ACCAGCCAGCGCGAGAAAGAGGACGACAAGGTGTTCCCTGGCGGCAGCCACACCTACGTGTGGCAGGT

GCTGAAAGAAAACGGCCCCATGGCCTCCGACCCTCTGTGCCTGACATACAGCTACCTGAGCCACGTGG

ACCTCGTGAAGGACCTGAACAGCGGCCTGATCGGAGCCCTGCTCGTGTGTAGAGAGGGCAGCCTGGCC

AAAGAGAAAACCCAGACCCTGCACAAGTTCATCCTGCTGTTCGCCGTGTTCGACGAGGGCAAGAGCTG

GCACAGCGAGACAAAGAACAGCCTGATGCAGGACCGGGACGCCGCCTCTGCTAGAGCCTGGCCCAAAA

TGCACACCGTGAACGGCTACGTGAACAGAAGCCTGCCCGGACTGATCGGCTGCCACCGGAAGTCTGTG

TACTGGCACGTGATCGGCATGGGCACCACCCCTGAGGTGCACAGCATCTTTCTGGAAGGACACACCTT

TCTCGTGCGGAACCACCGGCAGGCCAGCCTGGAAATCAGCCCTATCACCTTCCTGACCGCCCAGACAC

TGCTGATGGACCTGGGCCAGTTTCTGCTGTTCTGCCACATCAGCTCCCACCAGCACGACGGCATGGAA

GCCTACGTGAAGGTGGACAGCTGCCCCGAGGAACCCCAGCTGCGGATGAAGAACAACGAGGAAGCCGA

GGACTACGACGACGACCTGACCGACAGCGAGATGGACGTGGTGCGCTTCGACGACGATAACAGCCCCA

GCTTCATCCAGATCAGAAGCGTGGCCAAGAAGCACCCCAAGACCTGGGTGCACTATATCGCCGCCGAG

GAAGAGGACTGGGATTACGCCCCTCTGGTGCTGGCCCCCGACGACAGAAGCTACAAGAGCCAGTACCT

GAACAATGGCCCCCAGCGGATCGGCCGGAAGTATAAGAAAGTGCGGTTCATGGCCTACACCGACGAGA

CATTCAAGACCAGAGAGGCCATCCAGCACGAGAGCGGCATCCTGGGCCCTCTGCTGTATGGCGAAGTG

GGCGACACCCTGCTGATCATCTTCAAGAACCAGGCCAGCAGACCCTACAACATCTACCCTCACGGCAT

CACCGACGTGCGGCCCCTGTACTCTAGAAGGCTGCCCAAGGGCGTGAAACACCTGAAGGACTTCCCCA

TCCTGCCCGGCGAGATCTTCAAGTACAAGTGGACCGTGACCGTGGAAGATGGCCCCACCAAGAGCGAC

CCCAGATGCCTGACACGGTACTACAGCAGCTTCGTGAACATGGAACGGGACCTGGCCTCCGGCCTGAT

-continued

TGGCCCACTGCTGATCTGCTACAAAGAAAGCGTGGACCAGCGGGGCAACCAGATCATGAGCGACAAGC
GGAACGTGATCCTGTTTAGCGTGTTCGATGAGAACCGGTCCTGGTATCTGACCGAGAATATCCAGCGG
TTCCTGCCCAACCCTGCCGGCGTGCAGCTGGAAGATCCTGAGTTCCAGGCCTCCAACATCATGCACTC
CATCAATGGCTATGTGTTCGACAGCCTGCAGCTGAGCGTGTGCCTGCACGAGGTGGCCTACTGGTACA
TCCTGAGCATCGGGGCCCAGACCGACTTCCTGTCCGTGTTCTTCTCCGGCTACACCTTCAAGCACAAG
ATGGTGTACGAGGATACCCTGACCCTGTTCCCCTTTAGCGGCGAAACCGTGTTCATGAGCATGGAAAA
CCCCGGCCTGTGGATCCTGGGCTGCCACAACAGCGACTTCCGGAACAGAGGCATGACCGCCCTGCTGA
AGGTGTCCAGCTGCGACAAGAACACCGGCGACTACTACGAGGACAGCTATGAGGACATCAGCGCCTAC
CTGCTGAGCAAGAACAATGCCATCGAGCCCAGAAGCTTCAGCCAGAACCCCCCCGTGCTGAAGCGGCA
CCAGAGAGAGATCACCCGGACCACCCTGCAGTCCGACCAGGAAGAGATCGATTACGACGACACCATCA
GCGTGGAAATGAAGAAAGAAGATTTCGACATCTACGACGAGGACGAGAACCAGAGCCCCCGGTCCTTT
CAGAAAAAGACCCGGCACTACTTCATTGCCGCTGTGGAACGGCTGTGGGACTACGGCATGAGCAGCAG
CCCTCACGTGCTGAGAAACAGGGCCCAGAGCGGCAGCGTGCCCCAGTTCAAGAAAGTGGTGTTCCAGG
AATTCACAGACGGCAGCTTCACCCAGCCTCTGTACCGCGGCGAGCTGAATGAGCACCTGGGACTGCTG
GGCCCCTATATCAGAGCCGAAGTGGAAGATAACATCATGGTCACCTTCCGGAATCAGGCCTCCCGGCC
CTACAGCTTCTACAGCTCCCTGATCAGCTACGAAGAGGACCAGAGACAGGGCGCTGAGCCCCGGAAGA
ACTTCGTGAAGCCCAACGAGACTAAGACCTACTTTTGGAAGGTGCAGCACCACATGGCCCCTACAAAG
GACGAGTTCGACTGCAAGGCCTGGGCCTACTTCTCCGATGTGGACCTGGAAAAGGACGTGCACTCTGG
GCTGATCGGCCCCCTGCTCGTGTGCCACACCAACACCCTGAATCCCGCCCACGGCAGACAAGTGACAG
TGCAGGAATTCGCCCTGTTCTTCACCATCTTCGACGAAACAAAGAGCTGGTACTTCACCGAAAACATG
GAAAGAAACTGCCGGGCTCCCTGCAACATCCAGATGGAAGATCCCACCTTCAAAGAGAACTACCGGTT
CCACGCCATCAACGGCTACATCATGGACACACTGCCCGGCCTCGTGATGGCTCAGGATCAGCGGATCC
GGTGGTATCTGCTGTCCATGGGCTCCAACGAGAACATCCACAGCATCCACTTCAGCGGCCACGTGTTC
ACCGTGCGGAAAAAAGAAGAGTACAAAATGGCCCTGTACAACCTGTACCCTGGGGTGTTCGAGACAGT
GGAAATGCTGCCCAGCAAGGCCGGCATCTGGCGGGTGGAATGTCTGATCGGCGAGCATCTGCACGCTG
GGATGAGCACACTGTTTCTGGTGTACAGCAACAAGTGCCAGACACCTCTGGGCATGGCCTCTGGCCAC
ATCCGGGACTTTCAGATCACAGCCAGCGGCCAGTATGGCCAGTGGGCCCCAAAACTGGCCAGACTGCA
CTACAGCGGCAGCATCAACGCCTGGTCCACCAAAGAGCCCTTCAGCTGGATCAAGGTGGACCTGCTGG
CTCCCATGATCATCCACGGAATCAAGACCCAGGGCGCCAGACAGAAGTTCAGCAGCCTGTACATCAGC
CAGTTCATCATCATGTACAGCCTGGACGGCAAGAAGTGGCAGACCTACCGGGGCAATAGCACCGGCAC
CCTGATGGTGTTCTTCGGCAACGTGGACTCCAGCGGCATTAAGCACAACATCTTCAACCCCCCCATCA
TTGCCCGGTACATCCGGCTGCACCCCACCCACTACAGCATCCGGTCCACCCTGAGAATGGAACTGATG
GGCTGCGACCTGAACTCCTGCAGCATGCCCCTGGGGATGGAAAGCAAGGCCATCTCCGACGCCCAGAT
CACCGCCTCCAGCTACTTCACCAACATGTTCGCCACCTGGTCCCCATCCAAGGCCCGGCTGCATCTGC
AGGGCAGAAGCAATGCTTGGAGGCCCCAAGTGAACAACCCCAAAGAATGGCTGCAGGTGGACTTCCAG
AAAACCATGAAAGTGACCGGCGTGACCACCCAGGGCGTGAAGTCTCTGCTGACCTCTATGTACGTGAA
AGAGTTCCTGATCTCCAGCAGCCAGGACGGCCACCAGTGGACCCTGTTTTTCCAGAACGGCAAAGTGA
AAGTGTTTCAGGGGAACCAGGACTCCTTCACCCCCGTCGTGAATAGCCTGGACCCTCCACTGCTGACC
AGATACCTGCGGATCCACCCTCAGAGTTGGGTGCACCAGATTGCTCTGCGGATGGAAGTGCTGGGATG
CGAGGCCCAGGACCTGTACTGA

-continued

Codon-optimized factor VIII cDNA, aka CO2

(SEQ ID NO: 11)

ATGCAGATCGAGCTGTCTACCTGCTTCTTCCTGTGCCTGCTGCGGTTCTGCTTTAGCGCTACTAGACG

CTACTACCTGGGCGCCGTGGAACTGAGCTGGGACTATATGCAGTCAGACCTGGGCGAGCTGCCCGTGG

ACGCTAGATTCCCACCTAGAGTGCCTAAGAGCTTCCCCTTTAACACCTCCGTGGTCTATAAGAAAACC

CTGTTCGTCGAGTTCACCGATCACCTGTTTAATATCGCTAAGCCTAGACCCCCCTGGATGGGCCTGCT

GGGCCCTACTATTCAGGCCGAGGTCTACGACACCGTCGTGATCACCCTGAAGAATATGGCTAGTCACC

CCGTCAGCCTGCACGCCGTGGGCGTCAGCTACTGGAAGGCTAGCGAGGGCGCCGAGTACGACGATCAG

ACTAGTCAGCGCGAGAAAGAGGACGACAAAGTCTTTCCTGGCGGCTCTCACACCTACGTGTGGCAGGT

CCTGAAAGAAAACGGCCCTATGGCTAGCGACCCCCTGTGCCTGACCTATAGCTACCTGAGTCACGTGG

ACCTGGTCAAGGACCTGAATAGCGGCCTGATCGGCGCCCTGCTCGTGTGTAGAGAGGGCTCACTGGCT

AAAGAGAAAACTCAGACCCTGCACAAGTTTATCCTGCTGTTCGCCGTGTTCGACGAGGGCAAGAGCTG

GCACTCAGAGACTAAGAATAGCCTGATGCAGGATAGGGACGCCGCTAGCGCTAGAGCCTGGCCTAAGA

TGCACACCGTGAACGGCTACGTGAACAGATCACTGCCCGGACTGATCGGCTGTCACCGGAAGTCCGTC

TACTGGCACGTGATCGGAATGGGCACTACCCCCGAGGTGCACTCTATCTTTCTGGAAGGCCACACCTT

CCTCGTCAGAAATCACCGGCAGGCTAGCCTCGAGATTAGCCCTATCACCTTCCTGACCGCTCAGACAC

TGCTGATGGACCTGGGCCAGTTCCTGCTGTTTTGTCACATTAGCTCTCACCAGCACGACGGGATGGAA

GCCTACGTGAAAGTGGATAGCTGCCCCGAGGAACCTCAGCTGAGAATGAAGAACAACGAGGAAGCCGA

GGATTACGACGACGACCTGACCGATAGCGAGATGGACGTCGTCAGATTCGACGACGATAACTCACCTA

GCTTTATTCAGATTAGATCAGTGGCTAAGAAGCACCCTAAGACCTGGGTGCACTATATCGCCGCCGAG

GAAGAGGACTGGGACTACGCCCCTCTGGTGCTGGCCCCCGACGATAGAAGCTATAAGTCTCAGTACCT

GAACAACGGCCCTCAGCGGATCGGCCGGAAGTATAAGAAAGTGCGGTTTATGGCCTACACCGACGAAA

CCTTCAAGACTAGAGAGGCTATTCAGCACGAGTCAGGGATCCTGGGCCCCCTGCTCTACGGCGAAGTG

GGCGACACCCTGCTGATTATCTTTAAGAATCAGGCTAGTAGGCCCTATAATATCTACCCCCACGGAAT

CACCGACGTGCGGCCCCTCTACTCTAGACGGCTGCCTAAGGGCGTGAAGCACCTGAAGGACTTCCCTA

TTCTGCCCGGCGAGATCTTTAAGTACAAGTGGACCGTGACCGTCGAGGACGGCCCTACTAAGTCCGAC

CCTCGGTGCCTGACTAGGTACTACTCTAGCTTCGTGAATATGGAACGGGACCTGGCTAGCGGACTGAT

TGGCCCTCTGCTGATCTGCTACAAAGAATCAGTGGATCAGCGGGGCAATCAGATTATGAGCGATAAGC

GGAACGTGATCCTGTTTAGTGTGTTTGACGAGAATAGGTCCTGGTATCTGACCGAGAATATCCAGCGG

TTCCTGCCTAACCCTGCCGGCGTGCAGCTGGAAGATCCCGAGTTTCAGGCTAGCAATATTATGCACTC

TATTAACGGATACGTGTTCGATAGCCTGCAGCTGAGCGTGTGCCTGCACGAGGTGGCCTACTGGTATA

TCCTGTCTATCGGCGCTCAGACCGACTTCCTGAGCGTGTTCTTTAGCGGCTACACCTTTAAGCACAAG

ATGGTCTACGAGGATACCCTGACCCTGTTCCCCTTTAGCGGCGAAACCGTGTTTATGTCTATGGAAAA

CCCCGGCCTGTGGATCCTGGGGTGTCACAATAGCGACTTTAGGAATAGAGGAATGACCGCCCTGCTGA

AAGTGTCTAGCTGCGATAAGAACACCGGCGACTATTACGAGGACTCTTACGAGGATATTAGCGCCTAC

CTGCTGTCTAAGAACAACGCTATCGAGCCTAGAAGCTTCAGTCAGAACCCCCCCGTGCTGAAGCGGCA

CCAGAGAGAGATCACTAGAACTACCCTGCAGAGCGACCAGGAAGAGATCGACTACGACGACACTATTA

GCGTCGAGATGAAGAAAGAGGATTTCGATATCTACGACGAGGACGAGAACCAGTCACCTAGATCCTTC

CAGAAGAAAACTAGGCACTACTTTATTGCCGCCGTCGAGCGGCTGTGGGACTACGGAATGAGTTCTAG

CCCTCACGTGCTGAGAAATAGGGCTCAGTCAGGCTCAGTGCCTCAGTTCAAGAAAGTGGTGTTCCAGG

AATTCACCGACGGCAGCTTCACTCAGCCCCTCTATAGGGGCGAGCTGAACGAGCACCTGGGACTGCTG

GGACCTTATATTAGAGCCGAAGTCGAGGACAATATTATGGTCACCTTTAGGAACCAGGCCTCTAGGCC

-continued

CTACAGCTTCTACTCTAGCCTGATCAGCTACGAGGAAGATCAGCGGCAGGGGGCCGAACCTAGAAAGA

ACTTCGTGAAGCCTAACGAGACTAAGACCTACTTCTGGAAGGTGCAGCACCACATGGCCCCTACTAAG

GACGAGTTCGACTGTAAAGCCTGGGCCTACTTTAGCGACGTGGACCTCGAGAAGGACGTGCACTCAGG

GCTGATCGGACCTCTGCTCGTCTGTCACACTAACACCCTGAACCCCGCTCACGGCCGGCAGGTCACAG

TGCAGGAATTCGCCCTGTTCTTCACTATCTTCGACGAAACTAAGAGCTGGTACTTCACAGAGAATATG

GAAAGAAACTGTAGGGCCCCCTGTAATATTCAGATGGAAGATCCTACCTTTAAAGAGAACTATAGGTT

TCACGCTATTAACGGCTATATTATGGACACCCTGCCCGGCCTCGTGATGGCTCAGGATCAGCGGATTA

GGTGGTATCTGCTGTCTATGGGCTCTAACGAGAATATTCACTCTATTCACTTTAGCGGCCACGTGTTC

ACCGTCCGGAAGAAAGAAGAGTATAAGATGGCCCTCTATAACCTCTACCCCGGCGTGTTCGAGACAGT

GGAAATGCTGCCTAGTAAAGCCGGAATCTGGCGGGTCGAGTGTCTGATCGGCGAGCACCTCCACGCCG

GAATGAGCACCCTGTTTCTGGTCTACTCTAACAAGTGTCAGACCCCTCTGGGAATGGCTAGCGGCCAC

ATTAGAGACTTTCAGATCACCGCTAGCGGACAGTACGGCCAGTGGGCCCCTAAGCTGGCTAGACTGCA

CTATAGCGGATCTATCAACGCCTGGTCTACCAAAGAGCCCTTTAGCTGGATTAAGGTGGACCTGCTGG

CCCCTATGATTATTCACGGGATTAAGACTCAGGGCGCTAGGCAGAAGTTTAGTAGCCTCTATATTAGT

CAGTTTATCATTATGTATAGCCTGGACGGCAAGAAGTGGCAGACCTATAGAGGCAATAGCACCGGCAC

CCTGATGGTGTTCTTCGGCAACGTGGACTCTAGCGGGATCAAGCACAATATCTTTAACCCCCCTATTA

TCGCTAGATATATTAGGCTGCACCCTACTCACTACTCTATTAGGTCTACCCTGAGGATGGAACTGATG

GGCTGCGATCTGAATAGCTGCTCTATGCCCCTGGGGATGGAATCTAAGGCTATTAGCGACGCTCAGAT

CACAGCCTCTAGCTACTTCACTAATATGTTCGCTACCTGGTCCCCTAGCAAGGCCCGGCTGCACCTCC

AGGGCAGATCTAACGCTTGGCGGCCTCAGGTCAACAACCCTAAAGAGTGGCTGCAGGTCGACTTTCAG

AAAACTATGAAGGTCACCGGCGTGACCACTCAGGGCGTGAAATCACTGCTGACCTCTATGTACGTGAA

AGAGTTCCTGATTAGCTCTAGCCAGGACGGCCACCAGTGGACCCTGTTCTTTCAGAACGGCAAAGTGA

AAGTGTTTCAGGGCAATCAGGATAGCTTCACCCCCGTGGTCAATAGCCTGGATCCCCCACTGCTGACT

AGATACCTGAGAATTCACCCTCAGTCTTGGGTGCACCAGATCGCCCTGAGAATGGAAGTCCTGGGCTG

TGAAGCTCAGGACCTCTACTAA

Certain Definitions/Abbreviations Used

SQ and BDD: FVIII with B domain deletion

TTRm: TTR promoter with 4 mutations, from TAmGTGTAG to TATTGACTTAG

CO and CO3: codon optimized FVIII nucleic acid variant, set forth as SEQ ID NO:1

CO1: codon optimized FVIII nucleic acid variant, set forth as SEQ ID NO:10

CO2: codon optimized FVIII nucleic acid variant, set forth as SEQ ID NO:11

Prep designations in Table 3 refer to 5 separate vector preparations of CO/CO3.

hFVIII-RH: Arg to His substitution at position 1645 of human FVIII

Δ4: deletion of amino acids 1645 to 1648 of FVIII

Δ1645: deletion of amino acid 1645 (Arg) of FVIII

Δ2: deletion of amino acids 1645 and 1646 of FVIII

Δ3: deletion of amino acids 1645 to 1647 of FVIII

Δ1648: deletion of amino acid 1648 of FVIII

While certain of the embodiments of the invention have been described and specifically exemplified above, it is not intended that the invention be limited to such embodiments. Various modifications may be made thereto without departing from the scope and spirit of the invention, as set forth in the following claims.

What is claimed is:

1. A Factor VIII (FVIII) encoding nucleic acid variant, wherein nucleic acid variant has one or more leucine codons changed to CTG compared to TTA, TTG, CTT, CTC or CTA in wild type FVIII, wherein said nucleic acid variant has at least 50% GC content, wherein the nucleic acid variant is at least 94% identical to the sequence of SEQ ID NO:1 and wherein the FVIII encoded by said nucleic acid variant exhibits greater expression when compared to wild type FVIII expression.

2. The Factor VIII (FVIII) encoding nucleic acid variant of claim 1, wherein the FVIII encoded by said nucleic acid variant comprises a B domain deletion and exhibits greater expression when compared to wild type FVIII comprising a B domain deletion expression.

3. The variant FVIII as claimed in claim 2, wherein said nucleic acid variant is more efficiently packaged into an adenovirus-associated virus (AAV) vector.

4. The variant FVIII as claimed in claim 2, wherein said FVIII encoded by said nucleic acid variant exhibits greater biological activity when compared to wild type FVIII or when compared to wild type FVIII comprising a B domain deletion.

5. The variant FVIII as claimed in claim 2, wherein said biological activity is determined by a clotting assay or reduced bleeding in a FVIII assay or FVIII deficiency model.

6. The variant FVIII as claimed in claim 2, wherein 2-5, 5-10, 10-20, 20-50, 50-100, 100-250, 250-500, 500-750 or 750-850 of the leucine codons are CTG leucine codons.

7. The variant FVIII as claimed in claim 2, wherein at least 85% of the codons of said nucleic acid variant are CTG leucine codons.

8. The variant FVIII as claimed in claim 2, wherein all leucine codons of said nucleic acid variant are CTG leucine codons.

9. The variant FVIII as claimed in claim 2, wherein said nucleic acid variant has one or more AAG lysine codons compared to AAA lysine codons in wild type FVIII.

10. The variant FVIII as claimed in claim 2, wherein said nucleic acid variant has between about 50-59%, or 50-56%, or 50-53% GC content.

11. The variant FVIII as claimed in claim 2, wherein said nucleic acid variant is at least 95% identical to wild type human FVIII nucleic acid comprising a B domain deletion.

12. The variant FVIII as claimed in claim 2, wherein said nucleic acid variant is wild type FVIII comprising a B domain deletion is human FVIII.

13. The Factor VIII (FVIII) encoding nucleic acid variant as claimed in claim 1, wherein said nucleic acid variant comprises any of SEQ ID NOs:1-7.

14. The variant FVIII as claimed in claim 2, wherein 1, 2, 3 or all 4 of the codons encoding the PACE/furin cleavage site is/are deleted.

15. The variant FVIII as claimed in claim 2, wherein 1, 2, 3 or all 4 of the codons encoding the PACE/furin cleavage site set forth as HHQR or RHQR from positions 1645-1648 is/are deleted.

16. An expression vector comprising the variant FVIII of claim 2.

17. The expression vector of claim 16, selected from the group consisting of an adenovirus-associated virus (AAV) vector, a retroviral vector, an adenoviral vector, a plasmid, or a lentiviral vector.

18. The expression vector of claim 17, wherein said AAV vector comprises an AAV1, AAV2, AAV3, AAV4, AAV5, AAV6, AAV7, AAV8, AAV9, AAV10, AAV11, Rh10, Rh74 or AAV-2i8 AAV serotype.

19. The expression vector of claim 16, further comprising at least one of an intron, an expression control element, one or more adeno-associated virus (AAV) inverted terminal repeats (ITRs) and a filler polynucleotide sequence.

20. The expression vector of claim 19, wherein the intron is within or flanks the variant FVIII, or wherein the expression control element is operably linked to the variant FVIII, or wherein the AAV ITR(s) flanks the 5' or 3' terminus of the variant FVIII, or wherein the filler polynucleotide sequence flanks the 5' or 3'terminus of the variant FVIII.

21. The expression vector of claim 19, wherein the expression control element comprises a constitutive or regulatable control element, or a tissue-specific expression control element or promoter.

22. The expression vector of claim 19, wherein the expression control element comprises an element that confers expression in liver.

23. The expression vector of claim 19, wherein the expression control element comprises a TTR promoter or mutant TTR promoter.

24. The expression vector of claim 19, wherein the ITR comprises one or more ITRs of any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof.

25. A host cell comprising the nucleic acid variant of claim 2.

26. An AAV vector comprising the nucleic acid variant of claim 2.

27. The AAV vector of claim 26, wherein the AAV vector comprises at least one of a VP1, VP2 and VP3 capsid sequence having 75% or more sequence identity to at least one of AAV1, AAV2, AAV3, AAV4, AAV5, AAV6, AAV7, AAV8, AAV9, AAV10, AAV11, Rh10, Rh74 or AAV-2i8 VP1, VP2 and VP3 sequences.

28. The AAV vector of claim 26, wherein the AAV vector comprises at least one of a VP1, VP2 and VP3 capsid sequence selected from any of: AAV1, AAV2, AAV3, AAV4, AAV5, AAV6, AAV7, AAV8, AAV9, AAV10, AAV11, Rh10, Rh74 and AAV-2i8 AAV serotypes.

29. A pharmaceutical composition comprising the AAV vector of claim 26.

30. A method for delivering or transferring a nucleic acid sequence into a mammal or a mammalian cell, comprising administering to said mammal or contacting said mammalian cell with the AAV vector of claim 17.

31. A method of treating a mammal in need of Factor VIII, comprising:

(a) providing the AAV vector of claim 26; and (b) administering an amount of the AAV vector of claim 26 to the mammal wherein said Factor VIII is expressed in the mammal.

32. The method of claim 31, wherein said Factor VIII is expressed at levels having a beneficial or therapeutic effect on the mammal.

33. The method of claim 31, wherein said Factor VIII is expressed in a cell, tissue or organ of said mammal.

34. The method of claim 31, wherein, the cell comprises a secretory cell.

35. The method of claim 31, wherein the cell comprises an endocrine cell or an endothelial cell.

36. The method of claim 31, wherein the cell comprises an hepatocyte, a sinusoidal endothelial cell, a megakaryocyte, a platelet or hematopoetic stem cell.

37. The method of claim 33, wherein the tissue or organ of said mammal comprises liver.

38. The method of claim 31, wherein the mammal produces an insufficient amount of Factor VIII protein, or a defective or aberrant Factor VIII protein.

39. The method of claim 31, wherein the mammal has hemophilia A.

40. The method of claim 31, wherein the AAV vector of claim 26 is delivered to said mammal or said patient intravenously, intraarterially, intramuscularly, subcutaneously, intra-cavity, or by intubation, or via catheter.

41. The method of claim 31, wherein said mammal or said patient is human.

42. An expression vector comprising:

(a) an expression control element comprising a mutant TTR promoter comprising SEQ ID NO:8; and (b) a Factor VIII (FVIII) encoding nucleic acid variant, wherein said nucleic acid variant has one or more leucine codons changed to CTG compared to TTA, TTG, CTT, CTC or CTA in wild type FVIII, wherein said nucleic acid variant has at least 50% GC content, wherein said nucleic acid variant is at least 80% identical to the sequence of SEQ ID NO:1, and wherein the FVIII encoded by said nucleic acid variant comprises a B domain deletion that exhibits greater expression when compared to wild type FVIII comprising a B domain deletion expression.

43. The expression vector of claim 42, further comprising at least one of an intron, one or more adeno-associated (AAV) inverted repeats (ITRs), and a filler polynucleotide sequence.

44. The expression vector of claim 42, wherein:

(a) said nucleic acid variant is more efficiently packaged into an adenovirus-associated virus (AAV) vector;

(b) said FVIII encoded by said nucleic acid variant exhibits greater biological activity when compared to wild type FVIII or when compared to wild type FVIII comprising a B domain deletion;

(c) 2-5, 5-10, 10-20, 20-50, 50-100, 100-250, 250-500, 500-750 or 750-850 of the leucine codons of said nucleic acid variant are CTG leucine codons;

(d) at least 85% of the codons of said nucleic acid variant are CTG leucine codons;

(e) all leucine codons of said nucleic acid variant are CTG leucine codons;

(f) said nucleic acid variant has one or more AAG lysine codons compared to AAA lysine codons in wild type FVIII;

(g) said nucleic acid variant has between about 50-59%, or 50-56%, or 50-53% GC content;

(h) said nucleic acid variant is at least 95% identical to wild type human FVIII nucleic acid comprising a B domain deletion;

(i) said nucleic acid variant is wild type FVIII comprising a B domain deletion is human FVIII;

(j) said nucleic acid variant comprises any of SEQ ID NOs:1-7;

(k) 1, 2, 3 or all 4 of the codons encoding the PACE/furin cleavage site in said FVIII encoded by said nucleic acid variant is/are deleted; or (l) 1, 2, 3 or all 4 of the codons encoding the PACE/furin cleavage site set forth as HHQR or RHQR from positions 1645-1648 in said FVIII encoded by said nucleic acid variant is/are deleted.

45. The expression vector of claim 42, wherein said expression vector is selected from the group consisting of an adenovirus-associated virus (AAV) vector, a retroviral vector, an adenoviral vector, a plasmid, or a lentiviral vector.

46. The expression vector of claim 45, wherein said AAV vector comprises:

(a) an AAV1, AAV2, AAV3, AAV4, AAV5, AAV6, AAV7, AAV8, AAV9, AAV10, AAV11, Rh10, Rh74 or AAV-2i8 AAV serotype;

(b) at least one of a VP1, VP2 and VP3 capsid sequence having 75% or more sequence identity to at least one of AAV1, AAV2, AAV3, AAV4, AAV5, AAV6, AAV7, AAV8, AAV9, AAV10, AAV11, Rh10, Rh74 or AAV-2i8 VP1, VP2 and VP3 sequences; or (c) at least one of a VP1, VP2 and VP3 capsid sequence selected from any of: AAV1, AAV2, AAV3, AAV4, AAV5, AAV6, AAV7, AAV8, AAV9, AAV10, AAV11, Rh10, Rh74 and AAV-2i8 AAV serotypes.

47. The expression vector of claim 43, wherein the intron is within or flanks the variant FVIII, or wherein the expression control element is operably linked to the variant FVIII, or wherein the AAV ITR(s) flanks the 5' or 3' terminus of the variant FVIII, or wherein the filler polynucleotide sequence flanks the 5' or 3'terminus of the variant FVIII.

48. The expression vector of claim 43, wherein the ITR comprises one or more ITRs of any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof.

49. A host cell comprising the expression vector of claim 42.

50. A pharmaceutical composition comprising the expression vector of claim 42.

* * * * *

UNITED STATES PATENT AND TRADEMARK OFFICE
CERTIFICATE OF CORRECTION

PATENT NO. : 11,014,975 B2
APPLICATION NO. : 15/503120
DATED : May 25, 2021
INVENTOR(S) : Denise Sabatino, Katherine A. High and Liron Elkouby It is certified that error appears in the above-identified patent and that said Letters Patent is hereby corrected as shown below:

In the Claims

At Column 115, Line 56 Claim 1, please amend as follows:
1. A Factor VIII (FVIII) encoding nucleic acid variant, wherein said nucleic acid variant has one or more leucine codons changed to CTG compared to TTA, TTG, CTT, CTC or CTA in wild type FVIII, wherein said nucleic acid variant has at least 50% GC content, wherein the nucleic acid variant is at least 94% identical to the sequence of SEQ ID NO:1 and wherein the FVIII encoded by said nucleic acid variant exhibits greater expression when compared to wild type FVIII expression.

At Column 117, Line 20 Claim 12, please amend as follows:
12. The variant FVIII as claimed in claim 2, wherein said nucleic acid variant is wild type FVIII comprising a B domain deletion that is human FVIII.

At Column 117, Line 35 Claim 17, please amend as follows:
17. The expression vector of claim 16, selected from the group consisting of an adenovirus-associated virus (AAV) vector, a retroviral vector, an adenoviral vector, a plasmid, and a lentiviral vector.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 11

<210> SEQ ID NO 1
<211> LENGTH: 4374
<212> TYPE: DNA
<213> ORGANISM: Adeno-associated virus

<400> SEQUENCE: 1

-continued

```
atgcagattg agctgtcaac ttgctttttc ctgtgcctgc tgagattttg tttttccgct     60
actagaagat actacctggg ggctgtggaa ctgtcttggg attacatgca gagtgacctg    120
ggagagctgc cagtggacgc acgatttcca cctagagtcc ctaaatcatt ccccttcaac    180
accagcgtgg tctataagaa aacactgttc gtggagttta ctgatcacct gttcaacatc    240
gctaagcctc ggccaccctg gatgggactg ctgggaccaa caatccaggc agaggtgtac    300
gacaccgtgg tcattacact gaaaaacatg gcctcacacc ccgtgagcct gcatgctgtg    360
ggcgtcagct actggaaggc ttccgaaggg gcagagtatg acgatcagac ttcccagaga    420
gaaaaagagg acgataaggt gtttcctggc gggtctcata cctatgtgtg gcaggtcctg    480
aaagagaatg gccccatggc ttccgaccct ctgtgcctga cctactctta tctgagtcac    540
gtggacctgg tcaaggatct gaacagcgga ctgatcggag cactgctggt gtgtagggaa    600
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagagg caccagcgcg agatcacccg cactaccctg   2340
```

-continued cagagtgatc aggaagagat cgactacgac gatacaattt ctgtggaaat gaagaaagag 2400
gacttcgata tctatgacga agatgagaac cagagtcctc gatcattcca gaagaaaacc 2460
cggcattact ttattgctgc agtggagcgc ctgtgggatt atggcatgtc ctctagtcct 2520
cacgtgctgc gaaatcgggc ccagtcaggg agcgtcccac agttcaagaa agtggtcttc 2580
caggagttta cagacggatc ctttactcag ccactgtacc ggggcgaact gaacgagcac 2640
ctggggctgc tgggacccta tatcagagct gaagtggagg ataacattat ggtcaccttc 2700
agaaatcagg catctaggcc ttacagtttt tattcaagcc tgatctctta cgaagaggac 2760
cagaggcagg gagcagaacc acgaaaaaac ttcgtgaagc ctaatgagac caaaacatac 2820
ttttggaagg tgcagcacca tatggcccca acaaaagacg aattcgattg caaggcatgg 2880
gcctattttt ctgacgtgga tctggagaag gacgtccaca gtggcctgat cgggccactg 2940
ctggtgtgtc atactaacac cctgaatccc gcacacggca ggcaggtcac tgtccaggaa 3000
ttcgccctgt tctttaccat ctttgatgag acaaaaagct ggtacttcac cgaaaacatg 3060
gagcgaaatt gccgggctcc atgtaatatt cagatggaag accccacatt caaggagaac 3120
taccgctttc atgccatcaa tgggtatatt atggatactc tgcccggact ggtcatggct 3180
caggaccaga gaatcaggtg gtacctgctg agcatggggt ccaacgagaa tatccactca 3240
attcatttca gcggacacgt gtttactgtc cggaagaaag aagagtataa aatggccctg 3300
tacaacctgt atcccggcgt gttcgaaacc gtcgagatgc tgcctagcaa ggcagggatc 3360
tggagagtgg aatgcctgat tggggagcac ctgcatgccg gaatgtctac cctgtttctg 3420
gtgtacagta ataagtgtca gacacccctg ggatggcttc ccggacatat ccgggatttc 3480
cagattaccg catctggaca gtacggccag tgggccccta agctggctag actgcactat 3540
tccgggtcta tcaacgcttg gtccacaaaa gagcctttct cttggattaa ggtggacctg 3600
ctggcaccaa tgatcattca tggcatcaaa actcaggggg ccaggcagaa gttctcctct 3660
ctgtacatct cacagtttat catcatgtac agcctggatg gcaagaaatg gcagacatac 3720
cgcggcaata gcacagggac tctgatggtg ttctttggca acgtggacag ttcagggatc 3780
aagcacaaca ttttcaatcc ccctatcatt gctagataca tcaggctgca cccaacccat 3840
tattctattc gaagtacact gcggatggaa ctgatggggt gcgatctgaa cagttgttca 3900
atgcccctgg gaatggagtc caaggcaatc tctgacgccc agattaccgc tagctcctac 3960
ttcactaata tgtttgctac ctggagcccc tccaaagcac gactgcatct gcagggacga 4020
agcaacgcat ggcgaccaca ggtgaacaat cccaaggagt ggctgcaggt cgattttcag 4080
aaaactatga aggtgaccgg agtcacaact cagggcgtga aaagtctgct gacctcaatg 4140
tacgtcaagg agttcctgat ctctagttca caggacggcc accagtggac actgttcttt 4200
cagaacggaa aggtgaaagt cttccagggc aatcaggatt cctttacacc tgtggtcaac 4260
tctctggacc cacccctgct gactcgctac ctgcgaatcc acccacagtc ctgggtgcat 4320
cagattgcac tgagaatgga agtcctgggc tgcgaggccc aggacctgta ttga 4374

<210> SEQ ID NO 2
<211> LENGTH: 4374
<212> TYPE: DNA
<213> ORGANISM: Adeno-associated virus

<400> SEQUENCE: 2
atgcagattg agctgtcaac ttgctttttc ctgtgcctgc tgagattttg tttttccgct 60
actagaagat actacctggg ggctgtggaa ctgtcttggg attacatgca gagtgacctg 120

-continued

```
ggagagctgc cagtggacgc acgatttcca cctagagtcc ctaaatcatt ccccttcaac    180
accagcgtgg tctataagaa aacactgttc gtggagttta ctgatcacct gttcaacatc    240
gctaagcctc ggccaccctg gatgggactg ctgggaccaa caatccaggc agaggtgtac    300
gacaccgtgg tcattacact gaaaaacatg gcctcacacc ccgtgagcct gcatgctgtg    360
ggcgtcagct actggaaggc ttccgaaggg gcagagtatg acgatcagac ttcccagaga    420
gaaaaagagg acgataaggt gtttcctggc gggtctcata cctatgtgtg gcaggtcctg    480
aaagagaatg gccccatggc ttccgaccct ctgtgcctga cctactctta tctgagtcac    540
gtggacctgg tcaaggatct gaacagcgga ctgatcggag cactgctggt gtgtagggaa    600
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagcac caccagcgcg agatcacccg cactaccctg   2340
cagagtgatc aggaagagat cgactacgac gatacaattt ctgtggaaat gaagaaagag   2400
gacttcgata tctatgacga agatgagaac cagagtcctc gatcattcca gaagaaaacc   2460
```

-continued

```
cggcattact ttattgctgc agtggagcgc ctgtgggatt atggcatgtc ctctagtcct   2520

cacgtgctgc gaaatcgggc ccagtcaggg agcgtcccac agttcaagaa agtggtcttc   2580

caggagttta cagacggatc ctttactcag ccactgtacc ggggcgaact gaacgagcac   2640

ctggggctgc tgggacccta tatcagagct gaagtggagg ataacattat ggtcaccttc   2700

agaaatcagg catctaggcc ttacagtttt tattcaagcc tgatctctta cgaagaggac   2760

cagaggcagg gagcagaacc acgaaaaaac ttcgtgaagc ctaatgagac caaaacatac   2820

ttttggaagg tgcagcacca tatggcccca acaaaagacg aattcgattg caaggcatgg   2880

gcctattttt ctgacgtgga tctggagaag gacgtccaca gtggcctgat cgggccactg   2940

ctggtgtgtc atactaacac cctgaatccc gcacacggca ggcaggtcac tgtccaggaa   3000

ttcgccctgt tctttaccat ctttgatgag acaaaaagct ggtacttcac cgaaaacatg   3060

gagcgaaatt gccgggctcc atgtaatatt cagatggaag accccacatt caaggagaac   3120

taccgctttc atgccatcaa tgggtatatt atggatactc tgcccggact ggtcatggct   3180

caggaccaga gaatcaggtg gtacctgctg agcatggggt ccaacgagaa tatccactca   3240

attcatttca gcggacacgt gtttactgtc cggaagaaag aagagtataa aatggccctg   3300

tacaacctgt atcccggcgt gttcgaaacc gtcgagatgc tgcctagcaa ggcagggatc   3360

tggagagtgg aatgcctgat tggggagcac ctgcatgccg gaatgtctac cctgtttctg   3420

gtgtacagta ataagtgtca gacacccctg ggatggcttc ccggacatat ccgggatttc   3480

cagattaccg catctggaca gtacggccag tgggccccta agctggctag actgcactat   3540

tccgggtcta tcaacgcttg gtccacaaaa gagccttttct cttggattaa ggtggacctg   3600

ctggcaccaa tgatcattca tggcatcaaa actcaggggg ccaggcagaa gttctcctct   3660

ctgtacatct cacagtttat catcatgtac agcctggatg gcaagaaatg gcagacatac   3720

cgcggcaata gcacagggac tctgatggtg ttctttggca acgtggacag ttcagggatc   3780

aagcacaaca ttttcaatcc ccctatcatt gctagataca tcaggctgca cccaacccat   3840

tattctattc gaagtacact gcggatggaa ctgatggggt gcgatctgaa cagttgttca   3900

atgcccctgg gaatggagtc caaggcaatc tctgacgccc agattaccgc tagctcctac   3960

ttcactaata tgtttgctac ctggagcccc tccaaagcac gactgcatct gcagggacga   4020

agcaacgcat ggcgaccaca ggtgaacaat cccaaggagt ggctgcaggt cgattttcag   4080

aaaactatga aggtgaccgg agtcacaact cagggcgtga aaagtctgct gacctcaatg   4140

tacgtcaagg agttcctgat ctctagttca caggacggcc accagtggac actgttcttt   4200

cagaacggaa aggtgaaagt cttccagggc aatcaggatt cctttacacc tgtggtcaac   4260

tctctggacc cacccctgct gactcgctac ctgcgaatcc acccacagtc ctgggtgcat   4320

cagattgcac tgagaatgga agtcctgggc tgcgaggccc aggacctgta ttga         4374
```

<210> SEQ ID NO 3
<211> LENGTH: 4362
<212> TYPE: DNA
<213> ORGANISM: Adeno-associated virus

<400> SEQUENCE: 3

```
atgcagattg agctgtcaac ttgctttttc ctgtgcctgc tgagattttg tttttccgct     60

actagaagat actacctggg ggctgtggaa ctgtcttggg attacatgca gagtgacctg    120

ggagagctgc cagtggacgc acgatttcca cctagagtcc ctaaatcatt ccccttcaac    180

accagcgtgg tctataagaa aacactgttc gtggagttta ctgatcacct gttcaacatc    240
```

-continued

```
gctaagcctc ggccaccctg gatgggactg ctgggaccaa caatccaggc agaggtgtac    300
gacaccgtgg tcattacact gaaaaacatg gcctcacacc ccgtgagcct gcatgctgtg    360
ggcgtcagct actggaaggc ttccgaaggg gcagagtatg acgatcagac ttcccagaga    420
gaaaaagagg acgataaggt gtttcctggc gggtctcata cctatgtgtg gcaggtcctg    480
aaagagaatg gccccatggc ttccgaccct ctgtgcctga cctactctta tctgagtcac    540
gtggacctgg tcaaggatct gaacagcgga ctgatcggag cactgctggt gtgtagggaa    600
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaaggag atcacccgca ctaccctgca gagtgatcag   2340
gaagagatcg actacgacga tacaatttct gtggaaatga agaaagagga cttcgatatc   2400
tatgacgaag atgagaacca gagtcctcga tcattccaga agaaaacccg gcattacttt   2460
attgctgcag tggagcgcct gtgggattat ggcatgtcct ctagtcctca cgtgctgcga   2520
aatcgggccc agtcagggag cgtcccacag ttcaagaaag tggtcttcca ggagtttaca   2580
```

gacggatcct ttactcagcc actgtaccgg ggcgaactga acgagcacct ggggctgctg 2640
ggaccctata tcagagctga agtggaggat aacattatgg tcaccttcag aaatcaggca 2700
tctaggcctt acagttttta ttcaagcctg atctcttacg aagaggacca gaggcaggga 2760
gcagaaccac gaaaaaactt cgtgaagcct aatgagacca aaacatactt ttggaaggtg 2820
cagcaccata tggccccaac aaaagacgaa ttcgattgca aggcatgggc ctatttttct 2880
gacgtggatc tggagaagga cgtccacagt ggcctgatcg ggccactgct ggtgtgtcat 2940
actaacaccc tgaatcccgc acacggcagg caggtcactg tccaggaatt cgccctgttc 3000
tttaccatct ttgatgagac aaaaagctgg tacttcaccg aaaacatgga gcgaaattgc 3060
cgggctccat gtaatattca gatggaagac cccacattca aggagaacta ccgctttcat 3120
gccatcaatg ggtatattat ggatactctg cccggactgg tcatggctca ggaccagaga 3180
atcaggtggt acctgctgag catggggtcc aacgagaata tccactcaat tcatttcagc 3240
ggacacgtgt ttactgtccg gaagaaagaa gagtataaaa tggccctgta caacctgtat 3300
cccggcgtgt tcgaaaccgt cgagatgctg cctagcaagg cagggatctg gagagtggaa 3360
tgcctgattg gggagcacct gcatgccgga atgtctaccc tgtttctggt gtacagtaat 3420
aagtgtcaga cacccctggg gatggcttcc ggacatatcc gggatttcca gattaccgca 3480
tctggacagt acggccagtg ggcccctaag ctggctagac tgcactattc cgggtctatc 3540
aacgcttggt ccacaaaaga gcctttctct tggattaagg tggacctgct ggcaccaatg 3600
atcattcatg gcatcaaaac tcaggggggcc aggcagaagt tctcctctct gtacatctca 3660
cagtttatca tcatgtacag cctggatggc aagaaatggc agacataccg cggcaatagc 3720
acagggactc tgatggtgtt ctttggcaac gtggacagtt cagggatcaa gcacaacatt 3780
ttcaatcccc ctatcattgc tagatacatc aggctgcacc caacccatta ttctattcga 3840
agtacactgc ggatggaact gatggggtgc gatctgaaca gttgttcaat gcccctggga 3900
atggagtcca aggcaatctc tgacgcccag attaccgcta gctcctactt cactaatatg 3960
tttgctacct ggagcccctc caaagcacga ctgcatctgc agggacgaag caacgcatgg 4020
cgaccacagg tgaacaatcc caaggagtgg ctgcaggtcg attttcagaa aactatgaag 4080
gtgaccggag tcacaactca gggcgtgaaa agtctgctga cctcaatgta cgtcaaggag 4140
ttcctgatct ctagttcaca ggacggccac cagtggacac tgttctttca gaacggaaag 4200
gtgaaagtct tccagggcaa tcaggattcc tttacacctg tggtcaactc tctggaccca 4260
cccctgctga ctcgctacct gcgaatccac ccacagtcct gggtgcatca gattgcactg 4320
agaatggaag tcctgggctg cgaggcccag gacctgtatt ga 4362

<210> SEQ ID NO 4
<211> LENGTH: 4371
<212> TYPE: DNA
<213> ORGANISM: Adeno-associated virus

<400> SEQUENCE: 4
atgcagattg agctgtcaac ttgctttttc ctgtgcctgc tgagattttg tttttccgct 60
actagaagat actacctggg ggctgtggaa ctgtcttggg attacatgca gagtgacctg 120
ggagagctgc cagtggacgc acgatttcca cctagagtcc ctaaatcatt ccccttcaac 180
accagcgtgg tctataagaa aacactgttc gtggagttta ctgatcacct gttcaacatc 240
gctaagcctc ggccaccctg gatgggactg ctgggaccaa caatccaggc agaggtgtac 300
gacaccgtgg tcattacact gaaaaacatg gcctcacacc ccgtgagcct gcatgctgtg 360

```
ggcgtcagct actggaaggc ttccgaaggg gcagagtatg acgatcagac ttcccagaga    420
gaaaaagagg acgataaggt gtttcctggc gggtctcata cctatgtgtg gcaggtcctg    480
aaagagaatg gccccatggc ttccgaccct ctgtgcctga cctactctta tctgagtcac    540
gtggacctgg tcaaggatct gaacagcgga ctgatcggag cactgctggt gtgtagggaa    600
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagcac cagcgcgaga tcacccgcac taccctgcag   2340
agtgatcagg aagagatcga ctacgacgat acaatttctg tggaaatgaa gaaagaggac   2400
ttcgatatct atgacgaaga tgagaaccag agtcctcgat cattccagaa gaaaacccgg   2460
cattacttta ttgctgcagt ggagcgcctg tgggattatg gcatgtcctc tagtcctcac   2520
gtgctgcgaa atcgggccca gtcagggagc gtcccacagt tcaagaaagt ggtcttccag   2580
gagtttacag acggatcctt tactcagcca ctgtaccggg gcgaactgaa cgagcacctg   2640
gggctgctgg gaccctatat cagagctgaa gtggaggata acattatggt caccttcaga   2700
```

aatcaggcat ctaggcctta cagtttttat tcaagcctga tctcttacga agaggaccag 2760
aggcagggag cagaaccacg aaaaaacttc gtgaagccta atgagaccaa aacatacttt 2820
tggaaggtgc agcaccatat ggccccaaca aaagacgaat tcgattgcaa ggcatgggcc 2880
tatttttctg acgtggatct ggagaaggac gtccacagtg gcctgatcgg gccactgctg 2940
gtgtgtcata ctaacaccct gaatcccgca cacggcaggc aggtcactgt ccaggaattc 3000
gccctgttct ttaccatctt tgatgagaca aaaagctggt acttcaccga aaacatggag 3060
cgaaattgcc gggctccatg taatattcag atggaagacc ccacattcaa ggagaactac 3120
cgctttcatg ccatcaatgg gtatattatg gatactctgc ccggactggt catggctcag 3180
gaccagagaa tcaggtggta cctgctgagc atggggtcca acgagaatat ccactcaatt 3240
catttcagcg gacacgtgtt tactgtccgg aagaaagaag agtataaaat ggccctgtac 3300
aacctgtatc ccggcgtgtt cgaaaccgtc gagatgctgc ctagcaaggc agggatctgg 3360
agagtggaat gcctgattgg ggagcacctg catgccggaa tgtctaccct gtttctggtg 3420
tacagtaata agtgtcagac acccctgggg atggcttccg gacatatccg ggatttccag 3480
attaccgcat ctggacagta cggccagtgg gcccctaagc tggctagact gcactattcc 3540
gggtctatca acgcttggtc cacaaaagag cctttctctt ggattaaggt ggacctgctg 3600
gcaccaatga tcattcatgg catcaaaact caggggggcca ggcagaagtt ctcctctctg 3660
tacatctcac agtttatcat catgtacagc ctggatggca agaaatggca gacataccgc 3720
ggcaatagca cagggactct gatggtgttc tttggcaacg tggacagttc agggatcaag 3780
cacaacattt tcaatccccc tatcattgct agatacatca ggctgcaccc aacccattat 3840
tctattcgaa gtacactgcg gatggaactg atggggtgcg atctgaacag ttgttcaatg 3900
cccctgggaa tggagtccaa ggcaatctct gacgcccaga ttaccgctag ctcctacttc 3960
actaatatgt ttgctacctg gagcccctcc aaagcacgac tgcatctgca gggacgaagc 4020
aacgcatggc gaccacaggt gaacaatccc aaggagtggc tgcaggtcga ttttcagaaa 4080
actatgaagg tgaccggagt cacaactcag ggcgtgaaaa gtctgctgac ctcaatgtac 4140
gtcaaggagt tcctgatctc tagttcacag gacggccacc agtggacact gttctttcag 4200
aacggaaagg tgaaagtctt ccagggcaat caggattcct ttacacctgt ggtcaactct 4260
ctggacccac ccctgctgac tcgctacctg cgaatccacc cacagtcctg ggtgcatcag 4320
attgcactga gaatggaagt cctgggctgc gaggcccagg acctgtattg a 4371

<210> SEQ ID NO 5
<211> LENGTH: 4368
<212> TYPE: DNA
<213> ORGANISM: Adeno-associated virus

<400> SEQUENCE: 5
atgcagattg agctgtcaac ttgctttttc ctgtgcctgc tgagattttg tttttccgct 60
actagaagat actacctggg ggctgtggaa ctgtcttggg attacatgca gagtgacctg 120
ggagagctgc cagtggacgc acgatttcca cctagagtcc ctaaatcatt ccccttcaac 180
accagcgtgg tctataagaa aacactgttc gtggagttta ctgatcacct gttcaacatc 240
gctaagcctc ggccaccctg gatgggactg ctgggaccaa caatccaggc agaggtgtac 300
gacaccgtgg tcattacact gaaaaacatg gcctcacacc ccgtgagcct gcatgctgtg 360
ggcgtcagct actggaaggc ttccgaaggg gcagagtatg acgatcagac ttcccagaga 420
gaaaaagagg acgataaggt gtttcctggc gggtctcata cctatgtgtg gcaggtcctg 480

-continued

```
aaagagaatg gccccatggc ttccgaccct ctgtgcctga cctactctta tctgagtcac    540
gtggacctgg tcaaggatct gaacagcgga ctgatcggag cactgctggt gtgtagggaa    600
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagcag cgcgagatca cccgcactac cctgcagagt   2340
gatcaggaag agatcgacta cgacgataca atttctgtgg aaatgaagaa agaggacttc   2400
gatatctatg acgaagatga gaaccagagt cctcgatcat tccagaagaa aacccggcat   2460
tactttattg ctgcagtgga gcgcctgtgg gattatggca tgtcctctag tcctcacgtg   2520
ctgcgaaatc gggcccagtc agggagcgtc ccacagttca agaaagtggt cttccaggag   2580
tttacagacg gatcctttac tcagccactg taccggggcg aactgaacga gcacctgggg   2640
ctgctgggac cctatatcag agctgaagtg gaggataaca ttatggtcac cttcagaaat   2700
caggcatcta ggccttacag tttttattca agcctgatct cttacgaaga ggaccagagg   2760
cagggagcag aaccacgaaa aaacttcgtg aagcctaatg agaccaaaac atacttttgg   2820
```

```
aaggtgcagc accatatggc cccaacaaaa gacgaattcg attgcaaggc atgggcctat   2880

ttttctgacg tggatctgga gaaggacgtc cacagtggcc tgatcgggcc actgctggtg   2940

tgtcatacta acaccctgaa tcccgcacac ggcaggcagg tcactgtcca ggaattcgcc   3000

ctgttcttta ccatctttga tgagacaaaa agctggtact tcaccgaaaa catggagcga   3060

aattgccggg ctccatgtaa tattcagatg gaagacccca cattcaagga gaactaccgc   3120

tttcatgcca tcaatgggta tattatggat actctgcccg gactggtcat ggctcaggac   3180

cagagaatca ggtggtacct gctgagcatg ggtccaacg agaatatcca ctcaattcat   3240

ttcagcggac acgtgtttac tgtccggaag aaagaagagt ataaaatggc cctgtacaac   3300

ctgtatcccg gcgtgttcga aaccgtcgag atgctgccta gcaaggcagg gatctggaga   3360

gtggaatgcc tgattgggga gcacctgcat gccggaatgt ctaccctgtt tctggtgtac   3420

agtaataagt gtcagacacc cctggggatg gcttccggac atatccggga tttccagatt   3480

accgcatctg gacagtacgg ccagtgggcc cctaagctgg ctagactgca ctattccggg   3540

tctatcaacg cttggtccac aaaagagcct ttctcttgga ttaaggtgga cctgctggca   3600

ccaatgatca ttcatggcat caaaactcag gggccaggc agaagttctc ctctctgtac   3660

atctcacagt ttatcatcat gtacagcctg gatggcaaga aatggcagac ataccgcggc   3720

aatagcacag ggactctgat ggtgttcttt ggcaacgtgg acagttcagg gatcaagcac   3780

aacattttca atccccctat cattgctaga tacatcaggc tgcacccaac ccattattct   3840

attcgaagta cactgcggat ggaactgatg ggtgcgatc tgaacagttg ttcaatgccc   3900

ctgggaatgg agtccaaggc aatctctgac gcccagatta ccgctagctc ctacttcact   3960

aatatgtttg ctacctggag cccctccaaa gcacgactgc atctgcaggg acgaagcaac   4020

gcatggcgac cacaggtgaa caatcccaag gagtggctgc aggtcgattt tcagaaaact   4080

atgaaggtga ccggagtcac aactcagggc gtgaaaagtc tgctgacctc aatgtacgtc   4140

aaggagttcc tgatctctag ttcacaggac ggccaccagt ggacactgtt ctttcagaac   4200

ggaaaggtga aagtcttcca gggcaatcag gattccttta cacctgtggt caactctctg   4260

gacccacccc tgctgactcg ctacctgcga atccacccac agtcctgggt gcatcagatt   4320

gcactgagaa tggaagtcct gggctgcgag gcccaggacc tgtattga                4368
```

<210> SEQ ID NO 6
<211> LENGTH: 4365
<212> TYPE: DNA
<213> ORGANISM: Adeno-associated virus

<400> SEQUENCE: 6

```
atgcagattg agctgtcaac ttgctttttc ctgtgcctgc tgagattttg tttttccgct     60

actagaagat actacctggg ggctgtggaa ctgtcttggg attacatgca gagtgacctg    120

ggagagctgc cagtggacgc acgatttcca cctagagtcc ctaaatcatt ccccttcaac    180

accagcgtgg tctataagaa aacactgttc gtggagttta ctgatcacct gttcaacatc    240

gctaagcctc ggccaccctg gatgggactg ctgggaccaa caatccaggc agaggtgtac    300

gacaccgtgg tcattacact gaaaaacatg gcctcacacc ccgtgagcct gcatgctgtg    360

ggcgtcagct actggaaggc ttccgaaggg gcagagtatg acgatcagac ttcccagaga    420

gaaaaagagg acgataaggt gtttcctggc gggtctcata cctatgtgtg gcaggtcctg    480

aaagagaatg gccccatggc ttccgaccct ctgtgcctga cctactctta tctgagtcac    540

gtggacctgg tcaaggatct gaacagcgga ctgatcggag cactgctggt gtgtagggaa    600
```

-continued

```
gggagcctgg ctaaggagaa aacccagaca ctgcataagt tcattctgct gttcgccgtg    660
tttgacgaag gaaaatcatg gcacagcgag acaaagaata gtctgatgca ggaccgggat    720
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagcgc gagatcaccc gcactaccct gcagagtgat   2340
caggaagaga tcgactacga cgatacaatt tctgtggaaa tgaagaaaga ggacttcgat   2400
atctatgacg aagatgagaa ccagagtcct cgatcattcc agaagaaaac ccggcattac   2460
tttattgctg cagtggagcg cctgtgggat tatggcatgt cctctagtcc tcacgtgctg   2520
cgaaatcggg cccagtcagg gagcgtccca cagttcaaga aagtggtctt ccaggagttt   2580
acagacggat cctttactca gccactgtac cggggcgaac tgaacgagca cctggggctg   2640
ctgggaccct atatcagagc tgaagtggag gataacatta tggtcacctt cagaaatcag   2700
gcatctaggc cttacagttt ttattcaagc ctgatctctt acgaagagga ccagaggcag   2760
ggagcagaac cacgaaaaaa cttcgtgaag cctaatgaga ccaaaacata cttttggaag   2820
gtgcagcacc atatggcccc aacaaaagac gaattcgatt gcaaggcatg ggcctatttt   2880
tctgacgtgg atctggagaa ggacgtccac agtggcctga tcgggccact gctggtgtgt   2940
```

```
catactaaca ccctgaatcc cgcacacggc aggcaggtca ctgtccagga attcgccctg   3000

ttctttacca tctttgatga gacaaaaagc tggtacttca ccgaaaacat ggagcgaaat   3060

tgccgggctc catgtaatat tcagatggaa gaccccacat tcaaggagaa ctaccgcttt   3120

catgccatca atgggtatat tatggatact ctgcccggac tggtcatggc tcaggaccag   3180

agaatcaggt ggtacctgct gagcatgggg tccaacgaga atatccactc aattcatttc   3240

agcggacacg tgtttactgt ccggaagaaa gaagagtata aaatggccct gtacaacctg   3300

tatcccggcg tgttcgaaac cgtcgagatg ctgcctagca aggcagggat ctggagagtg   3360

gaatgcctga ttggggagca cctgcatgcc ggaatgtcta ccctgtttct ggtgtacagt   3420

aataagtgtc agacacccct ggggatggct tccggacata tccgggattt ccagattacc   3480

gcatctggac agtacggcca gtgggcccct aagctggcta gactgcacta ttccgggtct   3540

atcaacgctt ggtccacaaa agagcctttc tcttggatta aggtggacct gctggcacca   3600

atgatcattc atggcatcaa aactcagggg gccaggcaga agttctcctc tctgtacatc   3660

tcacagttta tcatcatgta cagcctggat ggcaagaaat ggcagacata ccgcggcaat   3720

agcacaggga ctctgatggt gttctttggc aacgtggaca gttcagggat caagcacaac   3780

attttcaatc cccctatcat tgctagatac atcaggctgc acccaaccca ttattctatt   3840

cgaagtacac tgcggatgga actgatgggg tgcgatctga acagttgttc aatgcccctg   3900

ggaatggagt ccaaggcaat ctctgacgcc cagattaccg ctagctccta cttcactaat   3960

atgtttgcta cctggagccc ctccaaagca cgactgcatc tgcagggacg aagcaacgca   4020

tggcgaccac aggtgaacaa tcccaaggag tggctgcagg tcgattttca gaaaactatg   4080

aaggtgaccg gagtcacaac tcagggcgtg aaaagtctgc tgacctcaat gtacgtcaag   4140

gagttcctga tctctagttc acaggacggc caccagtgga cactgttctt tcagaacgga   4200

aaggtgaaag tcttccaggg caatcaggat tcctttacac ctgtggtcaa ctctctggac   4260

ccacccctgc tgactcgcta cctgcgaatc cacccacagt cctgggtgca tcagattgca   4320

ctgagaatgg aagtcctggg ctgcgaggcc caggacctgt attga                   4365
```

<210> SEQ ID NO 7
<211> LENGTH: 4371
<212> TYPE: DNA
<213> ORGANISM: Adeno-associated virus

<400> SEQUENCE: 7

```
atgcagattg agctgtcaac ttgctttttc ctgtgcctgc tgagattttg tttttccgct     60

actagaagat actacctggg ggctgtggaa ctgtcttggg attacatgca gagtgacctg    120

ggagagctgc cagtggacgc acgatttcca cctagagtcc ctaaatcatt ccccttcaac    180

accagcgtgg tctataagaa aacactgttc gtggagttta ctgatcacct gttcaacatc    240

gctaagcctc ggccaccctg gatgggactg ctgggaccaa caatccaggc agaggtgtac    300

gacaccgtgg tcattacact gaaaaacatg gcctcacacc ccgtgagcct gcatgctgtg    360

ggcgtcagct actggaaggc ttccgaaggg gcagagtatg acgatcagac ttcccagaga    420

gaaaaagagg acgataaggt gtttcctggc gggtctcata cctatgtgtg gcaggtcctg    480

aaagagaatg gccccatggc ttccgaccct ctgtgcctga cctactctta tctgagtcac    540

gtggacctgg tcaaggatct gaacagcgga ctgatcggag cactgctggt gtgtagggaa    600

gggagcctgg ctaaggagaa aacccagaca ctgcataagt tcattctgct gttcgccgtg    660

tttgacgaag gaaaatcatg gcacagcgag acaaagaata gtctgatgca ggaccgggat    720
```

-continued

```
gccgcttcag ccagagcttg gcccaaaatg cacactgtga acggctacgt caatcgctca    780
ctgcctggac tgatcggctg ccaccgaaag agcgtgtatt ggcatgtcat cggaatgggc    840
accacacctg aagtgcactc cattttcctg gaggggcata cctttctggt ccgcaaccac    900
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagagg caccaggaga tcacccgcac taccctgcag   2340
agtgatcagg aagagatcga ctacgacgat acaatttctg tggaaatgaa gaaagaggac   2400
ttcgatatct atgacgaaga tgagaaccag agtcctcgat cattccagaa gaaaacccgg   2460
cattacttta ttgctgcagt ggagcgcctg tgggattatg gcatgtcctc tagtcctcac   2520
gtgctgcgaa atcgggccca gtcagggagc gtcccacagt tcaagaaagt ggtcttccag   2580
gagtttacag acggatcctt tactcagcca ctgtaccggg gcgaactgaa cgagcacctg   2640
gggctgctgg gaccctatat cagagctgaa gtggaggata acattatggt caccttcaga   2700
aatcaggcat ctaggcctta cagtttttat tcaagcctga tctcttacga agaggaccag   2760
aggcagggag cagaaccacg aaaaaacttc gtgaagccta atgagaccaa aacatacttt   2820
tggaaggtgc agcaccatat ggccccaaca aaagacgaat tcgattgcaa ggcatgggcc   2880
tatttttctg acgtggatct ggagaaggac gtccacagtg gcctgatcgg gccactgctg   2940
gtgtgtcata ctaacaccct gaatcccgca cacggcaggc aggtcactgt ccaggaattc   3000
gccctgttct ttaccatctt tgatgagaca aaaagctggt acttcaccga aaacatggag   3060
```

```
cgaaattgcc gggctccatg taatattcag atggaagacc ccacattcaa ggagaactac   3120
cgctttcatg ccatcaatgg gtatattatg gatactctgc ccggactggt catggctcag   3180
gaccagagaa tcaggtggta cctgctgagc atggggtcca acgagaatat ccactcaatt   3240
catttcagcg gacacgtgtt tactgtccgg aagaaagaag agtataaaat ggccctgtac   3300
aacctgtatc ccggcgtgtt cgaaaccgtc gagatgctgc ctagcaaggc agggatctgg   3360
agagtggaat gcctgattgg ggagcacctg catgccggaa tgtctaccct gtttctggtg   3420
tacagtaata agtgtcagac acccctgggg atggcttccg gacatatccg ggatttccag   3480
attaccgcat ctggacagta cggccagtgg gcccctaagc tggctagact gcactattcc   3540
gggtctatca acgcttggtc cacaaaagag cctttctctt ggattaaggt ggacctgctg   3600
gcaccaatga tcattcatgg catcaaaact caggggggcca ggcagaagtt ctcctctctg  3660
tacatctcac agtttatcat catgtacagc ctggatggca agaaatggca gacataccgc   3720
ggcaatagca cagggactct gatggtgttc tttggcaacg tggacagttc agggatcaag   3780
cacaacattt tcaatccccc tatcattgct agatacatca ggctgcaccc aacccattat   3840
tctattcgaa gtacactgcg gatggaactg atggggtgcg atctgaacag ttgttcaatg   3900
cccctgggaa tggagtccaa ggcaatctct gacgcccaga ttaccgctag ctcctacttc   3960
actaatatgt ttgctacctg gagcccctcc aaagcacgac tgcatctgca gggacgaagc   4020
aacgcatggc gaccacaggt gaacaatccc aaggagtggc tgcaggtcga ttttcagaaa   4080
actatgaagg tgaccggagt cacaactcag ggcgtgaaaa gtctgctgac ctcaatgtac   4140
gtcaaggagt tcctgatctc tagttcacag gacggccacc agtggacact gttctttcag   4200
aacggaaagg tgaaagtctt ccagggcaat caggattcct ttacacctgt ggtcaactct   4260
ctggacccac ccctgctgac tcgctacctg cgaatccacc cacagtcctg ggtgcatcag   4320
attgcactga gaatggaagt cctgggctgc gaggcccagg acctgtattg a            4371
```

<210> SEQ ID NO 8
<211> LENGTH: 222
<212> TYPE: DNA
<213> ORGANISM: Adeno-associated virus

<400> SEQUENCE: 8

```
gtctgtctgc acatttcgta gagcgagtgt tccgatactc taatctccct aggcaaggtt     60
catattgact taggttactt attctccttt tgttgactaa gtcaataatc agaatcagca    120
ggtttggagt cagcttggca gggatcagca gcctgggttg gaaggagggg gtataaaagc    180
cccttcacca ggagaagccg tcacacagat ccacaagctc ct                       222
```

<210> SEQ ID NO 9
<211> LENGTH: 4778
<212> TYPE: DNA
<213> ORGANISM: Adeno-associated virus

<400> SEQUENCE: 9

```
gtctgtctgc acatttcgta gagcgagtgt tccgatactc taatctccct aggcaaggtt     60
catattgact taggttactt attctccttt tgttgactaa gtcaataatc agaatcagca    120
ggtttggagt cagcttggca gggatcagca gcctgggttg gaaggagggg gtataaaagc    180
cccttcacca ggagaagccg tcacacagat ccacaagctc ctgctagcag gtaagtgccg    240
tgtgtggttc ccgcgggcct ggcctcttta cgggttatgg cccttgcgtg ccttgaatta    300
ctgacactga catccacttt ttctttttct ccacaggttt aaacgccacc atgcagattg    360
```

-continued

```
agctgtcaac ttgctttttc ctgtgcctgc tgagattttg tttttccgct actagaagat    420
actacctggg ggctgtggaa ctgtcttggg attacatgca gagtgacctg ggagagctgc    480
cagtggacgc acgatttcca cctagagtcc ctaaatcatt ccccttcaac accagcgtgg    540
tctataagaa aacactgttc gtggagttta ctgatcacct gttcaacatc gctaagcctc    600
ggccaccctg gatgggactg ctgggaccaa caatccaggc agaggtgtac gacaccgtgg    660
tcattacact gaaaaacatg gcctcacacc ccgtgagcct gcatgctgtg ggcgtcagct    720
actggaaggc ttccgaaggg gcagagtatg acgatcagac ttcccagaga gaaaaagagg    780
acgataaggt gtttcctggc gggtctcata cctatgtgtg gcaggtcctg aaagagaatg    840
gccccatggc ttccgaccct ctgtgcctga cctactctta tctgagtcac gtggacctgg    900
tcaaggatct gaacagcgga ctgatcggag cactgctggt gtgtagggaa gggagcctgg    960
ctaaggagaa aacccagaca ctgcataagt tcattctgct gttcgccgtg tttgacgaag   1020
gaaaatcatg gcacagcgag acaaagaata gtctgatgca ggaccgggat gccgcttcag   1080
ccagagcttg gcccaaaatg cacactgtga acggctacgt caatcgctca ctgcctggac   1140
tgatcggctg ccaccgaaag agcgtgtatt ggcatgtcat cggaatgggc accacacctg   1200
aagtgcactc cattttcctg gaggggcata cctttctggt ccgcaaccac cgacaggcct   1260
ccctggagat ctctccaatt accttcctga cagctcagac tctgctgatg gatctgggac   1320
agttcctgct gttttgccac atcagctccc accagcatga tggcatggag gcctacgtga   1380
aagtggacag ctgtcccgag gaacctcagc tgaggatgaa gaacaatgag gaagctgaag   1440
actatgacga tgacctgacc gactccgaga tggatgtggt ccgattcgat gacgataaca   1500
gcccctcctt tatccagatt agatctgtgg ccaagaaaca ccctaagaca tgggtccatt   1560
acatcgcagc cgaggaagag gactgggatt atgcaccact ggtgctggca ccagacgatc   1620
gatcctacaa atctcagtat ctgaacaatg gaccacagcg gattggcaga aagtacaaga   1680
aagtgaggtt catggcttat accgatgaaa ccttcaagac tcgcgaagca atccagcacg   1740
agagcgggat tctgggacca ctgctgtacg gagaagtggg ggacaccctg ctgatcattt   1800
ttaagaacca ggccagcagg ccttacaata tctatccaca tggaattaca gatgtgcgcc   1860
ctctgtacag ccggagactg ccaaagggcg tcaaacacct gaaggacttc ccaatcctgc   1920
ccggggaaat ttttaagtat aaatggactg tcaccgtcga ggatggcccc actaagagcg   1980
accctaggtg cctgacccgc tactattcta gtttcgtgaa tatggaaagg gatctggcca   2040
gcggactgat cggcccactg ctgatttgtt acaaagagag cgtggatcag agaggcaacc   2100
agatcatgtc cgacaagagg aatgtgattc tgttcagtgt ctttgacgaa aaccggtcat   2160
ggtatctgac cgagaacatc cagagattcc tgcctaatcc agccggagtg cagctggaag   2220
atcctgagtt tcaggcttct aacatcatgc atagtattaa tggctacgtg ttcgacagtc   2280
tgcagctgtc agtgtgtctg cacgaggtcg cttactggta tatcctgagc attggagcac   2340
agacagattt cctgagcgtg ttcttttccg gctacacttt taagcataaa atggtgtatg   2400
aggacacact gactctgttc cccttcagcg gcgaaaccgt gtttatgtcc atggagaatc   2460
ccgggctgtg gatcctggga tgccacaaca gcgatttcag gaatcgcggg atgactgccc   2520
tgctgaaagt gtcaagctgt gacaagaaca ccggagacta ctatgaagat tcatacgagg   2580
acatcagcgc atatctgctg tccaaaaaca atgccattga acccaggtct tttagtcaga   2640
atcctccagt gctgaagagg caccagcgcg agatcacccg cactaccctg cagagtgatc   2700
```

-continued aggaagagat cgactacgac gatacaattt ctgtggaaat gaagaaagag gacttcgata 2760
tctatgacga agatgagaac cagagtcctc gatcattcca gaagaaaacc cggcattact 2820
ttattgctgc agtggagcgc ctgtgggatt atggcatgtc ctctagtcct cacgtgctgc 2880
gaaatcgggc ccagtcaggg agcgtcccac agttcaagaa agtggtcttc caggagttta 2940
cagacggatc ctttactcag ccactgtacc ggggcgaact gaacgagcac ctggggctgc 3000
tgggacccta tatcagagct gaagtggagg ataacattat ggtcaccttc agaaatcagg 3060
catctaggcc ttacagtttt tattcaagcc tgatctctta cgaagaggac cagaggcagg 3120
gagcagaacc acgaaaaaac ttcgtgaagc ctaatgagac caaaacatac ttttggaagg 3180
tgcagcacca tatggcccca acaaaagacg aattcgattg caaggcatgg gcctattttt 3240
ctgacgtgga tctggagaag gacgtccaca gtggcctgat cgggccactg ctggtgtgtc 3300
atactaacac cctgaatccc gcacacggca ggcaggtcac tgtccaggaa ttcgccctgt 3360
tctttaccat ctttgatgag acaaaaagct ggtacttcac cgaaaacatg gagcgaaatt 3420
gccgggctcc atgtaatatt cagatggaag accccacatt caaggagaac taccgctttc 3480
atgccatcaa tgggtatatt atggatactc tgcccggact ggtcatggct caggaccaga 3540
gaatcaggtg gtacctgctg agcatggggt ccaacgagaa tatccactca attcatttca 3600
gcggacacgt gtttactgtc cggaagaaag aagagtataa aatggccctg tacaacctgt 3660
atcccggcgt gttcgaaacc gtcgagatgc tgcctagcaa ggcagggatc tggagagtgg 3720
aatgcctgat tggggagcac ctgcatgccg gaatgtctac cctgtttctg gtgtacagta 3780
ataagtgtca gacacccctg ggatggctt ccggacatat ccgggatttc cagattaccg 3840
catctggaca gtacggccag tggcccccta agctggctag actgcactat tccgggtcta 3900
tcaacgcttg gtccacaaaa gagcctttct cttggattaa ggtggacctg ctggcaccaa 3960
tgatcattca tggcatcaaa actcaggggg ccaggcagaa gttctcctct ctgtacatct 4020
cacagtttat catcatgtac agcctggatg gcaagaaatg gcagacatac cgcggcaata 4080
gcacagggac tctgatggtg ttctttggca acgtggacag ttcagggatc aagcacaaca 4140
ttttcaatcc ccctatcatt gctagataca tcaggctgca cccaacccat tattctattc 4200
gaagtacact gcggatggaa ctgatggggt gcgatctgaa cagttgttca atgcccctgg 4260
gaatggagtc caaggcaatc tctgacgccc agattaccgc tagctcctac ttcactaata 4320
tgtttgctac ctggagcccc tccaaagcac gactgcatct gcagggacga agcaacgcat 4380
ggcgaccaca ggtgaacaat cccaaggagt ggctgcaggt cgattttcag aaaactatga 4440
aggtgaccgg agtcacaact cagggcgtga aaagtctgct gacctcaatg tacgtcaagg 4500
agttcctgat ctctagttca caggacggcc accagtggac actgttcttt cagaacggaa 4560
aggtgaaagt cttccagggc aatcaggatt cctttacacc tgtggtcaac tctctggacc 4620
cacccctgct gactcgctac ctgcgaatcc acccacagtc ctgggtgcat cagattgcac 4680
tgagaatgga agtcctgggc tgcgaggccc aggacctgta ttgagcggcc gcaataaaag 4740
atcagagctc tagagatctg tgtgttggtt ttttgtgt 4778

<210> SEQ ID NO 10
<211> LENGTH: 4374
<212> TYPE: DNA
<213> ORGANISM: Adeno-associated virus

<400> SEQUENCE: 10
atgcagatcg agctgtctac ctgcttcttc ctgtgcctgc tgcggttctg cttcagcgcc 60

```
accagacggt actatctggg cgccgtggaa ctgagctggg actacatgca gagcgacctg    120
ggcgagctgc ccgtggatgc cagattccct ccaagagtgc ccaagagctt ccccttcaac    180
acctccgtgg tgtacaagaa aaccctgttc gtggaattca ccgaccacct gttcaatatc    240
gccaagccca gacccccctg gatgggcctg ctgggaccta caattcaggc cgaggtgtac    300
gacaccgtcg tgatcaccct gaagaacatg gccagccacc ccgtgtctct gcatgccgtg    360
ggagtgtcct actggaaggc ctctgagggc gccgagtacg acgatcagac cagccagcgc    420
gagaaagagg acgacaaggt gttccctggc ggcagccaca cctacgtgtg gcaggtgctg    480
aaagaaaacg gccccatggc ctccgaccct ctgtgcctga catacagcta cctgagccac    540
gtggacctcg tgaaggacct gaacagcggc ctgatcggag ccctgctcgt gtgtagagag    600
ggcagcctgg ccaaagagaa aacccagacc ctgcacaagt tcatcctgct gttcgccgtg    660
ttcgacgagg gcaagagctg gcacagcgag acaaagaaca gcctgatgca ggaccgggac    720
gccgcctctg ctagagcctg gcccaaaatg cacaccgtga acggctacgt gaacagaagc    780
ctgcccggac tgatcggctg ccaccggaag tctgtgtact ggcacgtgat cggcatgggc    840
accacccctg aggtgcacag catctttctg gaaggacaca cctttctcgt gcggaaccac    900
cggcaggcca gcctggaaat cagccctatc accttcctga ccgcccagac actgctgatg    960
gacctgggcc agtttctgct gttctgccac atcagctccc accagcacga cggcatggaa   1020
gcctacgtga aggtggacag ctgccccgag gaaccccagc tgcggatgaa gaacaacgag   1080
gaagccgagg actacgacga cgacctgacc gacagcgaga tggacgtggt gcgcttcgac   1140
gacgataaca gccccagctt catccagatc agaagcgtgg ccaagaagca ccccaagacc   1200
tgggtgcact atatcgccgc cgaggaagag gactgggatt acgcccctct ggtgctggcc   1260
cccgacgaca gaagctacaa gagccagtac ctgaacaatg gcccccagcg gatcggccgg   1320
aagtataaga aagtgcggtt catggcctac accgacgaga cattcaagac cagagaggcc   1380
atccagcacg agagcggcat cctgggccct ctgctgtatg gcgaagtggg cgacaccctg   1440
ctgatcatct tcaagaacca ggccagcaga ccctacaaca tctaccctca cggcatcacc   1500
gacgtgcggc ccctgtactc tagaaggctg cccaagggcg tgaaacacct gaaggacttc   1560
cccatcctgc ccggcgagat cttcaagtac aagtggaccg tgaccgtgga agatggcccc   1620
accaagagcg accccagatg cctgacacgg tactacagca gcttcgtgaa catggaacgg   1680
gacctggcct ccggcctgat tggcccactg ctgatctgct acaaagaaag cgtggaccag   1740
cggggcaacc agatcatgag cgacaagcgg aacgtgatcc tgtttagcgt gttcgatgag   1800
aaccggtcct ggtatctgac cgagaatatc cagcggttcc tgcccaaccc tgccggcgtg   1860
cagctggaag atcctgagtt ccaggcctcc aacatcatgc actccatcaa tggctatgtg   1920
ttcgacagcc tgcagctgag cgtgtgcctg cacgaggtgg cctactggta catcctgagc   1980
atcggggccc agaccgactt cctgtccgtg ttcttctccg gctacacctt caagcacaag   2040
atggtgtacg aggataccct gaccctgttc cccttttagcg gcgaaaccgt gttcatgagc   2100
atggaaaacc ccggcctgtg gatcctgggc tgccacaaca gcgacttccg gaacagaggc   2160
atgaccgccc tgctgaaggt gtccagctgc gacaagaaca ccggcgacta ctacgaggac   2220
agctatgagg acatcagcgc ctacctgctg agcaagaaca atgccatcga gcccagaagc   2280
ttcagccaga acccccccgt gctgaagcgg caccagagag agatcacccg gaccaccctg   2340
cagtccgacc aggaagagat cgattacgac gacaccatca gcgtggaaat gaagaaagaa   2400
```

-continued gatttcgaca tctacgacga ggacgagaac cagagccccc ggtcctttca gaaaaagacc 2460
cggcactact tcattgccgc tgtggaacgg ctgtgggact acggcatgag cagcagccct 2520
cacgtgctga gaaacagggc ccagagcggc agcgtgcccc agttcaagaa agtggtgttc 2580
caggaattca cagacggcag cttcacccag cctctgtacc gcggcgagct gaatgagcac 2640
ctgggactgc tgggccccta tatcagagcc gaagtggaag ataacatcat ggtcaccttc 2700
cggaatcagg cctcccggcc ctacagcttc tacagctccc tgatcagcta cgaagaggac 2760
cagagacagg gcgctgagcc ccggaagaac ttcgtgaagc ccaacgagac taagacctac 2820
ttttggaagg tgcagcacca catggcccct acaaaggacg agttcgactg caaggcctgg 2880
gcctacttct ccgatgtgga cctggaaaag gacgtgcact ctgggctgat cggcccccctg 2940 ctcgtgtgcc acaccaacac cctgaatccc gcccacggca gacaagtgac agtgcaggaa 3000
ttcgccctgt tcttcaccat cttcgacgaa acaaagagct ggtacttcac cgaaaacatg 3060
gaaagaaact gccgggctcc ctgcaacatc cagatggaag atcccacctt caaagagaac 3120
taccggttcc acgccatcaa cggctacatc atggacacac tgcccggcct cgtgatggct 3180
caggatcagc ggatccggtg gtatctgctg tccatgggct ccaacgagaa catccacagc 3240
atccacttca gcggccacgt gttcaccgtg cggaaaaaag aagagtacaa aatggccctg 3300
tacaacctgt accctggggt gttcgagaca gtggaaatgc tgcccagcaa ggccggcatc 3360
tggcgggtgg aatgtctgat cggcgagcat ctgcacgctg ggatgagcac actgtttctg 3420
gtgtacagca acaagtgcca gacacctctg ggcatggcct ctggccacat ccgggacttt 3480
cagatcacag ccagcggcca gtatggccag tgggccccaa aactggccag actgcactac 3540
agcggcagca tcaacgcctg gtccaccaaa gagcccttca gctggatcaa ggtggacctg 3600
ctggctccca tgatcatcca cggaatcaag acccagggcg ccagacagaa gttcagcagc 3660
ctgtacatca gccagttcat catcatgtac agcctggacg gcaagaagtg gcagacctac 3720
cggggcaata gcaccggcac cctgatggtg ttcttcggca acgtggactc cagcggcatt 3780
aagcacaaca tcttcaaccc ccccatcatt gcccggtaca tccggctgca ccccacccac 3840
tacagcatcc ggtccaccct gagaatggaa ctgatgggct gcgacctgaa ctcctgcagc 3900
atgcccctgg ggatggaaag caaggccatc tccgacgccc agatcaccgc ctccagctac 3960
ttcaccaaca tgttcgccac ctggtcccca tccaaggccc ggctgcatct gcagggcaga 4020
agcaatgctt ggaggcccca agtgaacaac cccaaagaat ggctgcaggt ggacttccag 4080
aaaaccatga aagtgaccgg cgtgaccacc cagggcgtga agtctctgct gacctctatg 4140
tacgtgaaag agttcctgat ctccagcagc caggacggcc accagtggac cctgtttttc 4200
cagaacggca aagtgaaagt gtttcagggg aaccaggact ccttcacccc cgtcgtgaat 4260
agcctggacc ctccactgct gaccagatac ctgcggatcc accctcagag ttgggtgcac 4320
cagattgctc tgcggatgga agtgctggga tgcgaggccc aggacctgta ctga 4374

<210> SEQ ID NO 11
<211> LENGTH: 4374
<212> TYPE: DNA
<213> ORGANISM: Adeno-associated virus

<400> SEQUENCE: 11
atgcagatcg agctgtctac ctgcttcttc ctgtgcctgc tgcggttctg ctttagcgct 60
actagacgct actacctggg cgccgtggaa ctgagctggg actatatgca gtcagacctg 120
ggcgagctgc ccgtggacgc tagattccca cctagagtgc ctaagagctt cccctttaac 180

```
acctccgtgg tctataagaa aaccctgttc gtcgagttca ccgatcacct gtttaatatc    240
gctaagccta gaccccccctg gatgggcctg ctgggcccta ctattcaggc cgaggtctac    300
gacaccgtcg tgatcaccct gaagaatatg gctagtcacc ccgtcagcct gcacgccgtg    360
ggcgtcagct actggaaggc tagcgagggc gccgagtacg acgatcagac tagtcagcgc    420
gagaaagagg acgacaaagt ctttcctggc ggctctcaca cctacgtgtg gcaggtcctg    480
aaagaaaacg gccctatggc tagcgacccc ctgtgcctga cctatagcta cctgagtcac    540
gtggacctgg tcaaggacct gaatagcggc ctgatcggcg ccctgctcgt gtgtagagag    600
ggctcactgg ctaaagagaa aactcagacc ctgcacaagt ttatcctgct gttcgccgtg    660
ttcgacgagg gcaagagctg gcactcagag actaagaata gcctgatgca ggatagggac    720
gccgctagcg ctagagcctg gcctaagatg cacaccgtga acggctacgt gaacagatca    780
ctgcccggac tgatcggctg tcaccggaag tccgtctact ggcacgtgat cggaatgggc    840
actacccccg aggtgcactc tatctttctg gaaggccaca ccttcctcgt cagaaatcac    900
cggcaggcta gcctcgagat tagccctatc accttcctga ccgctcagac actgctgatg    960
gacctgggcc agttcctgct gttttgtcac attagctctc accagcacga cgggatggaa   1020
gcctacgtga aagtggatag ctgccccgag gaacctcagc tgagaatgaa gaacaacgag   1080
gaagccgagg attacgacga cgacctgacc gatagcgaga tggacgtcgt cagattcgac   1140
gacgataact cacctagctt tattcagatt agatcagtgg ctaagaagca ccctaagacc   1200
tgggtgcact atatcgccgc cgaggaagag gactgggact acgcccctct ggtgctggcc   1260
cccgacgata gaagctataa gtctcagtac ctgaacaacg gccctcagcg gatcggccgg   1320
aagtataaga aagtgcggtt tatggcctac accgacgaaa ccttcaagac tagagaggct   1380
attcagcacg agtcagggat cctgggcccc ctgctctacg gcgaagtggg cgacaccctg   1440
ctgattatct ttaagaatca ggctagtagg ccctataata tctaccccca cggaatcacc   1500
gacgtgcggc ccctctactc tagacggctg cctaagggcg tgaagcacct gaaggacttc   1560
cctattctgc ccggcgagat ctttaagtac aagtggaccg tgaccgtcga ggacggccct   1620
actaagtccg accctcggtg cctgactagg tactactcta gcttcgtgaa tatggaacgg   1680
gacctggcta gcggactgat tggccctctg ctgatctgct acaaagaatc agtggatcag   1740
cggggcaatc agattatgag cgataagcgg aacgtgatcc tgtttagtgt gtttgacgag   1800
aataggtcct ggtatctgac cgagaatatc cagcggttcc tgcctaaccc tgccggcgtg   1860
cagctggaag atcccgagtt tcaggctagc aatattatgc actctattaa cggatacgtg   1920
ttcgatagcc tgcagctgag cgtgtgcctg cacgaggtgg cctactggta tatcctgtct   1980
atcggcgctc agaccgactt cctgagcgtg ttctttagcg gctacacctt taagcacaag   2040
atggtctacg aggataccct gaccctgttc ccctttagcg gcgaaaccgt gtttatgtct   2100
atggaaaacc ccggcctgtg gatcctgggg tgtcacaata gcgactttag gaatagagga   2160
atgaccgccc tgctgaaagt gtctagctgc gataagaaca ccggcgacta ttacgaggac   2220
tcttacgagg atattagcgc ctacctgctg tctaagaaca acgctatcga gcctagaagc   2280
ttcagtcaga acccccccgt gctgaagcgg caccagagag agatcactag aactaccctg   2340
cagagcgacc aggaagagat cgactacgac gacactatta gcgtcgagat gaagaaagag   2400
gatttcgata tctacgacga ggacgagaac cagtcaccta gatccttcca gaagaaaact   2460
aggcactact ttattgccgc cgtcgagcgg ctgtgggact acggaatgag ttctagccct   2520
```

-continued

```
cacgtgctga gaaatagggc tcagtcaggc tcagtgcctc agttcaagaa agtggtgttc   2580
caggaattca ccgacggcag cttcactcag cccctctata ggggcgagct gaacgagcac   2640
ctgggactgc tgggacctta tattagagcc gaagtcgagg acaatattat ggtcaccttt   2700
aggaaccagg cctctaggcc ctacagcttc tactctagcc tgatcagcta cgaggaagat   2760
cagcggcagg gggccgaacc tagaaagaac ttcgtgaagc ctaacgagac taagacctac   2820
ttctggaagg tgcagcacca catggcccct actaaggacg agttcgactg taaagcctgg   2880
gcctacttta gcgacgtgga cctcgagaag gacgtgcact cagggctgat cggacctctg   2940
ctcgtctgtc acactaacac cctgaacccc gctcacggcc ggcaggtcac agtgcaggaa   3000
ttcgccctgt tcttcactat cttcgacgaa actaagagct ggtacttcac agagaatatg   3060
gaaagaaact gtagggcccc ctgtaatatt cagatggaag atcctacctt taaagagaac   3120
tataggtttc acgctattaa cggctatatt atggacaccc tgcccggcct cgtgatggct   3180
caggatcagc ggattaggtg gtatctgctg tctatgggct ctaacgagaa tattcactct   3240
attcacttta gcggccacgt gttcaccgtc cggaagaaag aagagtataa gatggccctc   3300
tataacctct accccggcgt gttcgagaca gtggaaatgc tgcctagtaa agccggaatc   3360
tggcgggtcg agtgtctgat cggcgagcac ctccacgccg gaatgagcac cctgtttctg   3420
gtctactcta acaagtgtca gacccctctg ggaatggcta gcggccacat tagagacttt   3480
cagatcaccg ctagcggaca gtacggccag tgggccccta agctggctag actgcactat   3540
agcggatcta tcaacgcctg gtctaccaaa gagcccttta gctggattaa ggtggacctg   3600
ctggccccta tgattattca cgggattaag actcagggcg ctaggcagaa gtttagtagc   3660
ctctatatta gtcagtttat cattatgtat agcctggacg gcaagaagtg gcagacctat   3720
agaggcaata gcaccggcac cctgatggtg ttcttcggca acgtggactc tagcgggatc   3780
aagcacaata tctttaaccc ccctattatc gctagatata ttaggctgca ccctactcac   3840
tactctatta ggtctaccct gaggatggaa ctgatgggct gcgatctgaa tagctgctct   3900
atgcccctgg ggatggaatc taaggctatt agcgacgctc agatcacagc ctctagctac   3960
ttcactaata tgttcgctac ctggtcccct agcaaggccc ggctgcacct ccagggcaga   4020
tctaacgctt ggcggcctca ggtcaacaac cctaaagagt ggctgcaggt cgactttcag   4080
aaaactatga aggtcaccgg cgtgaccact cagggcgtga aatcactgct gacctctatg   4140
tacgtgaaag agttcctgat tagctctagc caggacggcc accagtggac cctgttcttt   4200
cagaacggca aagtgaaagt gtttcagggc aatcaggata gcttcacccc cgtggtcaat   4260
agcctggatc cccccactgct gactagatac ctgagaattc accctcagtc ttgggtgcac   4320
cagatcgccc tgagaatgga agtcctgggc tgtgaagctc aggacctcta ctaa         4374
```